(12) United States Patent
O'Connor-McCourt et al.

(10) Patent No.: US 8,658,135 B2
(45) Date of Patent: *Feb. 25, 2014

(54) ANTAGONISTS OF LIGANDS AND USES THEREOF

(75) Inventors: Maureen D. O'Connor-McCourt, Beaconsfield (CA); Traian Sulea, Kirkland (CA); John C. Zwaagstra, Chomedey-Laval (CA); Jason Baardsnes, Montreal (CA); Catherine Collins, Dorval (CA)

(73) Assignee: National Research Council of Canada, Ottawa, Ontario (CA)

(*) Notice: Subject to any disclaimer, the term of this patent is extended or adjusted under 35 U.S.C. 154(b) by 190 days.

This patent is subject to a terminal disclaimer.

(21) Appl. No.: 13/063,753

(22) PCT Filed: Sep. 17, 2009

(86) PCT No.: PCT/CA2009/001293
§ 371 (c)(1),
(2), (4) Date: May 12, 2011

(87) PCT Pub. No.: WO2010/031168
PCT Pub. Date: Mar. 25, 2010

(65) Prior Publication Data
US 2011/0236309 A1    Sep. 29, 2011

Related U.S. Application Data

(63) Continuation-in-part of application No. PCT/CA2008/000547, filed on Mar. 19, 2008.

(60) Provisional application No. 61/136,590, filed on Sep. 17, 2008.

(51) Int. Cl.
*A61K 38/16* (2006.01)
*C07K 14/47* (2006.01)

(52) U.S. Cl.
USPC .................. 424/9.1; 514/21.2; 530/350

(58) Field of Classification Search
None
See application file for complete search history.

(56) References Cited

U.S. PATENT DOCUMENTS

| 5,844,099 A | 12/1998 | Stahl et al. |
| 6,472,179 B2 | 10/2002 | Stahl et al. |

(Continued)

FOREIGN PATENT DOCUMENTS

| CA | 2345109 | 4/2000 |
| CA | 2681177 | 9/2008 |

(Continued)

OTHER PUBLICATIONS

Office Action dated Dec. 8, 2010 on European application 08733651.7.

(Continued)

*Primary Examiner* — Jeffrey E Russel
(74) *Attorney, Agent, or Firm* — Sonia Patenaude

(57) ABSTRACT

The invention provides hetero-multivalent ligand binging agents (traps) for members of the TGF-β superfamily, as well as methods for making and using such constructs. In an embodiment of the invention there is provided a hetero-multivalent binding agent with affinity for a member of the TGF-β superfamily. The agent comprises the general structure I:

$$(<bd1>\text{-linker1})_k\text{-}[\{<bd1>\text{-linker2-}<bd2>\text{-linker3}_f\}_n\text{-}(<bd3>)_m\text{-}(\text{linker4-}<bd4>)_d]_h,$$

where bd1, bd2, bd3 and bd4 are polypeptide binding domains having an affinity for different sites on the same member or for different members of the TGF-β superfamily; at least two of bd1, bd2, bd3, and bd4 are different from each other.

12 Claims, 14 Drawing Sheets

(56) References Cited

U.S. PATENT DOCUMENTS

| | | | |
|---|---|---|---|
| 6,897,294 | B2 | 5/2005 | David-Smyth et al. |
| 6,916,913 | B2 | 7/2005 | Jessell et al. |
| 7,795,389 | B2 | 9/2010 | Sun et al. |
| 8,318,135 | B2 * | 11/2012 | O'Connor-McCourt et al. ............... 424/9.1 |
| 2002/0173621 | A1 * | 11/2002 | Sledziewski et al. ......... 530/350 |
| 2003/0125251 | A1 | 7/2003 | Wakefield et al. |
| 2004/0176282 | A1 * | 9/2004 | Dalby et al. ...................... 514/8 |
| 2007/0086942 | A1 * | 4/2007 | Chang et al. ................. 424/1.49 |
| 2007/0154994 | A1 | 7/2007 | De Crescenzo et al. |
| 2007/0244042 | A1 | 10/2007 | Sun et al. |
| 2010/0120147 | A1 | 5/2010 | O'Connor-McCourt et al. |

FOREIGN PATENT DOCUMENTS

| | | |
|---|---|---|
| CA | 2737271 | 3/2010 |
| EP | 1405915 | 4/2004 |
| EP | 1486560 | 12/2004 |
| WO | 03/020906 | 3/2003 |
| WO | 2008/113185 | 9/2008 |
| WO | 2008/157367 | 12/2008 |
| WO | 2010/031168 | 3/2010 |

OTHER PUBLICATIONS

International Preliminary Report on Patentability dated Jun. 5, 2009 on on PCT-CA2008-000547.
International Preliminary Report on Patentability dated Mar. 31, 2011 on PCT-CA2009-001293.
Written Opinion and International Search Report dated Dec. 10, 2009 on PCT-CA2009-001293.
Written Opinion and International Search Report dated Jul. 18, 2008 on PCT-CA2008-000547.
Extended European Search Report dated Mar. 22, 2010 on European application 08733651.7.
Abe, et al., Analytical Biochemistry, 216, pp. 276-284 (1994).
Allendorph et al. PNAS. vol. 103, No. 20, pp. 7643-7648 (2006).
Andreeva et al. Nucleic Acids Research. vol. 36, Database issue D419-D425 (2008).
Baardsnes et al., Biochemistry, 48, pp. 2146-2155 (2009).
Berman et al. Nucleic Acids Research. vol. 28, No. 1, pp. 235-242 (2000).
Boesen et al. Structure. vol. 10, pp. 913-919 (2002).
Broussau et al., American Society of Gene Therapy, vol. 16, No. 3, pp. 500-507 (2008).
Case et al. J Comput Chem. 26, 1668-1688 (2005).
Cass et al. Protein Expression and Purification. 40, 77-85 (2005).
Cornell et al. J. Am. Chem. Soc. 117, 5179-5197 (1995).
Darden et al. J. Chem. Phys. 98(12) 10089-10092 (1993).
De Crescenzo et al. The Journal of Biological Chemistry. vol. 279, No. 25, Issue of Jun. 18, pp. 26013-26018 (2004).
De Crescenzo et al. The Journal of Biological Chemistry. vol. 276, No. 32, Issue of Aug. 10, pp. 29632-29643 (2001).
De Crescenzo et al., J.Mol.Biol., 355, pp. 47-62 (2006).
Deep et al. Biochemistry. 42, 10126-10139 (2003).
Dennler et al. The EMBO Journal. vol. 17, No. 11, pp. 3091-3100 (1998).
Duan et al. J Comput Chem. 24, 1999-2012 (2003).
Durocher et al., Nucleic Acids Research, vol. 30, No. 2e9 (2002).
Economides et al. Nature Medicine. vol. 9, No. 1, pp. 47-52 (2003).
Esparza-Lopez et al. The Journal of Biological Chemistry. vol. 276, No. 18, Issue of May 4, pp. 14588-14596 (2001).
Finn et al. Nucleic Acids Research. vol. 34, Database issue D247-D251 (2006).
George et al., Protein Engineering, vol. 15, No. 11 pp. 871-879 (2003).
Greenwald et al. Molecular Cell. vol. 15, pp. 485-489 (2004).
Greenwald et al. Molecular Cell. vol. 11, pp. 605-617 (2003).
Groppe et al. Molecular Cell. 29, 157-168 (2008).
Hart et al. Nature: Structural Biology. vol. 9, No. 3, pp. 203-208 (2002).
Hinck et al. Biochemistry. 35, 8517-8534 (1996).
Holash et al. PNAS. vol. 99, No. 17, pp. 11393-11398 (2002).
Kingsley, Genes & Development, pp. 133-146 (1994).
Kirsch et al. Nature: Structural Biology. vol. 7, No. 6, pp. 492-496 (2000).
Larrain et al. Development. 127, 821-830 (2000).
Lee et al. Proteins: Structure, Function, and Bioinformatics. 55, 620-634 (2004).
Mittl et al. Protein Science. 5:1261-1271 (1996).
Naim et al. J. Chem. Inf. Model. 47, 122-133 (2007).
Pham et al. Biotechnology and Engineering. vol. 90, No. 3, pp. 332-344 (2005).
Ryckaert et al. Journal of Computational Physics. 23, 327-341 (1977).
Thompson et al. The EMBO Journal. vol. 22, No. 7, pp. 1555-1566 (2003).
Ward et al. J. Mol. Biol. 337, 635-645 (2004).
Zilberberg et al. BMC Cell Biology. 8, 41 (2007).

* cited by examiner

| TGF-β-superfamily receptor | Sequences corresponding to unstructured extracellular regions | |
|---|---|---|
| Human TβR-II | $^{1}$IPPHVQKSVNNDMIVTDNNGAVKFP$^{25}$ | SEQ ID NO 1 |
| | $^{127}$SEEYNTSNPD$^{136}$ | SEQ ID NO 21[1] |
| Human TβR-IIb | $^{1}$IPPHVQKSDVEMEAQKDEIICPSCNRTAHPLRHINNDMIVTDNNGAVKFP$^{50}$ | SEQ ID NO 3 |
| | $^{152}$SEEYNTSNPD$^{161}$ | SEQ ID NO 21[1] |
| Human TβR-I | $^{1}$AALLPGAT$^{8}$ | SEQ ID NO 4 |
| | $^{88}$PTTVKSSPGLGPVE$^{101}$ | SEQ ID NO 5 |
| Human ActR-IIa | $^{1}$AILGRSE$^{7}$ | SEQ ID NO 6 |
| | $^{99}$EMEVTQPTSNPVTPKPPYYNI$^{120}$ | SEQ ID NO 7 |
| Human ActR-IIb | $^{1}$SGRGEAET$^{8}$ | SEQ ID NO 8 |
| | $^{99}$EAGGPEVTYEPPPTAPT$^{116}$ | SEQ ID NO 9 |
| Human BMPR-Ia | $^{1}$QNLDSMLHGTGMKSDSDQKKSENGVTLAPED$^{31}$ | SEQ ID NO 10 |
| | $^{117}$PVVIGPFFDGSIR$^{129}$ | SEQ ID NO 11 |

Fig. 1A

| TGF-β-superfamily receptor | Sequences corresponding to structured extracellular regions (ligand-binding domains) |
|---|---|
| Human TβR-II | $^{26}$QLCKFCDVRFSTCDNQKSCMSNCSITSICEKPQEVCVAVWRKNDENITLETVCHDPKLPYHDFILE DAASPKCIMKEKKKPGETFFMCSCSSDECNDNIIF$^{126}$ SEQ ID NO 12 |
| Human TβR-IIb | $^{51}$QLCKFCDVRFSTCDNQKSCMSNCSITSICEKPQEVCVAVWRKNDENITLETVCHDPKLPYHDFILE DAASPKCIMKEKKKPGETFFMCSCSSDECNDNIIF$^{151}$ SEQ ID NO 13 |
| Human TβR-I | $^{9}$ALQCFCHLCTKDNFTCVTDGLCFVSVTETTDKVIHNSMCIAEIDLIPRDRPFVCAPSSKTGSVTTY CCNQDHCNKIEL$^{87}$ SEQ ID NO 14 |
| Human ActR-IIa | $^{8}$TQECLFFNANWEKDRTNQTGVEPCYGDKDKRRHCFATWKNISGSIEIVKQGCWLDDINCYDRTDCVE KKDSPEVYFCCCEGNMCNEKFSYFP$^{98}$ SEQ ID NO 15 |
| Human ActR-IIb | $^{9}$RECIYYNANWELERTNQSGLERCEGEQDKRLHCYASWRNSSGTIELVKKGCWLDDFNCYDRQECVAT EENPQVYFCCCEGNFCNERFTHLP$^{98}$ SEQ ID NO 16 |
| Human BMPR-Ia | $^{32}$TLPFLKCYCSGHCPDDAINNTCITNGHCFAIIEEDDQGETTLASGCMKYEGSDFQCKDSPKAQLRR TIECCRTNLCNQYLQPTLP$^{116}$ SEQ ID NO 17 |

Fig. 1B

| Linker length (a.a.) | Linkers of natural sequence | |
|---|---|---|
| 35 | $^{127}$SEEYNTSNPD:IPPHVQKSVNNDMIVTDNNGAVKFP$^{161}$ | SEQ ID NO 18 |
| 60 | $^{127}$SEEYNTSNPD:IPPHVQKSDVEMEAQKDEIICPSCNRTAHPLRHINNDMIVTDNNGAVKFP$^{187}$ | SEQ ID NO 19 |
| 25 | $^{99}$EAGGPEVTYEPPPTAPT:SGRGEAET$^{124}$ | SEQ ID NO 20 |
| 44 | $^{117}$PVVIGPFFDGSIR:QNLDSMLHGTGMKSDSDQKKSENGVTLAPED$^{160}$ | SEQ ID NO 21 |

Fig. 2A

| Identity to natural linker (%) | Linkers of artificial sequence |
|---|---|
| 98 | $^{117}$PVVIGPFFDGSIRGNLDSMLHGTGMKSDSDQKKSENGVTLAPED$^{160}$ SEQ ID NO 22 |
| 97 | $^{127}$SEEYNTSNPDGPPHVQKSVNNDMIVTDNNGAVKFP$^{161}$ SEQ ID NO 23 |
| 96 | $^{99}$EAGGPEVTGEPPPTAPTSGRGEAET$^{124}$ SEQ ID NO 24 |
| 95 | $^{127}$SEEYNTSNPDGGRHVQKSDVEMEAQKDEIICPSCNRTAHPLRHINNDMIVTDNNGAVKFP$^{187}$ SEQ ID NO 25 |
| 94 | $^{127}$SEEYNTSNPDGPPHVQKSVNNDMIVTDNNGAVKFP$^{161}$ SEQ ID NO 26 |
| 91 | $^{127}$SEEYNTSNPDGGRHVQKSVNNDMIVTDNNGAVKFP$^{161}$ * SEQ ID NO 27 |
| 85 | $^{127}$SEEYNTSNPSGGGSGGGSGGGMEAQKDEIICPSCNRTAHPLRHINNDMIVTDNNGAVKFP$^{187}$ SEQ ID NO 28 |
| 80 | $^{127}$SEEYNTSNPSGGGSGGGKSVNNDMIVTDNNGAVKFP$^{161}$ SEQ ID NO 29 |
| 69 | $^{127}$SEEYNTSNPSGGGSGGGSGGGDMIVTDNNGAVKFP$^{161}$ SEQ ID NO 30 |
| 57 | $^{127}$SEEYNTSNPDIPPHVQKSGGGSGGGSGGGSGGGSGGGSGGGSVNNDMIVTDNNGAVKFP$^{187}$ SEQ ID NO 31 |
| 43 | $^{127}$SEEYNTSNPDGGSGGGSGGGSGGGSGGGSGGGSGGGSGGGNNDMIVTDNNGAVKFP$^{187}$ SEQ ID NO 32 |

Fig. 2B

| Linker length (aa) | Linker sequences | |
|---|---|---|
| 35 | ¹²⁷SEEYNTSNPDIPPHVQKSVNNDMIVTDNNGAVKFP¹⁶¹ | SEQ ID NO 33 |
| 48 | ¹²⁷SEEYNTSNPDIPPHVQKSVNNDMIPPHVQKSVNNDMIVTDNNGAVKFP¹⁷⁴ | SEQ ID NO 34 |
| 33 | ¹²⁷SEEYNTSN--PPHVQKSVNNDMIVTDNNGAVKFP¹⁵⁹ | SEQ ID NO 35 |
| 43 | ¹²⁷SEEYNTSNPDGGGGGIPPHVQKSVNNDMIVTDNNGAVKFP¹⁶⁹ | SEQ ID NO 36 |
| 47 | ¹²⁷SEEYNTSNPDGGGSGGGSGGGSIPPHVQKSVNNDMIVTDNNGAVKFP¹⁷³ | SEQ ID NO 37 |
| 60 | ¹²⁷SEEYNTSNPDIPPHVQKSDVEMEAQKDEIICPSCNRTAHPLRHINNDMIVTDNNGAVKFP¹⁸⁷ | SEQ ID NO 38 |
| 53 | ¹²⁷SEEYNTSNPDIPPHVQKSDVEMEAQKDE------RTAHPLRHINNDMIVTDNNGAVKFP¹⁸⁰ | SEQ ID NO 39 |
| 25 | ⁹⁹EAGGPEVTYEPPPTAPTSGRGEAET¹²⁴ | SEQ ID NO 40 |
| 35 | ⁹⁹EAGGPEVTYEPPPTAPTGGGGGGGGGSGRGEAET¹³⁴ | SEQ ID NO 41 |
| 44 | ¹¹⁷PVVIGPFFDGSIRQNLDSMLHGTGMKSDSDQKKSENGVTLAPED¹⁶⁰ | SEQ ID NO 42 |
| 40 | ¹¹⁷PVVIGP---DGSIRQNLDS---HGTGMKSDSDQKKSENGVTLAPED¹⁵⁶ | SEQ ID NO 43 |

Fig. 2C

| | |
|---|---|
| TβR-I/I/-v1<br>SEQ ID NO 44 | AALLPGATALQCFCHLCTKDNFTCVTDGLCFVSVTETTDKVIHNSMCIAEIDLIPRDRPFVCAPSSKTGSVTTTYCCNQDHCNKIELPTTVTDNNGAVKFPQLCKF<br>CDVRFSTCDNQKSQMSNCSITSICEKPQEVCVAVWRKNDENITLETVCHDPKLPYHDFILEDAASPKCIMKEKKKPGETFFMCSCSSDECNDNIIFSEEYNTSNPD |
| TβR-I/I/-v2<br>SEQ ID NO 45 | AALLPGATALQCFCHLCTKDNFTCVTDGLCFVSVTETTDKVIHNSMCIAEIDLIPRDRPFVCAPSSKTGSVTTTYCCNQDHCNKIELGGGGGNGAVKFPQLCKF<br>CDVRFSTCDNQRSQMSNCSITSICEKPQEVCVAVWRKNDENITLETVCHDPKLPYHDFILEDAASPKCIMKEKKKPGETFFMCSCSSDECNDNIIFSEEYNTSNPD |
| TβR-I/II/II<br>SEQ ID NO 46 | AALLPGATALQCFCHLCTKDNFTCVTDGLCFVSVTETTDKVIHNSMCIAEIDLIPRDRPFVCAPSSKTGSVTTTYCCNQDHCNKIELPTTVTDNNGAVKFPQLCKF<br>CDVRFSTCDNQKSQMSNCSITSICEKPQEVCVAVWRKNDENITLETVCHDPKLPYHDFILEDAASPKCIMKEKKKPGETFFMCSCSSDECNDNIIFSEEYNTSNPD<br>GGGSGGGSGGGSIPPHVQKSVNNDMIVTDNNGAVKFPQLCKFCDVRFSTCDNQRSCMSNCSITSICEKPQEVCVAVWRKNDENITLETVCHDPKLPYHDFILEDAA<br>SPKCIMKEKKKPGETFFMCSCSSDECNDNIIFSEEYNTSNPD |
| TβR-I/II/IIb<br>SEQ ID NO 47 | AALLPGATALQCFCHLCTKDNFTCVTDGLCFVSVTETTDKVIHNSMCIAEIDLIPRDRPFVCAPSSKTGSVTTTYCCNQDHCNKIELPTTVTDNNGAVKFPQLCKF<br>CDVRFSTCDNQKSQMSNCSITSICEKPQEVCVAVWRKNDENITLETVCHDPKLPYHDFILEDAASPKCIMKEKKKPGETFFMCSCSSDECNDNIIFSEEYNTSNPD<br>IPPHVQKSDVEMEAQKDEIICPSCNRTAHPLRHINNDMIVTDNNGAVKFPQLCKFCDVRFSTCDNQKSCMSNCSITSICEKPQEVCVAVWRKNDENITLETVCHDP<br>KLPYHDFILEDAASPKCIMKEKKKPGETFFMCSCSSDECNDNIIFSEEYNTSNPD |
| TbR-I/II/II-v1<br>SEQ ID NO 48 | AALLPGATALQCFCHLCTKDNFTCVTDGLCFVSVTETTDKVIHNSMCIAEIDLIPRDRPFVCAPSSKTGSVTTTYCCNQDHCNKIELPTTVTDNNGAVKFPQLCKF<br>CDVRFSTCDNQKSQMSNCSITSICEKPQEVCVAVWRKNDENITLETVCHDPKLPYHDFILEDAASPKCIMKEKKKPGETFFMCSCSSDECNDNIIFSEEYNTSNPD<br>GGGSGGGSGGGSGGGSGGGSGGGSAIQCFCHLCTKDNFFCVTDGLCFVSVTETTDKVIHNSMCIAEIDLIPRDRPFVCAPSSKTGSVTTTYCCNQDHC<br>NKIELPTTVTDNNGAVKFPQLCKFCDVRFSTCDNQKSCMSNCSITSICEKPQEVCVAVWRKNDENITLETVCHDPKLPYHDFILEDAASPKCIMKEKKKPGETFFM<br>CSCSSDECNDNIIFSEEYNTSNPD |

Fig. 4B

TβR-I/II/II-v2
SEQ ID NO 49

AALLPGATALQCFCHLCTKDNFTCVTDGLCFVSVTETTDKVIHNSMCIAEIDLIPRDRPFVCAPSSKTGSVTTYCCNQDHCNKIELGGGGSGGGGSGGGGSGGGGSGGGGSCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPDCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPDGGGSGGGSGGGGSGGGGSGGGGSGGGGSCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD

TβR-I/II/II
SEQ ID NO 50

AALLPGATALQCFCHLCTKDNFTCVTDGLCFVSVTETTDKVIHNSMCIAEIDLIPRDRPFVCAPSSKTGSVTTYCCNQDHCNKIELGGGGSGGGGSGGGGSGGGGSGGGGSCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPDGGGSGGGSGGGGSIPPHVQKSVNNDMIVTDNNGAVKFPQLCKFPQLCKFDVRFSTCDMQKSGGGSGGGGSGGGGSGGGGSGGGGSCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPDLIPRDRPFVCAPSSKTGSVTTYCCNQDHCNKIELPTTVKSSPGLGPVE

TβR-I/II/II
SEQ ID NO 51

AALLPGATALQCFCHLCTKDNFTCVTDGLCFVSVTETTDKVIHNSMCIAEIDLIPRDRPFVCAPSSKTGSVTTYCCNQDHCNKIELPTTVKSSPGLGPVEGGGSGGGSGGGNGAVKGGSGGGGSGGGSGGGGSIPPHVQKSVNNDMIVTDNNGAVKFPQLCKFDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPDGGGSGGGSGGGGSCDVRFSTCDNQKSCMSNCSITSICEKPQEVCVAVWRKNDENITLETVCHDPKLPYHDFILEDAASPKCIMKEKKKPGETFFMCSCSSDECNDNIIFSEE YNTSNPD

Fig. 4B (cont'd)

| Label | Sequence |
|---|---|
| TβR-I/II-v1<br>SEQ ID NO 44 | AALLPGATALQCFCHLCTKDNFTCVTDGLCFVSVTETTDKVIHNSMCIAEIDLIPRDRPFVCAPSSKTGSVTTTYCCNQDHCNKIELPTIVTDNNGAV<br>KFPQLCKFCDVRFSTCDNQRSCMSNCSITSICEKPQEVCVAVWRKNDENITLETVCHDFKLPYHDFILEDAASPKCIMKEKKPGETFFMCSCSSDE<br>CNDNIIFSEEYNTSNPD |
| TβR-I/II-v1a<br>SEQ ID NO 52 | AALLPGATALQCFCHLCTKDNFTCVTDGLCFVSVTETTDKVIHNSMCIAEIDLIPRDRPFVCAPSSKTGSVTTTYCCNQDHCNKIELPTTVVTDNNGA<br>VKFPQLCKFCDVRFSTCDNQKSCMSNCSITSICEKPQEVCVAVWRKDENITLETVCHDPKLPYHDFILEDAASPKCIMKEKKPGETFFMCSCSSDE<br>CNDNIIFSEEYNTSNPD |
| TβR-I/II-v1b<br>SEQ ID NO 53 | AALLPGATALQCFCHLCTKDNFTCVTDGLCFVSVTETTDKVIHNSMCIAEIDLIPRDRPFVCAPSSKTGSVTTTYCCNQDHCNKIELPTTVKSSPGNG<br>AVKFPQLCKFCDVRFSTCDNQKSCMSNCSITSICEKPQEVCVAVWRKNDENITLETVCHDPKLPYHDFILEDAASPKCIMKEKKPGETFFMCSCSSD<br>ECNDNIIFSEEYNTSNPD |
| TβR-I/II-v1c<br>SEQ ID NO 54 | AALLPGATALQCFCHLCTKDNFTCVTDGLCFVSVTETTDKVIHNSMCIAEIDLIPRDRPFVCAPSSKTGSVTTTYCCMQDHCNKIELNDMIVTDNNGA<br>VKFPQLCKFCDVRFSTCDNQKSCMSNCSITSICEKPQEVCVAVWRKNDENITLETVCHDPKLPYHDFILEDAASPKCIMKEKKPGETFFMCSCSSDE<br>CNDNIIFSEEYNTSNPD |
| ActR-IIa/BMPR-Ia-v1<br>SEQ ID NO 55 | AILGRSETQECLFFNANWEKDRTNQTGVEPCYGDKDKRRHCFATWKNISGSIEIVKQGCWLDDINCYDRTDCVEKKDSPEVYFCCCEGNMCNEKFSYF<br>PEMEVTQPTSDQKKSENGVTLAPEDTLPFLKPFLKCYCSGHCPDDAINNTCITNGHCFAIIEEDDQGETTLASGCMKYEGSDFQCKDSPKAQLRRTIECCRT<br>NLCNQYLQPTLPPVVIGPFFDGSIR |
| ActR-IIa/BMPR-Ia-v1a<br>SEQ ID NO 56 | AILGRSETQECLFFNANWEKDRTNQTGVEPCYGDKDKRRHCFATWKNISGSIEIVKQGCWLDDINCYDRTDCVEKKDSPEVYFCCCEGNMCNEKFSYF<br>PEMEVTQPTSDSDQKKSENGVTLAPEDTLPFLKCYCSGHCPDDAINNTCITNGHCFALIEEDDQGETTLASGCMKYEGSDFQCKDSPKAQLRRTIECC<br>RTNLCNQYLQPTLPPVVIGPFFDGSIR |
| ActR-IIa/BMPR-Ia-v1b<br>SEQ ID NO 57 | AILGRSETQECLFFNANWEKDRTNQTGVEPCYGDKDKRRHCFATWKNISGSIEIVKQGCWLDDINCYDRTDCVEKKDSPEVYFCCCEGNMCNEKFSYF<br>PEMEVTQPTSNPVTPKSDSDQKKSENGVTLAPEDTLPFLKCYCSGHCPDDAINNTCITNGHCFAIIEEDDQGETTLASGCMKYEGSDFQCKDSPKAQL<br>RRTIECCRTNLCNQYLQPTLPPVVIGPFFDGSIR |
| ActR-IIa/BMPR-Ia-v1c<br>SEQ ID NO 58 | AILGRSETQECLFFNANWEKDRTNQTGVEPCYGDKDKRRHCFATWKNISGSIEIVKQGCWLDDINCYDRTDCVEKKDSPEVYFCCCEGNMCNEKFSYF<br>PEMEVTQPTSNPVTGMKSDSDQKKSENGVTLAPEDTLPFLKCYCSGHCPDDAINNTCITNGHCFAIIEEDDQGETTLASGCMKYEGSDFQCKDSPKAQ<br>LRRTIECCRTNLCNQYLQPTLPPVVIGPFFDGSIR |

Fig. 5

| | |
|---|---|
| TβR-I/II-v2<br>SEQ ID NO 45 | AALLPGATALQCFCHLCTKDNFTCVTDGLCFVSVTETTDKVIHNSMCIAEIDLIPRDRPFVCAPSSKTGSVTTTYCCNQDHCNKIELGGGGGGNGAV<br>KFPQLCKFCDVRFSTCDNQKSCMSNCSITSICEKPQEVCVAVWRKNDENITLETVCHDPKLPYHDFILEDAASPKCIMKEKKPGETFFMCSCSSDEC<br>NDNIIFSEEYNTSNPD |
| TβR-I/II-v2a<br>SEQ ID NO 59 | AALLPGATALQCFCHLCTKDNFTCVTDGLCFVSVTETTDKVIHNSMCIAEIDLIPRDRPFVCAPSSKTGSVTTTYCCNQDHCNKIELGGGGGGNGA<br>VKFPQLCKFCDVRFSTCDNQKSCMSNCSITSICEKPQEVCVAVWRKNDENITLETVCHDPKLPYHDFILEDAASPKCIMKEKKPGETFFMCSCSSDE<br>CNDNIIFSEEYNTSNPD |
| TβR-I/II-v2b<br>SEQ ID NO 60 | AALLPGATALQCFCHLCTKDNFTCVTDGLCFVSVTETTDKVIHNSMCIAEIDLIPRDRPFVCAPSSKTGSVTTTYCCNQDHCNKIELGSGGGSNGAV<br>KFPQLCKFCDVRFSTCDNQKSCMSNCSITSICEKPQEVCVAVWRKNDENITLETVCHDPKLPYHDFILEDAASPKCIMKEKKPGETFFMCSCSSDEC<br>NDNIIFSEEYNTSNPD |
| TβR-I/II-v2c<br>SEQ ID NO 61 | AALLPGATALQCFCHLCTKDNFTCVTDGLCFVSVTETTDKVIHNSMCIAEIDLIPRDRPFVCAPSSKTGSVTTTYCCNQDHCNKIELGGSGGSGNGA<br>VKFPQLCKFCDVRFSTCDNQKSCMSNCSITSICEKPQEVCVAVWRKNDENITLETVCHDPKLPYHDFILEDAASPKCIMKEKKPGETFFMCSCSSDE<br>CNDNIIFSEEYNTSNPD |
| ActR-IIa/BMPR-Ia-v2<br>SEQ ID NO 62 | AILGRSETQECLFFNANWEKDRTNQTGVEPCYGDKDKRRHCFATWKNISGSIETVKQGCWLDDINCYDRTDCVEKKDSPEVYFCCCEGNMCNEKFSYF<br>PGGGGGGGGGGGGGSGGGGGGGGGGSGGTLPFLKCYCSGHCPDDAINNTCITNGHCFAIIEEDDQGETTLASGCMKYEGSDFQCKDSPKAQLRRTIECCRT<br>NLCNQYLQPTLPPVVIGPFFDGSIR |
| ActR-IIa/BMPR-Ia-v2a<br>SEQ ID NO 63 | AILGRSETQECLFFNANWEKDRTNQTGVEPCYGDKDKRRHCFATWKNISGSIETVKQGCWLDDINCYDRTDCVEKKDSPEVYFCCCEGNMCNEKFSYF<br>PGGSGGGGGSGGSGSGSGSGSGGSGGTLPFLKCYCSGHCPDDAINNTCITNGHCFAIIEEDDQGETTLASGCMKYEGSDFQCKDSPKAQLRRTIECC<br>RTNLCNQYLQPTLPPVVIGPFFDGSIR |
| ActR-IIa/BMPR-Ia-v2b<br>SEQ ID NO 64 | AILGRSETQECLFFNANWEKDRTNQTGVEPCYGDKDKRRHCFATWKNISGSIETVKQGCWLDDINCYDRTDCVEKKDSPEVYFCCCEGNMCNEKFSYF<br>PGGSGGGSGGGSGGGSGGGSGGGSGGGSGGGSGGTLPFLKCYCSGHCPDDAINNTCITNGHCFAIIEEDDQGETTLASGCMKYEGSDFQCKDSPKAQL<br>RRTIECCRTNLCNQYLQPTLPPVVIGPFFDGSIR |

Fig. 6

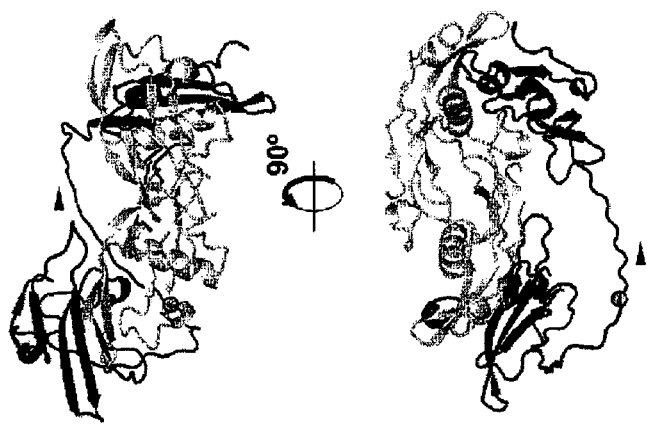
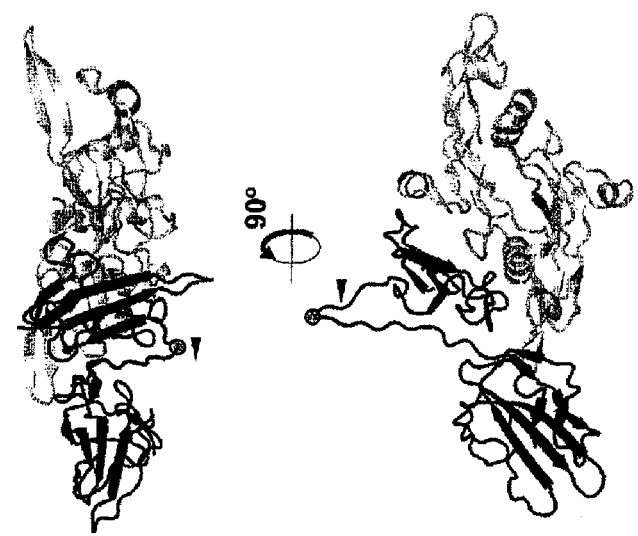
Fig. 7

ANTAGONISTS OF LIGANDS AND USES THEREOF

CROSS-REFERENCE TO RELATED APPLICATIONS

This application is a national phase entry of International Patent Application PCT/CA2009/001293 filed Sep. 17, 2009, which claims the benefit of U.S. Provisional Patent Application Ser. No. 61/136,590 filed Sep. 17, 2008, and is a continuation-in-part of International Patent Application PCT/CA2008/000547 filed Mar. 19, 2008.

FIELD OF INVENTION

The invention relates to the field of antagonists and, more specifically, to polypeptide antagonists capable of use as single chain multivalent ligand traps.

BACKGROUND OF INVENTION

Many undesirable biological processes occur via ligand binding to cell surface receptors. Thus, it is sometimes desirable to have compounds and methods to reduce or modulate such binding.

The TGF-β superfamily includes a number of ligands of biological significance.

TGF-β and Activin play critical pathogenic roles in many diseases including the progression of cancer and uncontrolled fibrosis and scarring of tissues, e.g. kidney, lung and liver fibrotic diseases. Furthermore, Myostatin/GDF8 is another ligand which is related to Activin and which shares binding to the same Type II receptor (ActivinRIIb). Myostatin is a powerful inhibitor of skeletal muscle growth and is a validated therapeutic target for muscle wasting diseases such as muscular dystrophy. Bone morphogenetic proteins (BMP), which are other ligands in the TGF-β family, have been implicated in cardiovascular diseases. For example, high levels of both BMP2 and BMP4 have been found in calcified atherosclerotic plaques and diseased aortic valves.

Principal agents that target these ligands are ligand traps/antagonists that bind and sequester ligand. Two examples are: 1) anti-ligand antibodies and 2) soluble receptor ectodomains.

Efforts have been made to identify methods to reduce ligand binding by trapping ligand and preventing its interaction with the cell surface receptors. Inhibition of certain ligands has been reported using anti-ligand antibodies that trap and neutralize the ligand directly. For therapeutic and diagnostic applications, however, antibodies are problematic, particularly due to issues arising from their large size restricting their ability to reach targets outside the bloodstream.

Soluble versions of receptor ectodomains antagonize ligands directly by binding to them and preventing them from interacting with cell surface receptors. In the case of TGF-β, in animal models, expression of a TGF-β receptor type II (TβRII) ectodomain (ED) partially restored host immunity and promoted tumor clearance, indicating that receptor ectodomain-mediated neutralization of TGF-β inhibits tumor progression. It has been shown, however, that the efficacy of monovalent TβRII-ED to antagonize TGF-β is less than could be desired. Attempts to overcome this led to the production of bivalent artificially dimerized forms of versions of TβRII-ED, dimerized via fusion to either coiled-coil domains or the Fc domain of IgG. This dimerization improved the antagonist effect.

Bivalent receptor-based traps/neutralizers that antagonize multimeric ligand activity have the potential to act as therapeutic or diagnostic (imaging or non-imaging) agents for diseases/disorders caused by over-production/activity of the target ligand. It has been demonstrated that non-covalent dimerization of TβRII-ED (for example, via fusion to heterodimerizing coil strands (coiled-coil TβRII-ED)), greatly enhances the antagonist potency of TβRII-ED (De Crescenzo et al., 2004, J. Biol, Chem. 279: 26013).

A significant disadvantage of the coiled-coil fused dimer is that the non-covalent nature of the dimerization domain limits its potency, i.e. it dissociates at low concentrations such that a large portion of the coil-fused receptor ectodomain will be acting as a monomer rather than a dimer. Use of the Fc domain of IgG provides a covalent interaction, but at the cost of large size.

BRIEF DESCRIPTION OF THE DRAWINGS

FIG. 1A shows amino-acid sequences corresponding to intrinsically unstructured regions in the extracellular portions of select TGF-β-superfamily receptors. Residue numbering starts after signal peptide.[1] SEQ ID 2 is present in TβRII and TβRIIb but at different locations, as indicated.

FIG. 1B shows amino-acid sequences corresponding to structured ligand-binding domain regions in the extracellular portions of select TGF-β-superfamily receptors. Residue numbering starts after the signal peptide.

FIG. 2A shows examples of sequences corresponding to natural linkers of hetero-bivalent single-chain traps of the present invention resulting from fusion of the entire extracellular portions of select TGF-β-superfamily receptors. Residue numbering corresponds to trap construct and starts after N-terminal tag. Fusion position is indicated by (:).

FIG. 2B shows examples of sequences corresponding to embodiments of artificial linkers for hetero-bivalent single-chain traps of the present invention at varying sequence identity to natural linker sequences. Residue numbering corresponds to single-chain trap. Changed amino-acid residues relative to natural sequence are underlined. *This linker corresponds to the (TbR-II)2 referred to in the text.

FIG. 2C shows examples of sequences corresponding to varying the linker length for embodiments of hetero-bivalent single-chain traps of the present invention by deleting or repeating of natural sequences, or by inserting of artificial sequences, into the natural linker sequence. Residue numbering corresponds to trap construct and starts after N-terminal tag. Added amino-acid sequences, either natural or artificial, are underlined. Deletions are denoted by dashes. Natural linker sequences are also included as reference.

FIG. 4B shows amino-acid sequences exemplifying embodiments of hetero-valent single-chain traps (ligand binding agents) of TGF-β-superfamily growth factors, corresponding to the domain organization diagrams depicted in FIG. 4A. underlined: natural linker or sequence; underlined-italics: artificial linker; bold-italics: TbR-I-ED structured domain; bold: TbR-II-ED structured domain; regular: unstructured region of TbR-II-ED that becomes structured in the ternary complex TfβR-I/TβR-II/TGF-β [Groppe at al. 2008].

FIG. 5 shows amino-acid sequences exemplifying embodiments of hetero-bivalent single-chain traps of TGF-β-superfamily growth factors using natural linkers of varying length and composition. underlined: natural linker or sequence; bold-italics: TbR-I-ED structured domain in TbR-I/II traps and ActR-IIa structured domain in ActR-IIa/BMPR-Ia traps; bold: TbR-II-ED structured domain in TbR-I/II traps and BMPR-Ia structured domain in ActR-IIa/BMPR-Ia traps; regular: unstructured region of TbR-II-ED that becomes structured in the ternary complex TbR-I/TbR-II/TGF-b [Groppe et al. 2008].

FIG. 6 shows amino-acid sequences exemplifying embodiments of hetero-bivalent single-chain traps of TGF-β-superfamily growth factors using artificial linkers of varying length and composition, underlined: natural linker or sequence; underlined-italics: artificial linker; bold-italics: TbR-I-ED structured domain in TbR-I/II traps and ActR-IIa structured domain in ActR-IIa/BMPR-Ia traps; bold: TbR-II-ED structured domain in TbR-I/II traps and BMPR-Ia structured domain in ActR-IIa/BMPR-Ia traps; regular: unstructured region of TbR-II-ED that becomes structured in the ternary complex TbR-I/TbR-II/TGF-b [Groppe et al. 2008].

FIG. 7 shows images of feasibility studies of embodiments of hetero-bivalent trap constructs with natural linkers from three-dimensional structural models. Shown are molecular mechanics energy-minimized natural linkers for TβR-I/II-v1 and ActR-IIa/BMPR-Ia-v1 hetero-bivalent single-chain traps in complex with the TGF-β3 and BMP-2 growth factors, respectively. Each growth factor covalent dimer is rendered in gray. Each single-chain trap is rendered in black, and consists of two distinct folded binding domains and an intervening unstructured linker. Each dot indicates the point of fusion in the linker region between two distinct receptor ectodomains to generate the single-chain trap. Arrowheads indicate polypeptide chain direction in the trap's linker. Two 90°-rotated views are provided for each complex. See FIG. 5 for amino acid sequences in the structured binding domains and the intervening linker.

FIGS. 8 A and B are graphical depictions of neutralization of TGF-β1 (A) and TGF-β2 (B) by hetero-valent TβR-I/II-v1 and TβR-I/II-v2 traps. 293 cells were transfected with TβR-I/II-v1 or TβR-I/II-v2. Conditioned media (CM) was collected after 2 days. Mv1 Lu TGF-β luciferase-reporter cells were treated with 20 pM TGF-β plus various dilutions of CM and then analyzed for their luciferase levels (i.e. TGF-β-induced luciferase response). The bars show the average response levels, relative to the control CM, for each dilution (error bars=SEM for triplicate samples).

FIG. 9 shows TGF-β1 (A) and TGF-β2 (B) neutralization curves for purified single-chain TβR-I/II-v1 trap protein.

SUMMARY OF INVENTION

The invention relates to ligand binding agents capable of permitting modulation of cellular response to members of the TGF-β superfamily by binding one or more members of the TGF-β superfamily and preventing interaction with cellular receptors, and methods of designing and using such agents. The ligand binding agents taught herein are preferably single chain multivalent ligand binding agents. However, it would be possible to link such single-chain constructs to other uni- or multivalent molecules and/or to combine two or more such single chain traps using multimerization domains known in the art (e.g. coiled-coil domains, Fc domains, pentabodies) to form a multimeric trap if so desired and any such trap having a multivalent single chain portion falls within the scope of the present invention.

In an embodiment of the invention there are provided methods and processes to engineer hetero-multivalent receptor ectodomains using a single-chain approach.

The ligand binding agents of the invention are preferably hetero-multivalent ligand traps, having at least two binding domains (bd) which recognize different sites on (or the same site of different portions of) the same member of the TGF-β superfamily. The binding domains may be modified, for example to facilitate purification, so long as such modifications do not reduce binding affinity to unacceptable levels.

In an embodiment of the invention there are provided hetero-multivalent ligand traps having the general Structure I:

(<bd1>-linker1)$_k$-[{<bd1>-linker2-<bd2>-linker3$_f$-}$_n$-(<bd3>)$_m$-(linker4-<bd4>)$_d$]$_h$, where:

n and h are independently greater than or equal to 1;

d, f, m and k are independently equal to or greater than zero;

bd1, bd2, bd3 and bd4 are polypeptide binding domains independently having an affinity for a member of the TGF-β superfamily, wherein at least two of bd1, bd2, bd3, and bd4 are different from each other; such that the interface of complementary interactions with TGF-beta isoforms is increased; and, linker1, linker2, linker3 and linker4 are unstructured polypeptide sequences; wherein the number of amino acids in each linker is determined independently and is greater than or equal to X/2.5; where, X equals the shortest linear distance between:

a) the C-terminus of an isolated form of the binding domain that is located at the N-terminus of the linker and that is specifically bound to its ligand; and, b) the N-terminus of an isolated form of the binding domain that is located at the C-terminus of the linker and that is specifically bound to its ligand.

Subject to the constraints described herein, linkers 1, 2, 3, and 4 may be the same or different. In certain embodiments the linker is between 6 and 60 amino acids in length Also provided are nucleic acid sequences encoding such ligand traps.

In certain embodiments of the invention, the member of the TGF-β superfamily to which the binding domains (bd) have affinity is selected from the group consisting of: TGF-β1, TGF-β2, TGF-β3, activin βA, activin βB, activin βC, activin βE, bone morphogenic protein (BMP) 2, BMP 3, BMP4, BMP 5, BMP 6, BMP 7, BMP 8, BMP 9, BMP 10, BMP 11, BMP 12, BMP 13, BMP 14, BMP 15, growth differentiation factor (GDF) 1, GDF 3, GDF 8, GDF 9, GDF 15, Nodal, Inhibin α, anti-Mullerian Hormone, Lefty 1, Lefty 2, arteman, Persephin and Neurturin.

In an embodiment, one or more of bd1, bd2, bd3, and bd4 may be selected from SEQ ID NO 12-17.

In an embodiment of the invention the binding agent comprises one or more of SEQ ID NOs 44-64.

In an embodiment of the invention the binding agent comprises one or more of SEQ ID NO 1-11 or 18-43, 65-107, or an underlined region of one or more of SEQ ID NO 44-64 as they appear in FIGS. 4, 5 and or 6 as a linker sequence.

In an embodiment of the invention there are provided polypeptide sequences useful in binding TGF-β. In some instances, such sequences are SEQ ID NOs 44, 45 and/or 55 and/or variants thereof.

Figure 3:
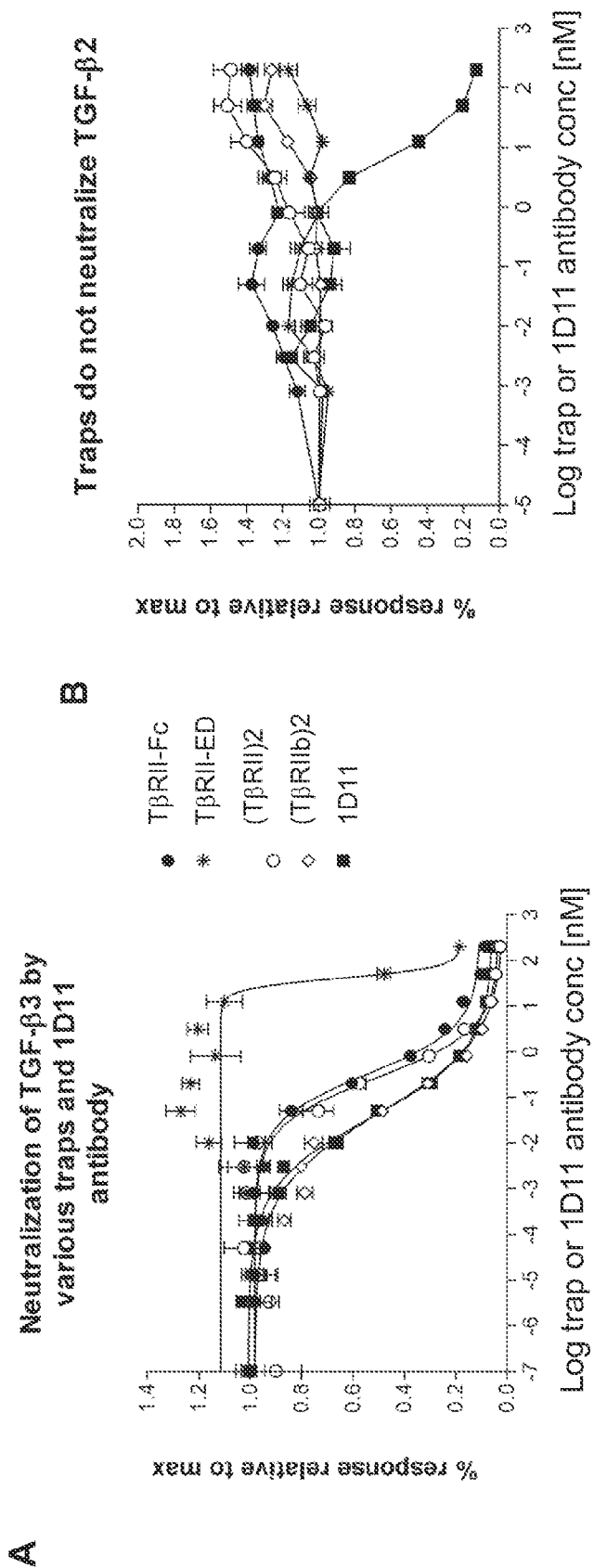
FIG. 3 shows a graphical depiction of inhibition of TGF-β3 (A) and TGF-β2 (B) signaling in Mv1Lu luciferase reporter cells by an embodiment of homo-bivalent traps (TβRII)$^2$ and (TβRIIb)$^2$ compared to TβRII-Fc, TβRII-ED monomer and pan-specific TGF-β neutralizing antibody 1D11. The homo-bivalent TGF-β traps efficiently neutralize TGF-β3 but do not neutralize TGF-β2.

In an embodiment of the invention, there are provided heterovalent TGF-β binding agents and methods for their use in modulating the response of a cell to a member of the TGF-β superfamily such as TGF-β1 and/or TGF-β2.

In an embodiment of the invention there are provided methods and uses of modelling of molecular mechanics of unstructured polypeptide sequences functioning as linkers between two binding domains having affinity for different sites on a member of the TGF-β superfamily.

The invention also provides a method of designing a hetero-multivalent binding agent useful in modulating responsiveness of a cell to a member of the TGF-β superfamily, said method com The ligand-binding agents, also referred to herein as "traps" or "ligand traps", of the present invention are multivalent as they comprise multiple binding domains (bd). The term "multivalent" includes bivalent (2 bd), trivalent (3 bd), quadruvalent (4 bd), and greater numbers of binding domains. The multivalent binding agents are heterologous ("hetero-"), as at least two binding domains are different from each other and recognize different sites on the same member of the TGF-β superfamily. or recognize different members of the TGF-β superfamily.

The hetero-multivalent binding agents of the present invention may have affinity for one or more than one member of the TGF-β superfamily. By the term "affinity", it is meant the free energy of the process of binding between the said molecules.

The term "TGF-β superfamily" refers to the family of structurally related cell regulatory proteins, of which TGF-β is a founding member. These proteins are only active as homo- or heterodimer, the two chains being linked by a single disulfide bond. Members of the TGF-β superfamily to which the binding domains (bd) have affinity may include, but are not limited to TGF-β1, TGF-β2, TGF-β3, activin βA, activin βB, activin βC, activin βE, bone morphogenic protein (BMP) 2, BMP 3, BMP4, BMP 5, BMP 6, BMP 7, BMP 8, BMP 9, BMP 10, BMP 11, BMP 12, BMP 13, BMP 14, BMP 15, growth differentiation factor (GDF) 1, GDF 3, GDF 8, GDF 9, GDF 15, Nodal, Inhibin α, anti-Mullerian Hormone, Lefty 1, Lefty 2, arteman, Persephin and Neurturin.

The binding domains in the ligand traps of the present invention may comprise any suitable polypeptide that has affinity for a member of the TGF-β superfamily. The binding domains within a hetero-multivalent trap of the present invention are independent of each other, and as such, the binding domains may have different affinities. Each binding domain region of the single-chain polypeptide may be selected for its ability to bind a growth-factor ligand having a covalently-stabilized dimeric quaternary structure; each binding domain may have affinity to one or more member of the TGF-β superfamily. The bd may be a receptor for a growth factor selected from within the TGF-β family, e.g., but not limited to transforming growth factor beta (TGF-β), bone morphogenetic protein (BMP), activin, myostatin, and including their naturally occurring isoforms.

In one example, the polypeptide binding domains may be designed based on the extracellular portion of the cognate natural receptors of the growth factors of the TGF-β superfamily. In a further example, the natural receptors from which the polypeptide binding domain is designed may be, but is not limited to TβR-I-ED, TβR-II-ED, ActR-IIa-ED, or BMPR-Ia-ED, or any other natural receptor ectodomain. In yet another non-limiting example, the binding domains may be selected from SEQ ID NOs: 12-17. As used herein "an isolated form" of a binding domain is a form of that binding domain able to act as a monovalent monomer.

The binding domains may be modified, for example to facilitate purification, so long as such modifications do not reduce binding affinity to unacceptable levels.

Within a hetero-multivalent ligand trap of the present invention, the binding domains that differ from each other will bind different sites on the one or more member of the TGF-β superfamily. In a non-limiting example, in a hetero-bivalent ligand trap, the binding domains may bind to distinct sites on each member of the TGF-β superfamily; however, the hetero-bivalent ligand trap may bind a single member of the TGF-β superfamily at any given time.

The binding domains (bd) of the ligand traps may be joined by a flexible polypeptide linker region. The linkers (1, 2, 3, and 4) in the traps of the present invention may be the same or different. The linker region provides a segment that is distinct from the structured ligand binding domains and thus can be used for conjugation to accessory molecules (for example, molecules useful in increasing stability such as PEGylation moieties) or cargo molecules such as contrast agents (for imaging) without having to chemically modify the binding domains. The linker may include an unstructured amino acid sequence that may be either the same as or derived from conservative modifications to the sequence of a natural unstructured region in the extracellular portion of the receptor for the ligand of interest or another receptor in the TGF-β superfamily. In other instances, such linkers may be entirely artificial in composition and origin but will contain amino acids selected to provide an unstructured flexible linker with a low likelihood of encountering electrostatic or steric hindrance complications when brought into close proximity to the ligand of interest.

The length of the linker is considered to be the number of amino acids between:
(a) the C-terminal main chain carbon atom of the binding domain located at the linker's N-terminal end; and
(b) the N-terminal main-chain nitrogen atom of binding domain located at the linker's C-terminal end.

Linker length will be considered acceptable when it permits binding domains located on each of the N- and C-termini of the linker to bind their natural binding sites on their natural ligand such that, with both binding domains so bound, the ligand is bound with a higher affinity than it would be bound by binding of only one of the binding domains.

In some instances, the number of amino acid residues in the linker of either natural or artificial origin is selected to be equal to or greater than the minimum required distance for simultaneous (bridged) binding to two binding sites on the target growth factor. A non-limiting example of such a determination is given in the section "Feasibility assessment procedure for designed single-chain bivalent traps". Examples of natural and artificial linker sequences of varying length are given in FIG. 2B, FIG. 2C, Table 1, FIG. 5 and FIG. 6. For example, and without wishing to be limiting in any manner, the linker length may be between about 18-80 amino acids, 25-60 amino acids, 35-45 amino acids, or any other suitable length.

In one example of the invention there is provided ligand binding agents wherein the intervening linker sequence is composed of native amino acids, the sequence of which is based on the receptor ectodomains (e.g. the various linkers shown in FIG. 2A and the "repeat" and "delete" linkers shown in FIG. 2C) or conservative substitutions of natural or unnatural amino acids into such regions, or reversal of such natural or modified sequences. It will frequently be considered preferable to use unstructured regions from these receptor ectodomains as the template for linker design. Once linkers have been designed, it will generally be preferred to test their effectiveness using the procedures described herein or other substantially functionally equivalent procedures. Routine testing for immunogenicity may be desired for in vivo use.

Non-limiting examples of useful linkers may be found in the amino acid sequences in SEQ ID NOs 1-11 and 18-43 which should be read conventionally with the N-terminus on the left and the C-terminus on the right, and in corresponding reverse sequences having the same amino acids but wherein the C-terminus is on the left and the N-terminus is on the right as the sequences are written in full. In some embodiments, such reverse sequences may be produced using D-amino acids. Where immunogencity is of concern, it may be desired to screen such reverse sequences for immunogenicity at an early stage (For examples of reverse sequences, see SEQ ID NOs: 65-107). Amino acids sequences in the present document are written N-terminus to C-terminus, unless otherwise noted. All sequences disclosed herein (except SEQ ID NO: 65-107) are disclosed as using L-amino acids; the use of a D-amino acid is considered a variant affecting the percent sequence identity to the sequences as stated.

In some instances, the linker may be independently selected to have varying degrees of sequence identity to naturally occurring unstructured amino acid sequences found in the native receptor sequence in the regions flanking the ligand binding domain, for example 70%, 80%, 90%, 95%, 98%, 99% or 100% sequence identity, whereas for entirely artificial linkers (e.g. poly-Gly or poly-Ser linkers), sequence identity will be even lower. Examples of linker sequences of varying degree of identity to the natural receptor sequence are shown in FIG. 2B, FIG. 5, and Table 1.

In addition to linkers disclosed elsewhere herein, the polypeptide sequences of Table 1 may be useful as linkers or components thereof. These polypeptides may be useful when produced using either L- or D-amino acids. However, with respect to SEQ ID NOs 65 to 107 use of D-amino acids will frequently be preferred.

TABLE 2

Non-limiting examples of linkers.

| Linker Sequence | SEQ ID NO: |
|---|---|
| PFKVAGNNDTVIMDNNVSKQVHPPI | 65 |
| DPNSTNYEES | 66 |
| PFKVAGNNDTVIMDNNIHRLPHATRNCSPCIIEDKQAEMEVDSKQVHPPI | 67 |
| TAGPLLAA | 68 |
| EVPGLGPSSKVTTP | 69 |
| ESRGLIA | 70 |
| INYYPPKPTVPNSTPQTVEME | 71 |
| TEAEGRGS | 72 |
| TPATPPPEYTVEPGGAE | 73 |
| DEPALTVGNESKKQDSDSKMGTGHLMSDLNQ | 74 |
| RISGDFFPGIVVP | 75 |
| FIINDNCEDSSCSCMFFTEGPKKKEKMICKPSAADELIFDHYPLKPDHCVTELTINEDNKRWVAVCVEQPKECISTISCNSMCSKQNDCTSFRVDCFKCLQ | 76 |
| FIINDNCEDSSCSCMFFTEGPKKKEKMICKPSAADELIFDHYPLKPDHCVTELTINEDNKRWVAVCVEQPKECISTISCNSMCSKQNDCTSFRVDCFKCLQ | 77 |
| LEIKNCHDQNCCYTTTVSGTKSSPACVFPRDRPILDIEAICMSNHIVKDTTETVSVFCLGDTVCTFNDKTCLHCFCQLA | 78 |
| PFYSFKENCMNGECCCFYVEPSDKKEVCDTRDYCNIDDLWCGQKVIEISGSINKWTAFCHRRKDKDGYCPEVGTQNTRDKEWNANFFLCEQT | 79 |
| TPATPPPEYTVEPGGAEPLHTFRENCFNGECCCFYVQPNEETAVCEQRDYCNFDDLWCGKKVLEITGSSNRWSAYCHLRKDQEGECRELGSQNTRELEWNANYYICER | 80 |
| RISGDFFPGIVVPPLTPQLYQNCLNTRCCEITRRLQAKPSDKCQFDSGEYKMCGSALTTEGQDDEEIIAFCHGNTICTNNIADDPCHGSCYCKLFPLT | 81 |

TABLE 2-continued

Non-limiting examples of linkers.

| Linker Sequence | SEQ ID NO: |
|---|---|
| PFKVAGNNDTVIMDNNVSKQVHPPIDPNSTNYEES | 82 |
| PFKVAGNNDTVIMDNNIHRLPHATRNCSPCIIEDKQAEMEVDSKQVHPPIDPNSTNYEES | 83 |
| TEAEGRGSTPATPPPEYTVEPGGAE | 84 |
| DEPALTVGNESKKQDSDSKMGTGHLMSDLNQRISGDFFPGIVVP | 85 |
| DEPALTVGNESKKQDSDSKMGTGHLMSDLNGRISGDFFPGIVVP | 86 |
| PFKVAGNNDTVIMDNNVSKQVHPPGDPNSTNYEES | 87 |
| TEAEGRGSTPATPPPEGTVEPGGAE | 88 |
| PFKVAGNNDTVIMDNNIHRLPHATRNCSPCIIEDKQAEMEVDSKQVHRGGDPNSTNYEES | 89 |
| PFKVAGNNDTVIMDNNVSKQVHPGGDPNSTNYEES | 90 |
| PFKVAGNNDTVIMDNNVSKQVHRGGDPNSTNYEES | 91 |
| PFKVAGNNDTVIMDNNIHRLPHATRNCSPCIIEDKQAEMGGGSGGGSGGGSPNSTNYEES | 92 |
| PFKVAGNNDTVIMDNNVSKGGSGGGSPNSTNYEES | 93 |
| PFKVAGNNDTVIMDGGGSGGGSGGGSPNSTNYEES | 94 |
| PFKVAGNNDTVIMDNNGGSGGGSGGGSGGGSGGGSGGGSGGGSKQVHPPIDPNSTNYEES | 95 |
| PFKVAGNNDTVIMDNNGGSGGGSGGGSGGGSGGGSGGGSGGGSGGGSGGGGDPNSTNYEES | 96 |
| PFKVAGNNDTVIMDNNVSKQVHPPIDPNSTNYEES | 97 |
| PFKVAGNNDTVIMDNNVSKQVHPPIMDNNVSKQVHPPIDPNSTNYEES | 98 |
| PFKVAGNNDTVIMDNNVSKQVHPPNSTNYEES | 99 |
| PFKVAGNNDTVIMDNNVSKQVHPPIGGGGGGGGDPNSTNYEES | 100 |
| PFKVAGNNDTVIMDNNVSKQVHPPISGGGSGGGSGGGDPNSTNYEES | 101 |
| PFKVAGNNDTVIMDNNIHRLPHATRNCSPCIIEDKQAEMEVDSKQVHPPIDPNSTNYEES | 102 |
| PFKVAGNNDTVIMDNNIHRLPHATREDKQAEMEVDSKQVHPPIDPNSTNYEES | 103 |
| TEAEGRGSTPATPPPEYTVEPGGAE | 104 |
| TEAEGRGSGGGGGGGGGGTPATPPPEYTVEPGGAE | 105 |
| DEPALTVGNESKKQDSDSKMGTGHLMSDLNQRISGDFFPGIVVP | 106 |
| DEPALTVGNESKKQDSDSKMGTGHSDLNQRISGDPGIVVP | 107 |

Also contemplated are nucleic acid sequences encoding such linkers.

In some instances, it may be desirable to subject the polypeptide-based linking design of the ligand binding agents disclosed herein to optimization of characteristics desired for a particular application. For example, the linker may be modified in length and composition based on atomic-level simulations and knowledge-based design in order to improve binding affinity, specificity, immunogenicity and stability. This is applicable to a wide range of molecular systems exhibiting homomeric, heteromeric, dimeric and multimeric ligand-receptor structural characteristics. Additional different binding domains can be incorporated to generate multivalent traps with even higher binding potency.

Linkers may be designed to facilitate purification of the linker and/or ligand binding agent. The exact purification scheme chosen will determine what modifications are needed, for example and without wishing to be limiting, additions of purification "tags" such as His tags is contemplated; in other examples, the linker may include regions to facilitate the addition of cargo or accessory molecules. When such additions affect the unstructured nature of the linker or introduce potential electrostatic or steric concerns, appropriate increases to the linker length will be made to ensure that the two binding domains are able to bind their respective sites on the ligand. In light of the methods and teachings herein, such determinations could be made routinely by one skilled in the art.

In an embodiment of the invention in which the ligand-binding domains and the linker contain primarily natural sequences they would not ordinarily be expected to be severely immunogenic or toxic in a typical patient.

The ligand binding agents of the present invention may be provided as single-chain polypeptide molecules. The fusion proteins may comprise the sequence (excluding the signal peptide) of the natural extracellular portion of one receptor repeated one or more times and the sequence (excluding the signal peptide) of the natural extracellular portion of another receptor repeated one or more times. Constructs may be provided with two or more structured domains for binding to select TGF-β-superfamily ligand(s), spaced by unstructured flexible linker(s) formed by fusing the unstructured C-terminus of one domain to the unstructured N-terminus of another domain. The natural linkers may also progressively be substituted by artificial sequences, as well as varied in length In a non-limiting example, the binding agent may comprise one or more of SEQ ID NOs: 44-64, or sequences substantially identical thereto. In a specific, non-limiting example, there is provided polypeptide sequences useful in binding TGF-β. In some instances, such sequences are SEQ ID NOs 44, 45 and/or 55, sequences substantially identical thereto, and/or variants thereof. A substantially identical peptide may comprise one or more conservative amino acid mutations. It is known in the art that one or more conservative amino acid mutations to a reference peptide may yield a mutant peptide with no substantial change in physiological, chemical, or functional properties compared to the reference peptide; in such a case, the reference and mutant peptides would be considered "substantially identical" polypeptides. Conservative amino acid mutation may include addition, deletion, or substitution of an amino acid; a conservative amino acid substitution is defined herein as the substitution of an amino acid residue for another amino acid residue with similar chemical properties (e.g. size, charge, or polarity).

In a non-limiting example, a conservative mutation may be an amino acid substitution. Such a conservative amino acid substitution may substitute a basic, neutral, hydrophobic, or acidic amino acid for another of the same group. By the term "basic amino acid" it is meant hydrophilic amino acids having a side chain pKa value of greater than 7, which are typically positively charged at physiological pH. Basic amino acids include histidine (His or H), arginine (Arg or R), and lysine (Lys or K). By the term "neutral amino acid" (also "polar amino acid"), it is meant hydrophilic amino acids having a side chain that is uncharged at physiological pH, but which has at least one bond in which the pair of electrons shared in common by two atoms is held more closely by one of the atoms. Polar amino acids include serine (Ser or S), threonine (Thr or T), cysteine (Cys or C), tyrosine (Tyr or Y), asparagine (Asn or N), and glutamine (Gln or Q). The term "hydrophobic amino acid" (also "non-polar amino acid") is meant to include amino acids exhibiting a hydrophobicity of greater than zero according to the normalized consensus hydrophobicity scale of Eisenberg (1984). Hydrophobic amino acids include proline (Pro or P), isoleucine (Ile or I), phenylalanine (Phe or F), valine (Val or V), leucine (Leu or L), tryptophan (Trp or W), methionine (Met or M), alanine (Ala or A), and glycine (Gly or G). "Acidic amino acid" refers to hydrophilic amino acids having a side chain pKa value of less than 7, which are typically negatively charged at physiological pH. Acidic amino acids include glutamate (Glu or E), and aspartate (Asp or D).

Sequence identity is used to evaluate the similarity of two sequences; it is determined by calculating the percent of residues that are the same when the two sequences are aligned for maximum correspondence between residue positions. Any known method may be used to calculate sequence identity; for example, computer software is available to calculate sequence identity. Without wishing to be limiting, sequence identity can be calculated by software such as BLAST-P, Blast-N, or FASTA-N, or any other appropriate software that is known in the art. The substantially identical sequences of the present invention may be at least 80% identical; in another example, the substantially identical sequences may be at least 80, 85, 90, 95, or 100% identical at the amino acid level to sequences described herein.

In another aspect, the ligand binding agent of the present invention may comprise the general Structure II:

<bd1>-linker2-<bd2>.

In yet another aspect of the present invention, the ligand binding agent comprises the general Structure III <bd1>-(linker2-<bd2>)$_n$.

Another aspect of the invention provides a ligand trap comprising the general Structure IV:

([bd1]-[linker1]-[bd1])$_f$-[linker2]-([bd2]-[linker3]-[bd3])$_g$, where f and g are greater than or equal to one.

In an embodiment where bd2 and bd3 are the same, and f and g are the same number, this can result in a substantially mirror symmetric structure around linker 2, subject to differences in the linkers. In instances where bd3 is different from bd2 and/or where f and g are different numbers, different structures will be produced. It is within the capacity of one of ordinary skill in the art to select suitable binding domains, linkers, and repeat frequencies in light of the disclosure herein.

In an embodiment of the invention, a non-naturally occurring single-chain hetero-bivalent polypeptide is produced by the inline fusion of two or more different structured ligand-binding domains (denoted <bd1>, <bd2>, <bd3> and <bd4>) from the extracellular portion of distinct natural receptors, and which is not fused to any dimerizing or multimerizing moieties. In some instances, this polypeptide may have the general structure <bd1>-linker2-<bd2>. In some instances, the binding domains may be selected from the ectodomains of the TβR-II and TβRI receptors, and fused to produce heterobivalent single-chain traps active against TGF-β isoforms. In other instances, the binding domains may be selected from the ectodomains of the ActR-IIa and BMPR-Ia receptors and fused to generate single-chain hetero-bivalent traps active against activin, myostatin and BMP isoforms. In other embodiments, the binding domains are selected from other receptors to members of the TGF-β superfamily.

In another embodiment of the invention a non-naturally occurring single-chain hetero-trivalent polypeptide is produced by the inline fusion of two or more different structured ligand-binding domains (denoted bd1 and bd2) from the extracellular portion of distinct natural receptors, and which is not fused to any dimerizing or multimerizing moieties. In some instances, this polypeptide may have the general structure [bd1]-linker1-[bd2]-linker2-[bd2]. In other instances, this polypeptide may have the general structure [bd1]-linker1-[bd1]-linker2-[bd2]. In some instances, [bd1] and [bd2] may be selected from the ectodomains of the TβR-II and TβRI receptors, and fused to produce hetero-bivalent single-chain traps active against TGF-β isoforms. In other instances, bd1 and bd2 may be selected from the ectodomains of the ActR-IIa and BMPR-Ia receptors and fused to generate single-chain hetero-bivalent traps active against activin, myostatin and BMP isoforms.

In another embodiment of the invention a non-naturally occurring single-chain hetero-tetravalent polypeptide is produced by the inline fusion of two or more identical or different structured ligand-binding domains from the extracellular portion of natural receptors repeated twice or more times in various orders. In an embodiment to the invention this hetero-tetravalent polypeptide is not fused to any dimerizing or multimerizing moieties. In one embodiment, this polypeptide may have the general structure [bd 1]-linker1-[bd2]-linker2-[bd1]-linker1-[bd2]. In other instances, this polypeptide may have the general structure [bd1]-linker1-[bd1]-linker2-[bd2]-linker3-[bd2]. In one embodiment, this polypeptide may have the general structure [bd1]-linker1-[bd2]-linker2-[bd2]-linker3-[bd1]. In some instances, [bd1] and [bd2] may be selected from the ectodomains of the TβR-II and TβR-I receptors, and fused to produce single-chain hetero-tetravalent traps active against TGF-β isoforms. In other instances, [bd1] and [bd2] may be selected from the ectodomains of the ActR-IIa and BMPR-Ia receptors and fused to generate single-chain hetero-tetravalent traps active against activin, myostatin and BMP isoforms.

Figure 4A:
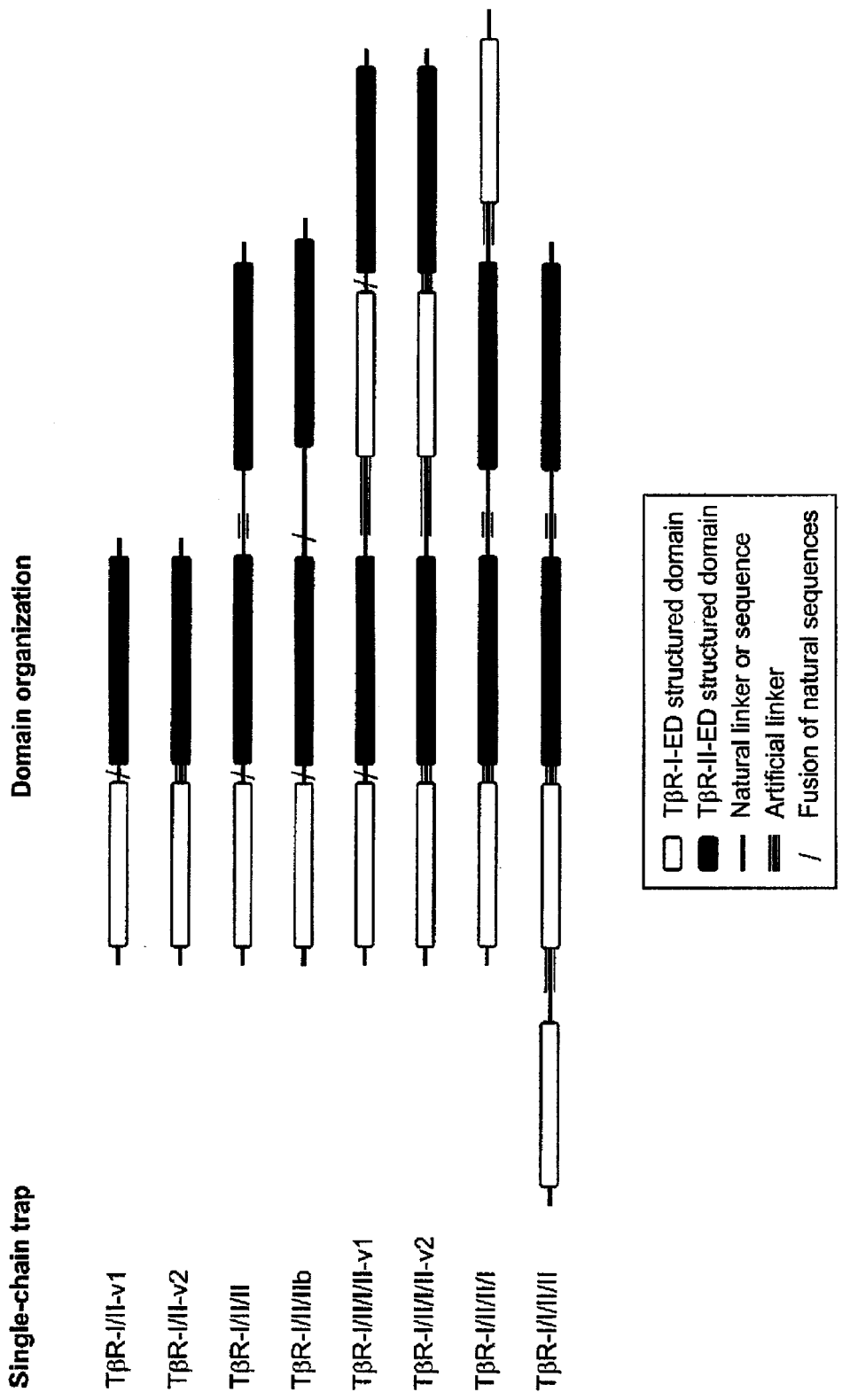
FIG. 4A provides schematic diagrams exemplifying embodiments of in-line fusions of receptor ectodomains leading to embodiments of hetero-valent single-chain traps of TGF-β-superfamily growth factors.

Specific non-limiting examples of heteromeric single-chain traps against TGF-β, and in accordance with the present invention, are represented schematically as well as with full sequence details in FIGS. 4A and 4B. FIGS. 5 and 6 provide additional examples of hetero-bivalent traps against TGF-beta and BMP based on the crystal structures of respective ternary complexes. Natural linkages between different binding domains are found in the traps listed in FIG. 5, while artificial linkages in traps are shown in FIG. 6. Molecular models of two hetero-bivalent traps with natural linkers are given in FIG. 7, one against TGF-β (TβR-II/I-v1) and one against BMP (ActR-IIa/BMPR-Ia-v1).

The overall molecular mass of bivalent ligand binding agents disclosed herein before glycosylation is between about 26 kDa and 37 kDa, and the overall mass following typical glycosylation is between about 35 kDa and 60 kDa. Many of the binding agents taught herein will have a lower molecular mass compared with competing multivalent receptor-based neutralizing agents or comparable multimeric ligand traps constructed using known multimerization domains.

TABLE 1

Example of Selected Ligand Trap Sizes

| Agent | Predicted for protein | Actual (with glycosylation) based on SDS-PAGE |
|---|---|---|
| (TβRII)$^2$ | 34 kDa | 50-60 kDa |
| (TβRIIb)$^2$ | 37 kDa | 50-60 kDa |
| (ActRIIB)$^2$ | 30 kDa | 50-60 kDa |
| (BMPR1a)$^2$ | 29 kDa | 40-50 kDa |
| RIIEcoil + RIIKcoil | | 37 Kd + 40 kDa = 77 kDa |
| TβRII-Fc | | 60 Kd + 60 kDa = 120 kDa |
| TβR-I/II-v1 | 26 kDa | 35-45 kDa |

The multivalent polypeptide ligand binding agents described herein allow for high affinity and specificity by single-chain multivalency. This single-chain attribute is fundamentally different from existing multi-chain agents such as Fc-based fusions (covalent dimer), E/K-coiled-coil-based fusions (non-covalent dimer), or described cytokines and ligand traps that include fused multimerizing moieties. Additionally, the hetero-bivalent ligand traps of the present invention have clear advantages over the molecules described in published PCT application WO 2008/113185 (O'Connor-McCourt et al). The traps of O'Connor-McCourt et at show limitation of trap affinity in some cases, and are not able to neutralize multiple TGF-β isoforms.

Without wishing to be bound by theory, TβRI/RII hetero-bivalent traps show improved binding affinity relative to either monovalent TβRII-ED or TβRI-ED traps alone due to an increase in the interface of complementary interactions with TGF-β isoforms. Pan-specific neutralization of TGF-β1, -β2, -β3 by TβRI/RII hetero-bivalent traps relative to monovalent traps is also due to this increase in affinity. That is, although the TβRI/RII hetero-bivalent traps may still bind TGF-β1 and TGF-β3 with higher affinity than TGF-β2, affinities to all TGF-β isoforms may be increased, including the TGF-β2 isoform. In the case of homo-bivalent traps like (TβRII)$^2$, the increase in affinity due to avidity does not materialize into pan-specificity because of three amino acid differences between TGF-β2 and the other isoforms that impair its high-affinity binding to TβRII (De Crescenzo et al. 2006, J. Mol. Biol. 355:47, Baardsnes et al. 2009, Biochemistry 48: 2146). The additional TβRI/TGF-β2 interface introduced by the TβRI/RII hetero-bivalent traps may improve TGF-β2 binding to a sufficient level in order to elicit TGF-β2-neutralization efficacy, not only TGF-β1 and TGF-β3 neutralization. Avidity introduced by hetero-multivalent versions may further accentuate the apparent affinity and pan-specificity. Similar deductions can be made in the case of other hetero-valent traps, such as the ActRII/BMPRIa hetero-bivalent and hetero-multivalent traps.

The present design of hetero-valent traps can facilitate tissue penetration, thereby increasing access to sites of interest. The present design can also provide a shorter half life in systemic circulation, which can be desirable for certain applications such as imaging and other diagnostic applications, as well as where ongoing abundant systemic distribution of the antagonist is not desirable. In addition, the present design permits linkage of other cargo molecules (for example imaging agents like fluorescent molecules), toxins, etc.

For example, and without wishing to be limiting in any manner, the general Structure I $$(<bd1>\text{-linker1})_k\text{-}[\{<bd1>\text{-}(\text{linker2-}<bd2>)\text{-}\\ \text{linker3}_f\}_n\text{-}(<bd3>)_m\text{-}(\text{linker4-}<bd4>)_d]_h$$

can be modified to add one or more cargo and/or accessory molecules (referred to collectively herein by $R_1$, $R_2$, $R_3$, $R_4$, etc.), to provide Structure V:

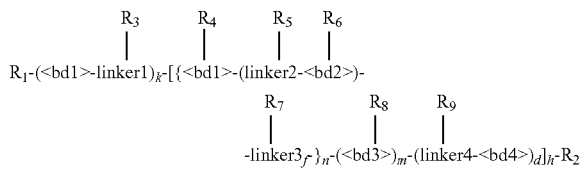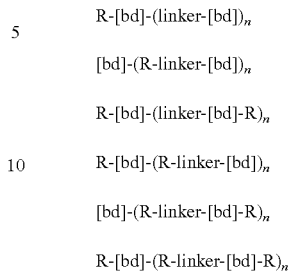

Where bd1, bd2, bd3, bd4, linker1, linker2, linker3, linker4, k, f, n, m, d, and h are defined as in Structure I.

Without limiting the generality of R substituents available, $R_1$, $R_2$, $R_3$, $R_4$, $R_5$, $R_6$, $R_7$, $R_8$, $R_9$, may or may not be present; when present, they may be the same or different, and may independently be one or more of:

- a fusion protein for targeting, for example, but not limited to such as an antibody fragment (e.g. single chain Fv) and/or a single domain antibody (sdAb);
- a radiotherapy and/or imaging agent, for example, but not limited to a radionuceotide (e.g. $^{123}$I, $^{111}$In, $^{18}$F, $^{64}$C, $^{68}$Y, $^{124}$I, $^{131}$I, $^{90}$Y, $^{177}$Lu, $^{57}$Cu, $^{213}$Bi, $^{211}$At), a fluorescent dye (e.g. Alexa Fluor, Cy dye) and/or a fluorescent protein tag (e.g. GFP, DsRed);
- a cytotoxic agent for chemotherapy, for example, but not limited to doxorubicin, calicheamicin, a maytansinoid derivatives (e.g. DM1, DM4), a toxin (eg. truncated Pseudomonas endotoxin A, diphteria toxin);
- a nanoparticle-based carrier, for example, but not limited to polyethylene glycol (PEG), a polymer-conjugated to drug, nanocarrier or imaging agent (e.g. of a polymer N-(2-hydorxylpropyl)methacrylamide (HPMA), glutamic acid, PEG, dextran);
- a drug (for example, but not limited to doxorubicin, camptothecin, paclitaxel, palatinate);
- a nanocarrier, for example, but not limited to a nanoshell or liposome;
- an imaging agent, for example, but not limited to Supermagnetic Iron Oxide (SPIO);
- a dendrimer; and/or
- a solid support for use in ligand purification, concentration or sequestration (e.g. nanoparticles, inert resins, suitable silica supports).

In general, it will not be preferable to have cargo or accessory molecules in all possible positions, as this may cause steric or electrostatic complications. However, the effects of adding a cargo or accessory molecule to any given position or positions on the structure can be determined routinely in light of the disclosure herein by modeling the linker between the binding domains and carrying out molecular dynamics simulations to substantially minimize molecular mechanics energy and reduce steric and electrostatic incompatibility between the linker and the member of the TGF-β superfamily as taught herein.

It will frequently be preferable to add the cargo or accessory molecule to the linker portion of the agent, rather to the binding domain, to reduce the likelihood of interference in binding function. However, addition to the binding domain is possible and could be desirable in some instances and the effect of such an addition can be determined routinely in advance by modeling the binding agent and the linker with the proposed addition as described herein.

In certain embodiments of conjugation to cargo molecules and accessory molecules, the following structures will be produced:

R-[bd]-(linker-[bd])$_n$

[bd]-(R-linker-[bd])$_n$

R-[bd]-(linker-[bd]-R)$_n$

R-[bd]-(R-linker-[bd])$_n$

[bd]-(R-linker-[bd]-R)$_n$

R-[bd]-(R-linker-[bd]-R)$_n$

Conjugation methodologies are somewhat diverse, but typically can be performed using commercial kits that enable conjugation via common reactive groups such as primary amines, succinimidyl (NHS) esters and sulfhydral-reactive groups. Some non-limiting examples are: Alexa Fluor 488 protein labeling kit (Molecular Probes, Invitrogen detection technologies) and PEGylation kits (Pierce Biotechnology Inc.).

In some instances, the polypeptide may be designed to bind simultaneously to equivalent but spatially distinct sites on a multimeric ligand. As used herein "multimeric" includes dimeric, trimeric, and greater numbers of units, and "multivalent" includes bivalent, trivalent, and greater numbers of binding domains.

Polypeptides of the invention can be useful as therapeutic agents that neutralize the action of disease-associated covalently-stabilized dimeric ligands such as growth factors. They may also have commercial potential for use as diagnostic agents to detect the presence of disease-associated covalently-stabilized dimeric ligands such as growth factors in imaging and non-imaging diagnostic applications. They can also be useful in the purification and/or concentration or segregation of ligand in vitro.

The invention also provides a method of designing a hetero-multivalent binding agent useful in modulating responsiveness of a cell to a member of the TGF-β superfamily, said method comprising:

a) identifying a member of the TGF-β superfamily of interest;
b) obtaining at least two different polypeptide binding domains having affinity for different sites on the same member or for different members of the TGF-β superfamily;
c) obtaining an unstructured polypeptide linker of at least a number of amino acids equal to (X/2.5) where X equals the shortest linear distance between:
  (i) the C-terminus of an isolated form of the binding domain that is located at the N-terminus of the linker and that is specifically bound to its ligand; and,
  (ii) the N-terminus of an isolated form of the binding domain that is located at the C-terminus of the linker and that is specifically bound to its ligand; and,
d) modelling the linker between the binding domains and carrying out molecular mechanics and/or dynamics simulations to substantially minimize the interaction energy and reduce steric and electrostatic incompatibility between the linker and the member of the TGF-β superfamily.

The design method can optionally be expanded to further include a step e) of producing a fusion protein comprising the two polypeptide binding domains joined by the unstructured polypeptide linker.

The present invention also encompasses a nucleotide sequence encoding a single-chain protein produced according to the teachings herein can be cloned and inserted into any suitable vector and therefore is very amenable to production (i.e. there is no requirement for two vectors, or one vector with two promoters, to express two receptor ectodomains).

Large scale production of the hetero-valent ligand traps is an attainable goal, as high yields of 30 mg of purified protein in 500 ml in 293 cells have been obtained with similar other bivalent traps.

In some instances, it may be desirable to permit a computer or other machine capable of calculation to determine linker length according to the disclosure herein. Thus, in an embodiment of the invention there is provided a data storage medium comprising instructions for determining the minimum linker length. In an embodiment of the invention there is provided a data storage medium comprising a means for identifying acceptable minimal linker length.

The present invention will be further illustrated in the following examples. However, it is to be understood that these examples are for illustrative purposes only and should not be used to limit the scope of the present invention in any manner.

Example 1

Design Strategy of Single-Chain Traps for TGF-β-Family Ligands

1. Single-chain recombinant traps were designed against growth factors that belong to the transforming growth factor TGF-β superfamily of cysteine-knot cytokines according to SCOP (Andreeva et al., 2008, Nucl. Acid Res. 36: D419) and Pfam (Finn et al., 2006, Nucl Acid Res. 34: D247) structural classifications. More specifically, these growth factors including, for example, TGF-βs, activins and BMPs, share the same 3D architecture and form covalent disulfide-linked homodimers. The method disclosed herein is applicable to all members of the TGF-βsuperfamily, including TGF-β1, -β2, -β3; activin βA, βB, βC, βE; bone morphogenetic proteins (BMP) 2-15; growth differentiation factors (GDF) 1, 3, 8 (myostatin), 9 and 15; Nodal; Inhibin α; anti-Mullerian hormone (AMH); Lefty 1 and 2; Arteman, Persephin and Neurturin.

2. Single-chain recombinant traps against TGF-β superfamily growth-factors were designed from the extracellular portion of their cognate natural receptors. The extracellular segment of all these TGF-β superfamily receptors contain a single structured domain that belongs to the snake-toxin family according to SCOP (Andreeva at al., 2008, Nucl. Acid Res. 36: D419) and Pfam (Finn et al., 2006, Nucl Acid Res. 34: D247) structural classifications. The complete extracellular portion of these receptors typically includes unstructured segments flanking their folded ligand-binding domain. These unstructured extracellular portions were apparent from the experimentally determined 3D structures available from the PDB database (Berman et al., 2000, Nucl. Acid Res. 28: 235), e.g., crystal structures for type II TGF-β receptor ectodomain (Hart et al., 2002 Nat. Struct. Biol. 9: 203; Boesen et al., 2002, Structure 10: 913; Groppe et al., 2008, Mol. Cell 29: 157), type I TGF-β receptor ectodomain (Groppe et al., 2008, Mol. Cell 29:157), type IIa activin receptor ectodomain (Allendorph et al., 2006, Proc. Natl. Acad. Sci. USA 103: 7643), type IIb activin receptor ectodomain (Thompson at al., 2003, EMBO J. 22: 1555; Greenwald at al., 2004, Mol. Cell 15: 485), type I BMP receptor ectodomain (Kirsch et al., 2000, Nat. Struct. Biol. 7: 492), or the NMR structure of the type II TGF-β receptor ectodomain (Deep et al., 2003, Biochemistry 42: 10126)]. In the absence of experimental data, as for example in the case the extracellular region of the IIb splicing variant of the TGF-β type II receptor, unstructured extracellular segments were defined by: (i) sequence portions falling outside of the folded ligand-binding domain boundaries located by comparative analysis against structurally characterized homologs, and (ii) predictions based on knowledge-based algorithms, e.g., DISOPRED (Ward et al., 2004, J. Mol. Biol. 337: 635). Amino acid sequences corresponding to the unstructured (i.e., flexible) and structured (i.e., folded, ligand-binding domain) regions from the ectodomains of several receptors of TGF-β-superfamily growth factors, are given in FIGS. 1A and 1B, respectively.

3. Homo-bivalent single-chain recombinant traps $(T\beta R-II)^2$, $(T\beta R-IIb)^2$, $(ActR-IIb)^2$ and $(BMPR-Ia)^2$ have previously been designed, produced, and tested as described in published PCT application WO 2008/113185.

4. Heterovalent single-chain recombinant traps against TGF-β-superfamily growth factors disclosed herein were designed similarly with the homovalent single-chain traps previously disclosed (WO/2008/113185, incorporated herein by reference), based on the experimentally determined binding mode between TGF-β-family ligands and the extracellular portion of their cognate natural receptors. The ligand-receptor binding mode was provided at atomic level by the high-resolution 3D structures available for several members of the TGF-β-superfamily ligands in complex with their cognate receptor ectodomains. Specifically, ternary ligand-receptor assemblies between a particular TGF-β-superfamily growth factor and ectodomains from different receptor types have been determined for the TGF-β3, TβR-II-ED and TβR-I-ED complex (Groppe at al., 2008, Mol. Cell 29:157) and for the BMP-2, ActR-IIa-ED and BMPR-Ia-ED complex (Allendorph et al., 2006, Proc. Natl. Acad. Sci. USA 103: 7643). These structures provide the relative spatial orientation between four separate receptor ectodomain chains (molecules) binding simultaneously onto one covalently homodimerized ligand molecule, i.e., 2:2:1 high-affinity-receptonlow-affinity-receptor:ligand stoichiometry. Such structures were used as guides to design hetero-bivalent, hetero-trivalent and hetero-tetravalent single-chain traps of TGF-β-superfamily growth factors and are useful in designing single-chain traps for other suitable ligands of interest involving the TGF-β superfamily.

5. Hetero-bivalent and hetero-multivalent single-chain traps of TGF-β-family ligands were designed as unnatural fusion proteins consisting of the sequence (excluding the signal peptide) of the natural extracellular portion of one receptor repeated one or more times and the sequence (excluding the signal peptide) of the natural extracellular portion of another receptor repeated one or more times. FIG. 4 describes heterovalent single-chain traps with natural linkers for TGF-β ligands, where structured and unstructured regions are based on experimental data as presented in FIGS. 1A and 1B. This design resulted in constructs with two or more structured domains for binding to select TGF-β-superfamily ligand(s), spaced by unstructured flexible linker(s) formed by fusing the unstructured C-terminus of one domain to the unstructured N-terminus of another domain. The natural linkers can also be progressively substituted by artificial sequences as well as varied in length (FIGS. 5, 6). Hetero-multivalent designs result from appropriate assemblies of homo-bivalent and hetero-bivalent designs. From thermodynamic and kinetic considerations, it was expected that multivalent receptor ectodomains would provide increased ligand-binding affinities and slower ligand-dissociation rates relative to single-domain receptor ectodomains. In the specific case of heterovalent traps directed against TGF-β isoforms, the heterovalent design was also aimed at increasing the specificity spectrum to include all TGF-β isoforms, i.e., TGF-β2, not only TGF-β1 and TGF-β3.

Example 2

Feasibility Assessment Procedure for Designed Single-Chain Bivalent Traps

To the extent to which the structures of various TGF-β-superfamily growth factors are conserved, the structures of their cognate receptor ectodomains are conserved, and the 2:1 receptor-ligand binding stoichiometry is conserved, the concept of fusing two natural receptor ectodomain sequences to produce single-chain hetero-bivalent traps with improved in vitro ligand binding affinity and ligand neutralizing activity relative to respective monovalent receptor ectodomains is applicable to the entire family of TGF-β ligands. The feasibility of these ligand traps can be theoretically assessed routinely by following the stepwise procedure outlined below. Although the procedure is presented for hetero-bivalent single-chain traps, it also applies to other designs, e.g., hetero-multivalent single-chain traps (disclosed herein).

1. The linear distance is measured between the C-terminal main-chain carbon atom of one domain and the N-terminal main-chain nitrogen atom of the other domain when bound to the covalently-dimerized ligand. Alternate structures of the complex reflecting internal geometrical flexibility in the homodimerization mode of the disulfide-stabilized ligand when bound to the receptor ectodomains can be included in the design process. A computer hardware equipped with commercial/public software appropriate for manipulating molecular structures on an available graphics device can be routinely employed to this end.

2. The linear distance (in Å units, 1 Å=$10^{-10}$ m) is divided by a factor of 2.5 to calculate the minimum number of amino acid residues that the flexible linker should posses (Table 3) in order to allow simultaneous binding of the folded domains to their binding sites on the homodimeric ligand. The 2.5 factor is based on the Cα-Cq extent of fully extended linkers, which peaks at 3.0 Å (George and Hering a, 2002, Protein Eng. 15: 871), minus an average tolerance of 0.5 Å per amino acid residue to allow for deviations of the linker path from linearity.

3. The number of amino acid residues in the unstructured linker portion of the hetero-bivalent single-chain trap should be at least equal to the estimated minimum number of linker residues required. Receptor isoforms that differ in the length of the extracellular unstructured segments, such as the TGF-β receptor isoforms II and IIb (FIG. 2A), can be included in the design process. The natural sequence-based linker can also be shortened up to the estimated minimum number of amino acid residues without significantly impairing the ligand binding affinity and neutralizing activity of the trap. A preferable location for shortening the unstructured linker is from the point of in either or both directions relative to the amino acid sequence, as exemplified by TbR-I/II-v1, -v1a, -v1b constructs for TGF-b traps and ActR-IIa/BMPR-Ia-v1, -v1a, -v1b constructs for BMP-2 traps (Table 3, FIG. 5). Example of shortened natural linkers that can be utilized in single-chain trap design are given in FIG. 2C.

As listed in Table 3, the required minimal length of the linker varies between various single-chain traps of TGF-β-superfamily growth factors. An upper limit for the length of the unstructured linker is not defined. Hence, ligand binding agent (trap) constructs with linkers comprising unstructured sequence segments repeated in whole or in part are envisioned to comply with bivalent design and preserve the desired characteristics of the trap. The natural linker can be progressively substituted by artificial sequences, which may or may not result in different linker lengths. Examples of linkers longer than the natural linker designed by repeating of natural sequence or by introducing of artificial sequence are given in FIG. 2D. Examples of introducing of artificial sequences as linkers in the design of hetero-bivalent traps are given in FIG. 6.

4. Finally, atomic-level theoretical analysis is to be carried out, where the linker is modeled between the structured domains and the molecular structure of the trap-ligand complex is refined by minimizing the molecular mechanics energy and by carrying out molecular dynamics simulations (Cornell et al., 1995, J. Am. Chem. Soc. 117: 5179). This may, in some cases, highlight regions of steric and/or electrostatic incompatibility between the trap's linker and the growth-

TABLE 3

Linker characteristics for select examples of hetero-bivalent single-chain traps of TGF-β-family growth factors.

| Single-chain trap | Targeted ligand(s) | Receptor ectodomain used | Reference structures (PDB entries) | Residues in "natural" linker | Linear distance (Å) for linkage | Minimum residues required for linkage[(a)] |
|---|---|---|---|---|---|---|
| TβR-I/II-v1 | TGF-β1<br>TGF-β2<br>TGF-β3 | TβR-I-ED,<br>TβR-II-ED | 2PJY | 7 | 14 | 6 |
| TβR-I/II-v1a | TGF-β1<br>TGF-β2<br>TGF-β3 | TβR-I-ED,<br>TβR-II-ED | 2PJY | 8 | 14 | 6 |
| TβR-I/II-v1b | TGF-β1<br>TGF-β2<br>TGF-β3 | TβR-I-ED,<br>TβR-II-ED | 2PJY | 9 | 14 | 6 |
| ActR-IIa/BMPR-Ia-v1 | BMP-2 | ActR-IIa-ED, BMPR-Ia | 2GOO | 24 | 55 | 22 |
| ActR-IIa/BMPR-Ia-v1a | BMP-2 | ActR-IIa-ED, BMPR-Ia | 2GOO | 26 | 55 | 22 |
| ActR-IIa/BMPR-Ia-v1b | BMP-2 | ActR-IIa-ED, BMPR-Ia | 2GOO | 33 | 55 | 22 |

[(a)]Minimum number of residues required for linkage represents the structure-based linear distance for linkage (Å) divided by a factor of 2.5.

factor, and suggest that the length and/or composition of the linker may be incompatible with the bivalent design, even if the linker complies with the minimum number of amino acids requirement as per step (3.) above. If the linker can be accommodated without affecting the simultaneous binding of the structured domains to their binding sites on the ligand, then the trap construct is deemed feasible for the proposed application. Computer hardware equipped with commercial/public software appropriate for manipulating molecular structures on an available graphics device, and for performing energy calculation and simulation based on molecular mechanics force fields, e.g., the AMBER force field (Cornell et al., 1995, J. Am. Chem. Soc. 117: 5179), can be routinely employed by one skilled in the art in order to carry out this structural modeling analysis. Examples of molecular mechanics energy-refined models of two single-chain hetero-bivalent traps, TβR-I/II-v1 and ActR-IIa/BMPR-Ia-v1, bound to their respective growth factors are shown in FIG. 7. These atomic-level models indicate the steric and electrostatic compatibility of the designed linker in the trap-ligand complex. These models also represent starting points for further computer-based optimization of linker composition and length. More detailed atomic-level solution structure based on molecular dynamics simulations ca be carried out routinely to further characterize the binding mode of these and other constructs, as exemplified for the homo-bivalent traps disclosed previously (WO/2008/113185).

Example 3

Demonstration that Shale-Chain Homobivalent Traps (TβRII)$^2$ and (TβRIIb)2 are Potent Neutralizers of TGF-β1 and TGF-β3 but not TGF-β2

Homo-bivalent single-chain recombinant traps (TβRII)$^2$ and (TβRIIb)$^2$ were prepared as previously described in published PCT application WO 2008/113185. The ability of purified (TβRII)$^2$ to neutralize TGF-β was tested on Mv1Lu cells having a TGF-β-responsive luciferase reporter gene and compared with TβRII-ED monomer, TβRII-Fc, and pan-specific TGF-β neutralizing antibody 1 D11 (FIG. 3). The resulting inhibition curves (FIGS. 3A and 3B, and data not shown) allowed determination of the average IC$_{50}$, a measure of neutralization potency for each TGF-β isoform (summarized in Table 4). (TβRII)$^2$ and (TβRIIb)$^2$ traps were respectively ~100-fold and 1000-fold more potent than TβRII-ED for neutralizing TGF-β1 and TGF-β3. However, these homo-bivalent traps were unable to neutralize TGF-β2.

Example 4

Examples of Hetero-Bivalent TβRI/RII Traps that Pan-Specifically Neutralize TGF-β

Figure 8:
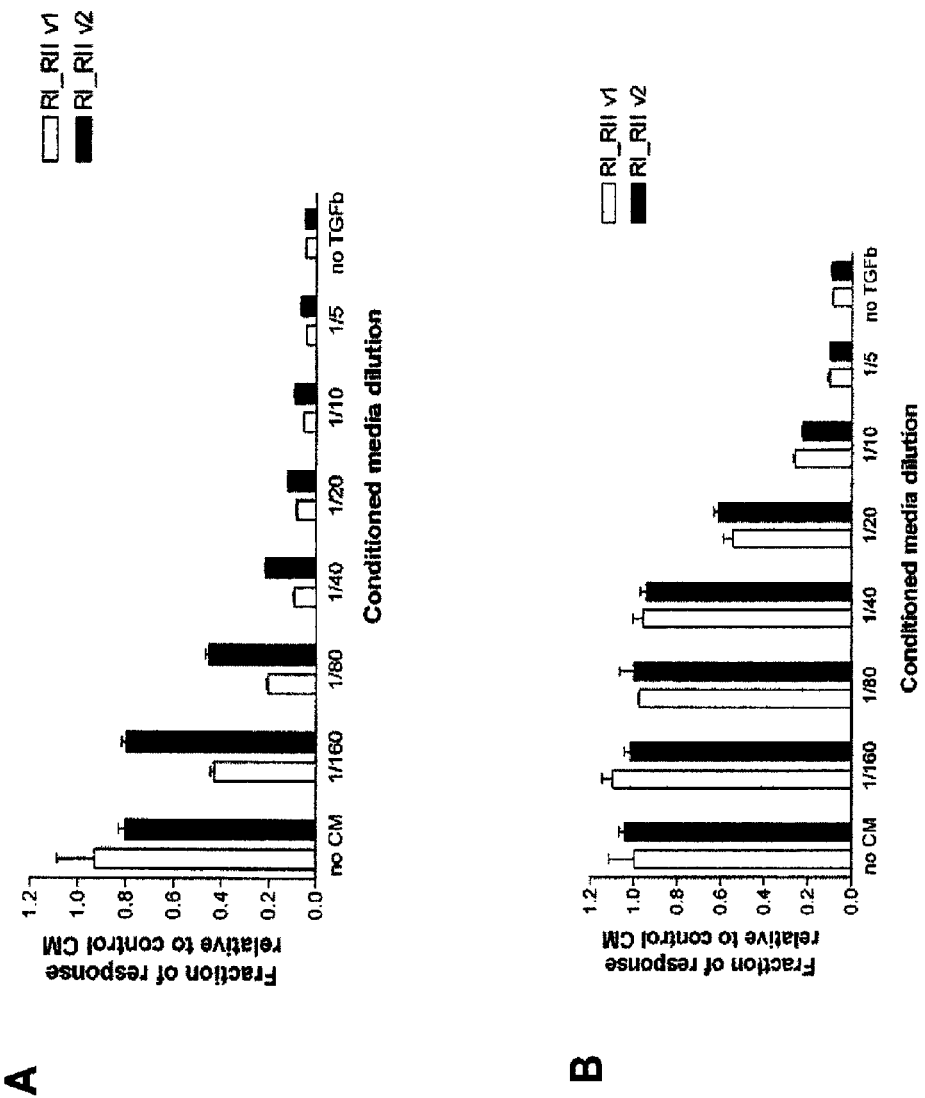

In order to assess the functionality of heterovalent single-chain traps, two hetero-bivalent trap versions depicted in FIGS. 4A and 4B, namely TβR-I/II-v1 and TβR-I/II-v2, were transiently expressed in HEK 293 cells. Conditioned media containing the secreted trap was then serially diluted and tested for neutralization of TGF-β1 or TGF-β2 using Mv1Lu luciferase reporter cells as a readout (FIGS. 8A and B). Both trap versions neutralized TGF-β1 and TGF-β2.

Construction and Cloning of Hetero-Valent TβRI/RII Traps

TβR-I/II-v1 and TβR-I/II-v2 constructs (shown in FIGS. 4A and 4B) were assembled by PCR using appropriate primers and human TβRI and TβRII template sequences and subsequently cloned into mammalian expression vector pTT2 (Durocher et al., 2002, Nucleic Acids Res. 30: E9) for transient expression in HEK293 cells or cloned into lentivirus expression vector Tet07CSII-CRS-mcs (Broussau et al, 2008, Mol. Ther. 16: 500) for transduction and stable expression in CHO cells. Each construct was preceded by the following VEGFsignal sequence/His tag/Thrombin cleavage site:

[MNFLLSWVHWSLALLLYLHHAKWSQA]APMAEGGGQNHHHHHHHGGSFNPR. (SEQ ID NO: 108)

Small-Scale Transient Transfections:

Modified human embryonic kidney cells (293-EBNA1 clone 6E) stably expressing EBNA1 were transfected using 25 kDa linear polyethylenimine (PEI) (Poysciences, Warrington, Pa.) as described below (and Durocher et al., 2002, Nucl. Acid Res. 30: e9)). The cells growing as suspension cultures in Freestyle medium (Invitrogen) were transfected at 1×10$^6$ cells/ml with a fixed amount of pTT2-trap plasmid DNA and 2 ug/ml PEI, as follows: Five hundred microliters of the suspension culture was distributed per well in a 12-well plate. DNA was diluted in Freestyle medium (in a volume equivalent to one-tenth of the culture to be transfected), PEI was added, and the mixture immediately vortexed and incubated for 10 min at room temperature prior to its addition to the cells. Following 3 h incubation with DNA-PEI complexes, culture medium was completed to 1 ml. The culture was harvested 5 days after transfection and the media was clarified by centrifugation at 3500 g for 10 min and sterile filtered. Aliquots of conditioned media were analyzed for TGF-β neutralizing activity.

TABLE 4

Trap IC$_{50}$s (nM) determined from TGF-β neutralization curves.

| Trap | IC50 for TGF-β1 | IC50 for TGF-β2 | IC50 for TGF-β3 |
|---|---|---|---|
| (TβRII)2 | 1.359 (0.459, n = 3) [a)] | No neutralization | 0.336 (0.125, n = 5) |
| (TβRIIb)2 | 0.098 (0.021, n = 4) | No neutralization | 0.045 (0.012, n = 3) |
| TβRII-Fc | 0.506 (0.506, n = 4) | No neutralization | 0.323 (0.067, n = 3) |
| TβRII-ED | >100 | No neutralization | >100 |
| 1D11 antibody | 1.429 (0.676, n = 4) | 8.674 (0.303, n = 2) | 0.029 (0.022, n = 2) |

[a)] SEM for n experiments, each performed with triplicate samples.

Figure 9:
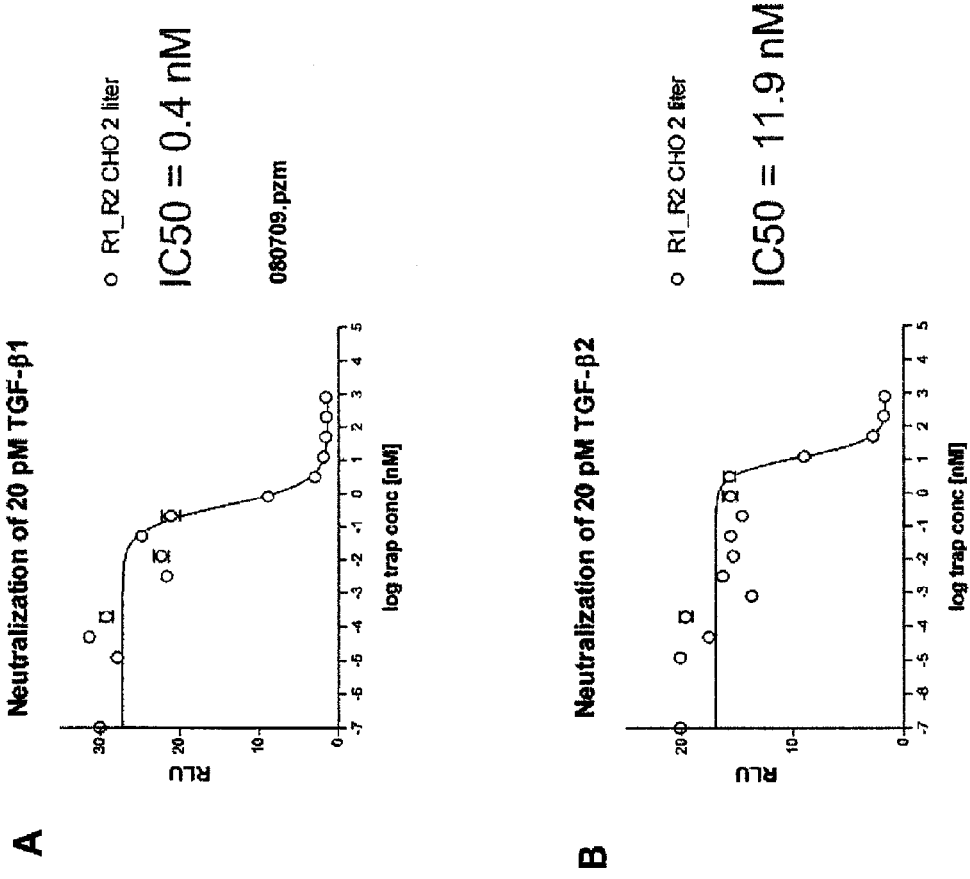

Comparison of the Antagonistic/Inhibitor Potencies of Various Binding Agents by Mv1Lu Luciferase Reporter Assays Mink lung epithelial cells, stably transfected with the TGF-β-responsive PAI-1 promoter fused to the firefly luciferase reporter gene (Abe et al., 1994, Anal. Biochem. 216: 276), were used. These cells were plated in 96-well tissue culture plates ($2\times10^4$ cells/well) in Dulbecco's modified Eagle's medium containing 5% fetal bovine serum and were allowed to attach for at least 6 h at 37° C. Cells were then washed with phosphate buffered saline (PBS), and the medium was replaced by Dulbecco's modified Eagle's medium containing 1.0% fetal bovine serum and 0.1% bovine serum albumin (DMEM-1, 0.1% BSA). Various concentrations of purified single-chain TGF-β trap, TβRII-Fc (R&D Systems), or TGF-β neutralizing antibody 1 D11 (R&D Systems) were mixed with 20 pM TGF-β in DMEM-1, 0.1% BSA and added to the cells. After 16 hr. incubation at 37° C., the medium was removed, and the cells were washed once with PBS. Cells were then lysed with 25 μl reporter lysis buffer (Promega Corp.) and assayed for luciferase activity using the Promega luciferase assay kit according to the manufacturers instructions. Luminescence was measured in a MRX (Dynex Inc.) or Lumioskan RS (Global Medical Instrumentation, Inc.) microplate reader. The activity is expressed as the percentage of the maximum TGF-β1 activity (i.e. in the absence of any antagonist) or relative luciferase units (RLU) (see examples shown in FIGS. 3, 8 and 9).

TβRI/RIIv1 Lentivirus-Transduced CHO Cell Cultures and Protein Purification:

Transduced CHO cells stably expressing TβR-I/II-v1 trap were grown in 2 liter suspension culture. The culture medium was harvested and trap protein was purified by immobilized metal affinity chromatography on Fractogel-Cobalt column as previously described (Cass et al., 2005, Protein Expr. Purl. 40: 77) except that wash and elution steps contained 25 mM and 300 mM imidazole respectively. A 10 ml column packed with 5 cm Talon Metal Affinity Resin (BD Biosciences, Mississauga, Ont.) and was equilibrated with 10 column bed volumes (CVs) of Talon Wash Buffer (TWB: 50 mM sodium phosphate, 300 mM NaCI, pH 7). The conditioned medium was passed through a 0.22 μm filter, and then loaded by gravity. The column was washed with 10 CVs of TWB and (TβRII)$^2$ was eluted in 1 ml fractions using 300 mM imidazole in TWB. Eluted trap protein was then desalted in PBS using a HiPrep 26/10 desalting column (GE-Healthcare) as recommended by the manufacturer. Protein concentration was determined by Bradford using BSA as a standard.

Example 5

Purified TβR-I/II-v1 Neutralizes Both TGF-β1 and TGF-β2

TβR-I/II-v1 was stably expressed in CHO cells; ~45 mgs trap protein was purified from a 2 liter culture. Neutralization curves determined for purified TβR-I/II-v1 indicated $IC_{50}$s of 0.4 nM and 11.9 nM for TGF-β1 and TGF-β2, respectively (FIGS. 9A and 9B). Full neutralization of both TGF-β isoforms was observed with ~200 nM trap. This proved that heterovalency improved trap affinity and potency as compared to homo-bivalent TGF-β traps for targeting multiple TGF-β isoforms.

The embodiments and examples described herein are illustrative and are not meant to limit the scope of the invention as claimed. Variations of the foregoing embodiments, including alternatives, modifications and equivalents, are intended by the inventors to be encompassed by the claims. Furthermore, the discussed combination of features might not be necessary for the inventive solution.

All documents, including patents, patent applications, journal articles, etc are incorporated herein by reference in their entirety.

We claim:

1. A hetero-multivalent binding agent with affinity for one or more than one member of the TGF-β superfamily, said agent comprising the general Structure I:

(<bd1>-linker1)$_k$-[{<bd1>-linker2-<bd2>-linker3$_f$}$_n$-(<bd3>)$_m$-(linker4-<bd4>)$_d$]$_h$, where:
n and h are independently greater than or equal to 1;
d, f, m and k are independently equal to or greater than zero;
bd1 is SEQ ID NO:14;
bd1, bd2, bd3 and bd4 are polypeptide binding domains independently having an affinity for a member of the TGF-β superfamily, wherein at least two of bd1, bd2, bd3, and bd4 are different from each other; and,
linker1, linker2, linker3 and linker4 are unstructured polypeptide sequences;
wherein the number of amino acids in each linker is determined independently and is greater than or equal to X/2.5, where X equals the shortest linear distance in Å between:
(a) the C-terminus of an isolated form of the binding domain that is located at the N-terminus of the linker and that is specifically bound to its ligand; and,
(b) the N-terminus of an isolated form of the binding domain that is located at the C-terminus of the linker and that is specifically bound to its ligand.

2. The agent of claim 1 wherein the member of the TGF-β superfamily to which the binding domains have affinity is selected from the group consisting of: TGF-β1, TGF-β2, TGF-β3, activin βA, activin βB, activin βC, activin βE, bone morphogenic protein (BMP) 2, BMP 3, BMP4, BMP 5, BMP 6, BMP 7, BMP 8, BMP 9, BMP 10, BMP 11, BMP 12, BMP 13, BMP 14, BMP 15, growth differentiation factor (GDF) 1, GDF 3, GDF 8, GDF 9, GDF 15, Nodal, Inhibin α, anti-Mullerian Hormone, Lefty 1, Lefty 2, arteman, Persephin and Neurturin.

3. The agent of claim 2 wherein the member of the TGF-β superfamily to which the binding domains have affinity is selected from the group consisting of: TGF-β1, TGF-β2, TGF-β3, BMP2, GDF 8, and activin.

4. The agent of claim 1 wherein bd4 is the same as bd1, bd2 is the same as bd3, h>0, and d, f, m, and n=1.

5. The agent of claim 1, comprising SEQ ID No 44.

6. The agent of claim 1 comprising one or more of SEQ ID NO 1-11, 18-33, 35-43, 65-75, or 82-107, or PTTVTDN-NGAVKFP (residues 88-101 of SEQ ID NO:44) as a linker sequence.

7. The agent of claim 1, wherein one or more of bd2, bd3, and bd4 is selected from one of SEQ ID NO 13-17.

8. The agent of claim 1 having the general structure V:

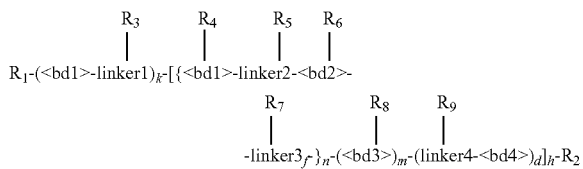

wherein $R_1$, $R_2$, $R_3$, $R_4$, $R_5$, $R_6$, $R_7$, $R_8$, and $R_9$, may be present or not, and when present, may independently be one or more of a protein for targeting, a single domain antibody, a radiotherapy agent, an imaging agent, a fluorescent dye, a fluorescent protein tag, a cytotoxic agent for chemotherapy, a nanoparticle-based carrier, a polymer conjugated to a drug, nanocarrier or imaging agent, a stabilizing agent, a drug, a nanocarrier, a support, and a dendrimer.

9. A method of modulating the response of a cell to a TGF-β superfamily member in its environment, said method comprising exposing the cell to an agent of claim 1.

10. A method of purifying or concentrating ligand comprising using the agent of claim 1 immobilized on a solid support to purify or concentrate a ligand from a sample.

11. A method of diagnosing a condition characterized in whole or part by an abnormality in levels of one or more TGF-β superfamily members in a subject, comprising administering the agent of claim 8 to the subject and detecting the presence of the agent in the body or a portion thereof of the subject.

12. A method of targeting delivery of a compound to a site of interest within the body of a subject, comprising administering an agent of claim 8 to the subject, wherein the compound is one or more of $R_1$, $R_2$, $R_3$, $R_4$, $R_5$, $R_6$, $R_7$, $R_8$, and $R_9$.

* * * * *

SEQUENCE LISTING

<160> NUMBER OF SEQ ID NOS: 108

<210> SEQ ID NO 1
<211> LENGTH: 25
<212> TYPE: PRT
<213> ORGANISM: Homo Sapiens

<400> SEQUENCE: 1

Ile Pro Pro His Val Gln Lys Ser Val Asn Asn Asp Met Ile Val Thr
1               5                   10                  15

Asp Asn Asn Gly Ala Val Lys Phe Pro
            20                  25

<210> SEQ ID NO 2
<211> LENGTH: 10
<212> TYPE: PRT
<213> ORGANISM: Homo Sapiens

<400> SEQUENCE: 2

Ser Glu Glu Tyr Asn Thr Ser Asn Pro Asp
1               5                   10

<210> SEQ ID NO 3
<211> LENGTH: 50
<212> TYPE: PRT
<213> ORGANISM: Homo Sapiens

<400> SEQUENCE: 3

Ile Pro Pro His Val Gln Lys Ser Asp Val Glu Met Glu Ala Gln Lys
1               5                   10                  15

Asp Glu Ile Ile Cys Pro Ser Cys Asn Arg Thr Ala His Pro Leu Arg
            20                  25                  30

His Ile Asn Asn Asp Met Ile Val Thr Asp Asn Asn Gly Ala Val Lys
        35                  40                  45

Phe Pro
    50

<210> SEQ ID NO 4
<211> LENGTH: 8
<212> TYPE: PRT
<213> ORGANISM: Homo Sapiens

<400> SEQUENCE: 4

Ala Ala Leu Leu Pro Gly Ala Thr
1               5

<210> SEQ ID NO 5
<211> LENGTH: 14
<212> TYPE: PRT
<213> ORGANISM: Homo Sapiens

<400> SEQUENCE: 5

Pro Thr Thr Val Lys Ser Ser Pro Gly Leu Gly Pro Val Glu
1               5                   10

<210> SEQ ID NO 6
<211> LENGTH: 7
<212> TYPE: PRT
<213> ORGANISM: Homo Sapiens

<400> SEQUENCE: 6

Ala Ile Leu Gly Arg Ser Glu
1               5

<210> SEQ ID NO 7
<211> LENGTH: 21
<212> TYPE: PRT
<213> ORGANISM: Homo Sapiens

<400> SEQUENCE: 7

Glu Met Glu Val Thr Gln Pro Thr Ser Asn Pro Val Thr Pro Lys Pro
1               5                   10                  15

Pro Tyr Tyr Asn Ile
            20

<210> SEQ ID NO 8
<211> LENGTH: 8
<212> TYPE: PRT
<213> ORGANISM: Homo Sapiens

<400> SEQUENCE: 8

Ser Gly Arg Gly Glu Ala Glu Thr
1               5

<210> SEQ ID NO 9
<211> LENGTH: 17
<212> TYPE: PRT
<213> ORGANISM: Homo Sapiens

<400> SEQUENCE: 9

```
Glu Ala Gly Gly Pro Glu Val Thr Tyr Glu Pro Pro Thr Ala Pro
1               5                   10                  15

Thr

<210> SEQ ID NO 10
<211> LENGTH: 31
<212> TYPE: PRT
<213> ORGANISM: Homo Sapiens

<400> SEQUENCE: 10

Gln Asn Leu Asp Ser Met Leu His Gly Thr Gly Met Lys Ser Asp Ser
1               5                   10                  15

Asp Gln Lys Lys Ser Glu Asn Gly Val Thr Leu Ala Pro Glu Asp
            20                  25                  30

<210> SEQ ID NO 11
<211> LENGTH: 13
<212> TYPE: PRT
<213> ORGANISM: Homo Sapiens

<400> SEQUENCE: 11

Pro Val Val Ile Gly Pro Phe Phe Asp Gly Ser Ile Arg
1               5                   10

<210> SEQ ID NO 12
<211> LENGTH: 101
<212> TYPE: PRT
<213> ORGANISM: Homo Sapiens

<400> SEQUENCE: 12

Gln Leu Cys Lys Phe Cys Asp Val Arg Phe Ser Thr Cys Asp Asn Gln
1               5                   10                  15

Lys Ser Cys Met Ser Asn Cys Ser Ile Thr Ser Ile Cys Glu Lys Pro
            20                  25                  30

Gln Glu Val Cys Val Ala Val Trp Arg Lys Asn Asp Glu Asn Ile Thr
        35                  40                  45

Leu Glu Thr Val Cys His Asp Pro Lys Leu Pro Tyr His Asp Phe Ile
    50                  55                  60

Leu Glu Asp Ala Ala Ser Pro Lys Cys Ile Met Lys Glu Lys Lys Lys
65                  70                  75                  80

Pro Gly Glu Thr Phe Phe Met Cys Ser Cys Ser Ser Asp Glu Cys Asn
                85                  90                  95

Asp Asn Ile Ile Phe
            100

<210> SEQ ID NO 13
<211> LENGTH: 101
<212> TYPE: PRT
<213> ORGANISM: Homo Sapiens

<400> SEQUENCE: 13

Gln Leu Cys Lys Phe Cys Asp Val Arg Phe Ser Thr Cys Asp Asn Gln
1               5                   10                  15

Lys Ser Cys Met Ser Asn Cys Ser Ile Thr Ser Ile Cys Glu Lys Pro
            20                  25                  30

Gln Glu Val Cys Val Ala Val Trp Arg Lys Asn Asp Glu Asn Ile Thr
        35                  40                  45

Leu Glu Thr Val Cys His Asp Pro Lys Leu Pro Tyr His Asp Phe Ile
    50                  55                  60
```

```
Leu Glu Asp Ala Ala Ser Pro Lys Cys Ile Met Lys Glu Lys Lys
 65                  70                  75                  80

Pro Gly Glu Thr Phe Phe Met Cys Ser Cys Ser Ser Asp Glu Cys Asn
                 85                  90                  95

Asp Asn Ile Ile Phe
            100

<210> SEQ ID NO 14
<211> LENGTH: 79
<212> TYPE: PRT
<213> ORGANISM: Homo Sapiens

<400> SEQUENCE: 14

Ala Leu Gln Cys Phe Cys His Leu Cys Thr Lys Asp Asn Phe Thr Cys
1               5                   10                  15

Val Thr Asp Gly Leu Cys Phe Val Ser Val Thr Glu Thr Thr Asp Lys
            20                  25                  30

Val Ile His Asn Ser Met Cys Ile Ala Glu Ile Asp Leu Ile Pro Arg
        35                  40                  45

Asp Arg Pro Phe Val Cys Ala Pro Ser Ser Lys Thr Gly Ser Val Thr
    50                  55                  60

Thr Thr Tyr Cys Cys Asn Gln Asp His Cys Asn Lys Ile Glu Leu
65                  70                  75

<210> SEQ ID NO 15
<211> LENGTH: 92
<212> TYPE: PRT
<213> ORGANISM: Homo Sapiens

<400> SEQUENCE: 15

Thr Gln Glu Cys Leu Phe Phe Asn Ala Asn Trp Glu Lys Asp Arg Thr
1               5                   10                  15

Asn Gln Thr Gly Val Glu Pro Cys Tyr Gly Asp Lys Asp Lys Arg Arg
            20                  25                  30

His Cys Phe Ala Thr Trp Lys Asn Ile Ser Gly Ser Ile Glu Ile Val
        35                  40                  45

Lys Gln Gly Cys Trp Leu Asp Asp Ile Asn Cys Tyr Asp Arg Thr Asp
    50                  55                  60

Cys Val Glu Lys Lys Asp Ser Pro Glu Val Tyr Phe Cys Cys Cys Glu
65                  70                  75                  80

Gly Asn Met Cys Asn Glu Lys Phe Ser Tyr Phe Pro
                85                  90

<210> SEQ ID NO 16
<211> LENGTH: 108
<212> TYPE: PRT
<213> ORGANISM: Homo sapiens

<400> SEQUENCE: 16

Arg Glu Cys Ile Tyr Tyr Asn Ala Asn Trp Glu Leu Glu Arg Thr Asn
1               5                   10                  15

Gln Ser Gly Leu Glu Arg Cys Glu Gly Glu Gln Asp Lys Arg Leu His
            20                  25                  30

Cys Tyr Ala Ser Trp Arg Asn Ser Ser Gly Thr Ile Glu Leu Val Lys
        35                  40                  45

Lys Gly Cys Trp Leu Asp Asp Phe Asn Cys Tyr Asp Arg Gln Glu Cys
    50                  55                  60

Val Ala Thr Glu Glu Asn Pro Gln Val Tyr Phe Cys Cys Cys Glu Gly
65                  70                  75                  80
```

Asn Phe Cys Asn Glu Arg Phe Thr His Leu Pro Glu Ala Gly Gly Pro
                85                  90                  95

Glu Val Thr Tyr Glu Pro Pro Thr Ala Pro Thr
            100                 105

<210> SEQ ID NO 17
<211> LENGTH: 98
<212> TYPE: PRT
<213> ORGANISM: Homo Sapiens

<400> SEQUENCE: 17

Thr Leu Pro Phe Leu Lys Cys Tyr Cys Ser Gly His Cys Pro Asp Asp
1               5                   10                  15

Ala Ile Asn Asn Thr Cys Ile Thr Asn Gly His Cys Phe Ala Ile Ile
            20                  25                  30

Glu Glu Asp Asp Gln Gly Glu Thr Thr Leu Ala Ser Gly Cys Met Lys
        35                  40                  45

Tyr Glu Gly Ser Asp Phe Gln Cys Lys Asp Ser Pro Lys Ala Gln Leu
    50                  55                  60

Arg Arg Thr Ile Glu Cys Cys Arg Thr Asn Leu Cys Asn Gln Tyr Leu
65                  70                  75                  80

Gln Pro Thr Leu Pro Pro Val Val Ile Gly Pro Phe Phe Asp Gly Ser
                85                  90                  95

Ile Arg

<210> SEQ ID NO 18
<211> LENGTH: 35
<212> TYPE: PRT
<213> ORGANISM: Artificial Sequence
<220> FEATURE:
<223> OTHER INFORMATION: Synthetic Polypeptide

<400> SEQUENCE: 18

Ser Glu Glu Tyr Asn Thr Ser Asn Pro Asp Ile Pro Pro His Val Gln
1               5                   10                  15

Lys Ser Val Asn Asn Asp Met Ile Val Thr Asp Asn Asn Gly Ala Val
            20                  25                  30

Lys Phe Pro
        35

<210> SEQ ID NO 19
<211> LENGTH: 60
<212> TYPE: PRT
<213> ORGANISM: Artificial sequence
<220> FEATURE:
<223> OTHER INFORMATION: synthetic polypeptide

<400> SEQUENCE: 19

Ser Glu Glu Tyr Asn Thr Ser Asn Pro Asp Ile Pro Pro His Val Gln
1               5                   10                  15

Lys Ser Asp Val Glu Met Glu Ala Gln Lys Asp Glu Ile Ile Cys Pro
            20                  25                  30

Ser Cys Asn Arg Thr Ala His Pro Leu Arg His Ile Asn Asn Asp Met
        35                  40                  45

Ile Val Thr Asp Asn Asn Gly Ala Val Lys Phe Pro
    50                  55                  60

<210> SEQ ID NO 20
<211> LENGTH: 25
<212> TYPE: PRT

```
<213> ORGANISM: Artificial Sequence
<220> FEATURE:
<223> OTHER INFORMATION: Synthetic Polypeptide

<400> SEQUENCE: 20

Glu Ala Gly Gly Pro Glu Val Thr Tyr Glu Pro Pro Thr Ala Pro
1               5                   10                  15

Thr Ser Gly Arg Gly Glu Ala Glu Thr
            20                  25

<210> SEQ ID NO 21
<211> LENGTH: 44
<212> TYPE: PRT
<213> ORGANISM: Artificial Sequence
<220> FEATURE:
<223> OTHER INFORMATION: synthetic polypeptide

<400> SEQUENCE: 21

Pro Val Val Ile Gly Pro Phe Phe Asp Gly Ser Ile Arg Gln Asn Leu
1               5                   10                  15

Asp Ser Met Leu His Gly Thr Gly Met Lys Ser Asp Ser Asp Gln Lys
            20                  25                  30

Lys Ser Glu Asn Gly Val Thr Leu Ala Pro Glu Asp
        35                  40

<210> SEQ ID NO 22
<211> LENGTH: 44
<212> TYPE: PRT
<213> ORGANISM: Artificial Sequence
<220> FEATURE:
<223> OTHER INFORMATION: Synthetic Polypeptide

<400> SEQUENCE: 22

Pro Val Val Ile Gly Pro Phe Phe Asp Gly Ser Ile Arg Gly Asn Leu
1               5                   10                  15

Asp Ser Met Leu His Gly Thr Gly Met Lys Ser Asp Ser Asp Gln Lys
            20                  25                  30

Lys Ser Glu Asn Gly Val Thr Leu Ala Pro Glu Asp
        35                  40

<210> SEQ ID NO 23
<211> LENGTH: 35
<212> TYPE: PRT
<213> ORGANISM: Artificial Sequence
<220> FEATURE:
<223> OTHER INFORMATION: Synthetic Polypeptide

<400> SEQUENCE: 23

Ser Glu Glu Tyr Asn Thr Ser Asn Pro Asp Gly Pro His Val Gln
1               5                   10                  15

Lys Ser Val Asn Asn Asp Met Ile Val Thr Asp Asn Asn Gly Ala Val
            20                  25                  30

Lys Phe Pro
        35

<210> SEQ ID NO 24
<211> LENGTH: 25
<212> TYPE: PRT
<213> ORGANISM: Artificial Sequence
<220> FEATURE:
<223> OTHER INFORMATION: Synthetic Polypeptide
```

<400> SEQUENCE: 24

Glu Ala Gly Gly Pro Glu Val Thr Gly Glu Pro Pro Thr Ala Pro
1               5                   10                  15

Thr Ser Gly Arg Gly Glu Ala Glu Thr
            20                  25

<210> SEQ ID NO 25
<211> LENGTH: 60
<212> TYPE: PRT
<213> ORGANISM: Artificial sequence
<220> FEATURE:
<223> OTHER INFORMATION: synthetic polypeptide

<400> SEQUENCE: 25

Ser Glu Glu Tyr Asn Thr Ser Asn Pro Asp Gly Gly Arg His Val Gln
1               5                   10                  15

Lys Ser Asp Val Glu Met Glu Ala Gln Lys Asp Glu Ile Ile Cys Pro
            20                  25                  30

Ser Cys Asn Arg Thr Ala His Pro Leu Arg His Ile Asn Asn Asp Met
        35                  40                  45

Ile Val Thr Asp Asn Asn Gly Ala Val Lys Phe Pro
    50                  55                  60

<210> SEQ ID NO 26
<211> LENGTH: 35
<212> TYPE: PRT
<213> ORGANISM: Artificial Sequence
<220> FEATURE:
<223> OTHER INFORMATION: Synthetic Polypeptide

<400> SEQUENCE: 26

Ser Glu Glu Tyr Asn Thr Ser Asn Pro Asp Gly Gly Pro His Val Gln
1               5                   10                  15

Lys Ser Val Asn Asn Asp Met Ile Val Thr Asp Asn Asn Gly Ala Val
            20                  25                  30

Lys Phe Pro
        35

<210> SEQ ID NO 27
<211> LENGTH: 35
<212> TYPE: PRT
<213> ORGANISM: Artificial Sequence
<220> FEATURE:
<223> OTHER INFORMATION: Synthetic Polypeptide

<400> SEQUENCE: 27

Ser Glu Glu Tyr Asn Thr Ser Asn Pro Asp Gly Gly Arg His Val Gln
1               5                   10                  15

Lys Ser Val Asn Asn Asp Met Ile Val Thr Asp Asn Asn Gly Ala Val
            20                  25                  30

Lys Phe Pro
        35

<210> SEQ ID NO 28
<211> LENGTH: 60
<212> TYPE: PRT
<213> ORGANISM: Artificial Sequence
<220> FEATURE:
<223> OTHER INFORMATION: Synthetic Polypeptide

<400> SEQUENCE: 28

Ser Glu Glu Tyr Asn Thr Ser Asn Pro Ser Gly Gly Gly Ser Gly Gly
1               5                   10                  15

Gly Ser Gly Gly Gly Met Glu Ala Gln Lys Asp Glu Ile Ile Cys Pro
                20                  25                  30

Ser Cys Asn Arg Thr Ala His Pro Leu Arg His Ile Asn Asn Asp Met
            35                  40                  45

Ile Val Thr Asp Asn Asn Gly Ala Val Lys Phe Pro
    50                  55                  60

<210> SEQ ID NO 29
<211> LENGTH: 35
<212> TYPE: PRT
<213> ORGANISM: Artificial Sequence
<220> FEATURE:
<223> OTHER INFORMATION: Synthetic Polypeptide

<400> SEQUENCE: 29

Ser Glu Glu Tyr Asn Thr Ser Asn Pro Ser Gly Gly Gly Ser Gly Gly
1               5                   10                  15

Lys Ser Val Asn Asn Asp Met Ile Val Thr Asp Asn Asn Gly Ala Val
                20                  25                  30

Lys Phe Pro
        35

<210> SEQ ID NO 30
<211> LENGTH: 35
<212> TYPE: PRT
<213> ORGANISM: Artificial Sequence
<220> FEATURE:
<223> OTHER INFORMATION: Synthetic Polypeptide

<400> SEQUENCE: 30

Ser Glu Glu Tyr Asn Thr Ser Asn Pro Ser Gly Gly Gly Ser Gly Gly
1               5                   10                  15

Gly Ser Gly Gly Gly Asp Met Ile Val Thr Asp Asn Asn Gly Ala Val
                20                  25                  30

Lys Phe Pro
        35

<210> SEQ ID NO 31
<211> LENGTH: 60
<212> TYPE: PRT
<213> ORGANISM: Artificial Sequence
<220> FEATURE:
<223> OTHER INFORMATION: Synthetic Polypeptide

<400> SEQUENCE: 31

Ser Glu Glu Tyr Asn Thr Ser Asn Pro Asp Ile Pro Pro His Val Gln
1               5                   10                  15

Lys Ser Gly Gly Gly Ser Gly Gly Ser Gly Gly Ser Gly Gly
                20                  25                  30

Gly Ser Gly Gly Gly Ser Gly Gly Ser Gly Gly Asn Asn Asp Met
            35                  40                  45

Ile Val Thr Asp Asn Asn Gly Ala Val Lys Phe Pro
    50                  55                  60

<210> SEQ ID NO 32
<211> LENGTH: 60
<212> TYPE: PRT
<213> ORGANISM: Artificial Sequence

```
<220> FEATURE:
<223> OTHER INFORMATION: Synthetic Polypeptide

<400> SEQUENCE: 32

Ser Glu Glu Tyr Asn Thr Ser Asn Pro Asp Gly Gly Ser Gly Gly
1               5                   10                  15

Gly Ser Gly Gly Gly Ser Gly Gly Gly Ser Gly Gly Gly Ser Gly Gly
            20                  25                  30

Gly Ser Gly Gly Gly Ser Gly Gly Gly Ser Gly Gly Asn Asn Asp Met
            35                  40                  45

Ile Val Thr Asp Asn Asn Gly Ala Val Lys Phe Pro
    50                  55                  60

<210> SEQ ID NO 33
<211> LENGTH: 35
<212> TYPE: PRT
<213> ORGANISM: Artificial Sequence
<220> FEATURE:
<223> OTHER INFORMATION: Synthetic Polypeptide

<400> SEQUENCE: 33

Ser Glu Glu Tyr Asn Thr Ser Asn Pro Asp Ile Pro Pro His Val Gln
1               5                   10                  15

Lys Ser Val Asn Asn Asp Met Ile Val Thr Asp Asn Asn Gly Ala Val
            20                  25                  30

Lys Phe Pro
        35

<210> SEQ ID NO 34
<211> LENGTH: 48
<212> TYPE: PRT
<213> ORGANISM: Artificial Sequence
<220> FEATURE:
<223> OTHER INFORMATION: Synthetic Polypeptide

<400> SEQUENCE: 34

Ser Glu Glu Tyr Asn Thr Ser Asn Pro Asp Ile Pro Pro His Val Gln
1               5                   10                  15

Lys Ser Val Asn Asn Asp Met Ile Pro Pro His Val Gln Lys Ser Val
            20                  25                  30

Asn Asn Asp Met Ile Val Thr Asp Asn Asn Gly Ala Val Lys Phe Pro
            35                  40                  45

<210> SEQ ID NO 35
<211> LENGTH: 32
<212> TYPE: PRT
<213> ORGANISM: Artificial Sequence
<220> FEATURE:
<223> OTHER INFORMATION: Synthetic Polypeptide

<400> SEQUENCE: 35

Ser Glu Glu Tyr Asn Thr Ser Asn Pro Pro His Val Gln Lys Ser Val
1               5                   10                  15

Asn Asn Asp Met Ile Val Thr Asp Asn Asn Gly Ala Val Lys Phe Pro
            20                  25                  30

<210> SEQ ID NO 36
<211> LENGTH: 43
<212> TYPE: PRT
<213> ORGANISM: Artificial Sequence
<220> FEATURE:
<223> OTHER INFORMATION: synthetic polypeptide

<400> SEQUENCE: 36
```

```
Ser Glu Glu Tyr Asn Thr Ser Asn Pro Asp Gly Gly Gly Gly Gly
1               5                   10                  15

Gly Gly Ile Pro Pro His Val Gln Lys Ser Val Asn Asn Asp Met Ile
            20                  25                  30

Val Thr Asp Asn Asn Gly Ala Val Lys Phe Pro
        35                  40
```

<210> SEQ ID NO 37
<211> LENGTH: 47
<212> TYPE: PRT
<213> ORGANISM: Artificial sequence
<220> FEATURE:
<223> OTHER INFORMATION: synthetic polypeptide

<400> SEQUENCE: 37

```
Ser Glu Glu Tyr Asn Thr Ser Asn Pro Asp Gly Gly Gly Ser Gly Gly
1               5                   10                  15

Gly Ser Gly Gly Gly Ser Ile Pro Pro His Val Gln Lys Ser Val Asn
            20                  25                  30

Asn Asp Met Ile Val Thr Asp Asn Asn Gly Ala Val Lys Phe Pro
        35                  40                  45
```

<210> SEQ ID NO 38
<211> LENGTH: 60
<212> TYPE: PRT
<213> ORGANISM: Artificial Sequence
<220> FEATURE:
<223> OTHER INFORMATION: Synthetic Polypeptide

<400> SEQUENCE: 38

```
Ser Glu Glu Tyr Asn Thr Ser Asn Pro Asp Ile Pro Pro His Val Gln
1               5                   10                  15

Lys Ser Asp Val Glu Met Glu Ala Gln Lys Asp Glu Ile Ile Cys Pro
            20                  25                  30

Ser Cys Asn Arg Thr Ala His Pro Leu Arg His Ile Asn Asn Asp Met
        35                  40                  45

Ile Val Thr Asp Asn Asn Gly Ala Val Lys Phe Pro
    50                  55                  60
```

<210> SEQ ID NO 39
<211> LENGTH: 53
<212> TYPE: PRT
<213> ORGANISM: Artificial Sequence
<220> FEATURE:
<223> OTHER INFORMATION: Synthetic Polypeptide

<400> SEQUENCE: 39

```
Ser Glu Glu Tyr Asn Thr Ser Asn Pro Asp Ile Pro Pro His Val Gln
1               5                   10                  15

Lys Ser Asp Val Glu Met Glu Ala Gln Lys Asp Glu Arg Thr Ala His
            20                  25                  30

Pro Leu Arg His Ile Asn Asn Asp Met Ile Val Thr Asp Asn Asn Gly
        35                  40                  45

Ala Val Lys Phe Pro
    50
```

<210> SEQ ID NO 40
<211> LENGTH: 25
<212> TYPE: PRT
<213> ORGANISM: Artificial Sequence
<220> FEATURE:
<223> OTHER INFORMATION: Synthetic Polypeptide -continued

```
<400> SEQUENCE: 40

Glu Ala Gly Gly Pro Glu Val Thr Tyr Glu Pro Pro Thr Ala Pro
1               5                   10                  15

Thr Ser Gly Arg Gly Glu Ala Glu Thr
            20                  25

<210> SEQ ID NO 41
<211> LENGTH: 35
<212> TYPE: PRT
<213> ORGANISM: Artificial Sequence
<220> FEATURE:
<223> OTHER INFORMATION: Synthetic Polypeptide

<400> SEQUENCE: 41

Glu Ala Gly Gly Pro Glu Val Thr Tyr Glu Pro Pro Thr Ala Pro
1               5                   10                  15

Thr Gly Gly Gly Gly Gly Gly Gly Gly Ser Gly Arg Gly Glu
            20                  25                  30

Ala Glu Thr
        35

<210> SEQ ID NO 42
<211> LENGTH: 44
<212> TYPE: PRT
<213> ORGANISM: Artificial Sequence
<220> FEATURE:
<223> OTHER INFORMATION: Synthetic Polypeptide

<400> SEQUENCE: 42

Pro Val Val Ile Gly Pro Phe Phe Asp Gly Ser Ile Arg Gln Asn Leu
1               5                   10                  15

Asp Ser Met Leu His Gly Thr Gly Met Lys Ser Asp Ser Asp Gln Lys
            20                  25                  30

Lys Ser Glu Asn Gly Val Thr Leu Ala Pro Glu Asp
        35                  40

<210> SEQ ID NO 43
<211> LENGTH: 40
<212> TYPE: PRT
<213> ORGANISM: Artificial Sequence
<220> FEATURE:
<223> OTHER INFORMATION: Synthetic Polypeptide

<400> SEQUENCE: 43

Pro Val Val Ile Gly Pro Asp Gly Ser Ile Arg Gln Asn Leu Asp Ser
1               5                   10                  15

His Gly Thr Gly Met Lys Ser Asp Ser Asp Gln Lys Lys Ser Glu Asn
            20                  25                  30

Gly Val Thr Leu Ala Pro Glu Asp
        35                  40

<210> SEQ ID NO 44
<211> LENGTH: 212
<212> TYPE: PRT
<213> ORGANISM: Artificial Sequence
<220> FEATURE:
<223> OTHER INFORMATION: Synthetic Polypeptide

<400> SEQUENCE: 44

Ala Ala Leu Leu Pro Gly Ala Thr Ala Leu Gln Cys Phe Cys His Leu
1               5                   10                  15

Cys Thr Lys Asp Asn Phe Thr Cys Val Thr Asp Gly Leu Cys Phe Val
```

```
            20                  25                  30
Ser Val Thr Glu Thr Thr Asp Lys Val Ile His Asn Ser Met Cys Ile
        35                  40                  45

Ala Glu Ile Asp Leu Ile Pro Arg Asp Arg Pro Phe Val Cys Ala Pro
50                  55                  60

Ser Ser Lys Thr Gly Ser Val Thr Thr Thr Tyr Cys Cys Asn Gln Asp
65                  70                  75                  80

His Cys Asn Lys Ile Glu Leu Pro Thr Thr Val Thr Asp Asn Asn Gly
                85                  90                  95

Ala Val Lys Phe Pro Gln Leu Cys Lys Phe Cys Asp Val Arg Phe Ser
            100                 105                 110

Thr Cys Asp Asn Gln Lys Ser Cys Met Ser Asn Cys Ser Ile Thr Ser
        115                 120                 125

Ile Cys Glu Lys Pro Gln Glu Val Cys Val Ala Val Trp Arg Lys Asn
130                 135                 140

Asp Glu Asn Ile Thr Leu Glu Thr Val Cys His Asp Pro Lys Leu Pro
145                 150                 155                 160

Tyr His Asp Phe Ile Leu Glu Asp Ala Ala Ser Pro Lys Cys Ile Met
                165                 170                 175

Lys Glu Lys Lys Lys Pro Gly Glu Thr Phe Phe Met Cys Ser Cys Ser
            180                 185                 190

Ser Asp Glu Cys Asn Asp Asn Ile Ile Phe Ser Glu Gly Tyr Asn Thr
        195                 200                 205

Ser Asn Pro Asp
    210

<210> SEQ ID NO 45
<211> LENGTH: 212
<212> TYPE: PRT
<213> ORGANISM: Artificial Sequence
<220> FEATURE:
<223> OTHER INFORMATION: Synthetic Polypeptide

<400> SEQUENCE: 45

Ala Ala Leu Leu Pro Gly Ala Thr Ala Leu Gln Cys Phe Cys His Leu
1               5                   10                  15

Cys Thr Lys Asp Asn Phe Thr Cys Val Thr Asp Gly Leu Cys Phe Val
            20                  25                  30

Ser Val Thr Glu Thr Thr Asp Lys Val Ile His Asn Ser Met Cys Ile
        35                  40                  45

Ala Glu Ile Asp Leu Ile Pro Arg Asp Arg Pro Phe Val Cys Ala Pro
50                  55                  60

Ser Ser Lys Thr Gly Ser Val Thr Thr Thr Tyr Cys Cys Asn Gln Asp
65                  70                  75                  80

His Cys Asn Lys Ile Glu Leu Gly Gly Gly Gly Gly Gly Asn Gly
                85                  90                  95

Ala Val Lys Phe Pro Gln Leu Cys Lys Phe Cys Asp Val Arg Phe Ser
            100                 105                 110

Thr Cys Asp Asn Gln Lys Ser Cys Met Ser Asn Cys Ser Ile Thr Ser
        115                 120                 125

Ile Cys Glu Lys Pro Gln Glu Val Cys Val Ala Val Trp Arg Lys Asn
130                 135                 140

Asp Glu Asn Ile Thr Leu Glu Thr Val Cys His Asp Pro Lys Leu Pro
145                 150                 155                 160

Tyr His Asp Phe Ile Leu Glu Asp Ala Ala Ser Pro Lys Cys Ile Met
                165                 170                 175
```

```
Lys Glu Lys Lys Lys Pro Gly Glu Thr Phe Phe Met Cys Ser Cys Ser
            180                 185                 190

Ser Asp Glu Cys Asn Asp Asn Ile Ile Phe Ser Glu Glu Tyr Asn Thr
            195                 200                 205

Ser Asn Pro Asp
    210

<210> SEQ ID NO 46
<211> LENGTH: 360
<212> TYPE: PRT
<213> ORGANISM: Artificial Sequence
<220> FEATURE:
<223> OTHER INFORMATION: Synthetic Polypeptide

<400> SEQUENCE: 46

Ala Ala Leu Leu Pro Gly Ala Thr Ala Leu Gln Cys Phe Cys His Leu
1               5                   10                  15

Cys Thr Lys Asp Asn Phe Thr Cys Val Thr Asp Gly Leu Cys Phe Val
            20                  25                  30

Ser Val Thr Glu Thr Thr Asp Lys Val Ile His Asn Ser Met Cys Ile
            35                  40                  45

Ala Glu Ile Asp Leu Ile Pro Arg Asp Arg Pro Phe Val Cys Ala Pro
        50                  55                  60

Ser Ser Lys Thr Gly Ser Val Thr Thr Thr Tyr Cys Cys Asn Gln Asp
65                  70                  75                  80

His Cys Asn Lys Ile Glu Leu Pro Thr Thr Val Thr Asp Asn Asn Gly
                85                  90                  95

Ala Val Lys Phe Pro Gln Leu Cys Lys Phe Cys Asp Val Arg Phe Ser
            100                 105                 110

Thr Cys Asp Asn Gln Lys Ser Cys Met Ser Asn Cys Ser Ile Thr Ser
            115                 120                 125

Ile Cys Glu Lys Pro Gln Glu Val Cys Val Ala Val Trp Arg Lys Asn
            130                 135                 140

Asp Glu Asn Ile Thr Leu Glu Thr Val Cys His Asp Pro Lys Leu Pro
145                 150                 155                 160

Tyr His Asp Phe Ile Leu Glu Asp Ala Ala Ser Pro Lys Cys Ile Met
                165                 170                 175

Lys Glu Lys Lys Lys Pro Gly Glu Thr Phe Phe Met Cys Ser Cys Ser
            180                 185                 190

Ser Asp Glu Cys Asn Asp Asn Ile Ile Phe Ser Glu Glu Tyr Asn Thr
            195                 200                 205

Ser Asn Pro Asp Gly Gly Gly Ser Gly Gly Gly Ser Gly Gly Gly Ser
            210                 215                 220

Ile Pro Pro His Val Gln Lys Ser Val Asn Asn Asp Met Ile Val Thr
225                 230                 235                 240

Asp Asn Asn Gly Ala Val Lys Phe Pro Gln Leu Cys Lys Phe Cys Asp
                245                 250                 255

Val Arg Phe Ser Thr Cys Asp Asn Gln Lys Ser Cys Met Ser Asn Cys
            260                 265                 270

Ser Ile Thr Ser Ile Cys Glu Lys Pro Gln Glu Val Cys Val Ala Val
            275                 280                 285

Trp Arg Lys Asn Asp Glu Asn Ile Thr Leu Glu Thr Val Cys His Asp
            290                 295                 300

Pro Lys Leu Pro Tyr His Asp Phe Ile Leu Glu Asp Ala Ala Ser Pro
305                 310                 315                 320
```

```
Lys Cys Ile Met Lys Glu Lys Lys Pro Gly Glu Thr Phe Phe Met
            325                 330                 335

Cys Ser Cys Ser Ser Asp Glu Cys Asn Asp Asn Ile Ile Phe Ser Glu
            340                 345                 350

Glu Tyr Asn Thr Ser Asn Pro Asp
        355                 360

<210> SEQ ID NO 47
<211> LENGTH: 373
<212> TYPE: PRT
<213> ORGANISM: Artificial Sequence
<220> FEATURE:
<223> OTHER INFORMATION: Synthetic Polypeptide

<400> SEQUENCE: 47

Ala Ala Leu Leu Pro Gly Ala Thr Ala Leu Gln Cys Phe Cys His Leu
1               5                   10                  15

Cys Thr Lys Asp Asn Phe Thr Cys Val Thr Asp Gly Leu Cys Phe Val
            20                  25                  30

Ser Val Thr Glu Thr Thr Asp Lys Val Ile His Asn Ser Met Cys Ile
        35                  40                  45

Ala Glu Ile Asp Leu Ile Pro Arg Asp Arg Pro Phe Val Cys Ala Pro
50                  55                  60

Ser Ser Lys Thr Gly Ser Val Thr Thr Thr Tyr Cys Cys Asn Gln Asp
65                  70                  75                  80

His Cys Asn Lys Ile Glu Leu Pro Thr Val Thr Asp Asn Asn Gly
            85                  90                  95

Ala Val Lys Phe Pro Gln Leu Cys Lys Phe Cys Asp Val Arg Phe Ser
            100                 105                 110

Thr Cys Asp Asn Gln Lys Ser Cys Met Ser Asn Cys Ser Ile Thr Ser
            115                 120                 125

Ile Cys Glu Lys Pro Gln Glu Val Cys Val Ala Val Trp Arg Lys Asn
        130                 135                 140

Asp Glu Asn Ile Thr Leu Glu Thr Val Cys His Asp Pro Lys Leu Pro
145                 150                 155                 160

Tyr His Asp Phe Ile Leu Glu Asp Ala Ala Ser Pro Lys Cys Ile Met
                165                 170                 175

Lys Glu Lys Lys Lys Pro Gly Glu Thr Phe Phe Met Cys Ser Cys Ser
            180                 185                 190

Ser Asp Glu Cys Asn Asp Asn Ile Ile Phe Ser Glu Glu Tyr Asn Thr
        195                 200                 205

Ser Asn Pro Asp Ile Pro Pro His Val Gln Lys Ser Asp Val Glu Met
210                 215                 220

Glu Ala Gln Lys Asp Glu Ile Ile Cys Pro Ser Cys Asn Arg Thr Ala
225                 230                 235                 240

His Pro Leu Arg His Ile Asn Asn Asp Met Ile Val Thr Asp Asn Asn
                245                 250                 255

Gly Ala Val Lys Phe Pro Gln Leu Cys Lys Phe Cys Asp Val Arg Phe
            260                 265                 270

Ser Thr Cys Asp Asn Gln Lys Ser Cys Met Ser Asn Cys Ser Ile Thr
        275                 280                 285

Ser Ile Cys Glu Lys Pro Gln Glu Val Cys Val Ala Val Trp Arg Lys
290                 295                 300

Asn Asp Glu Asn Ile Thr Leu Glu Thr Val Cys His Asp Pro Lys Leu
305                 310                 315                 320

Pro Tyr His Asp Phe Ile Leu Glu Asp Ala Ala Ser Pro Lys Cys Ile
```

```
                        325                 330                 335
Met Lys Glu Lys Lys Lys Pro Gly Glu Thr Phe Phe Met Cys Ser Cys
            340                 345                 350

Ser Ser Asp Glu Cys Asn Asp Asn Ile Ile Phe Ser Glu Glu Tyr Asn
            355                 360                 365

Thr Ser Asn Pro Asp
            370

<210> SEQ ID NO 48
<211> LENGTH: 448
<212> TYPE: PRT
<213> ORGANISM: Artificial Sequence
<220> FEATURE:
<223> OTHER INFORMATION: Synthetic polypeptide

<400> SEQUENCE: 48

Ala Ala Leu Leu Pro Gly Ala Thr Ala Leu Gln Cys Phe Cys His Leu
1               5                   10                  15

Cys Thr Lys Asp Asn Phe Thr Cys Val Thr Asp Gly Leu Cys Phe Val
            20                  25                  30

Ser Val Thr Glu Thr Thr Asp Lys Val Ile His Asn Ser Met Cys Ile
        35                  40                  45

Ala Glu Ile Asp Leu Ile Pro Arg Asp Arg Pro Phe Val Cys Ala Pro
    50                  55                  60

Ser Ser Lys Thr Gly Ser Val Thr Thr Thr Tyr Cys Cys Asn Gln Asp
65                  70                  75                  80

His Cys Asn Lys Ile Glu Leu Pro Thr Thr Val Thr Asn Asn Gly
                85                  90                  95

Ala Val Lys Phe Pro Gln Leu Cys Lys Phe Cys Asp Val Arg Phe Ser
            100                 105                 110

Thr Cys Asp Asn Gln Lys Ser Cys Met Ser Asn Cys Ser Ile Thr Ser
        115                 120                 125

Ile Cys Glu Lys Pro Gln Glu Val Cys Val Ala Val Trp Arg Lys Asn
    130                 135                 140

Asp Glu Asn Ile Thr Leu Glu Thr Val Cys His Asp Pro Lys Leu Pro
145                 150                 155                 160

Tyr His Asp Phe Ile Leu Glu Asp Ala Ala Ser Pro Lys Cys Ile Met
                165                 170                 175

Lys Glu Lys Lys Lys Pro Gly Glu Thr Phe Phe Met Cys Ser Cys Ser
            180                 185                 190

Ser Asp Glu Cys Asn Asp Asn Ile Ile Phe Ser Glu Glu Tyr Asn Thr
        195                 200                 205

Ser Asn Pro Asp Gly Gly Gly Ser Gly Gly Gly Ser Gly Gly Gly Ser
    210                 215                 220

Gly Gly Gly Ser Gly Gly Gly Ser Gly Gly Gly Ser Gly Gly Gly Ser
225                 230                 235                 240

Gly Gly Gly Ser Ala Leu Gln Cys Phe Cys His Leu Cys Thr Lys Asp
                245                 250                 255

Asn Phe Thr Cys Val Thr Asp Gly Leu Cys Phe Val Ser Val Thr Glu
            260                 265                 270

Thr Thr Asp Lys Val Ile His Asn Ser Met Cys Ile Ala Glu Ile Asp
        275                 280                 285

Leu Ile Pro Arg Asp Arg Pro Phe Val Cys Ala Pro Ser Ser Lys Thr
    290                 295                 300

Gly Ser Val Thr Thr Thr Tyr Cys Cys Asn Gln Asp His Cys Asn Lys
305                 310                 315                 320
```

Ile Glu Leu Pro Thr Thr Val Thr Asp Asn Asn Gly Ala Val Lys Phe
            325                 330                 335

Pro Gln Leu Cys Lys Phe Cys Asp Val Arg Phe Ser Thr Cys Asp Asn
            340                 345                 350

Gln Lys Ser Cys Met Ser Asn Cys Ser Ile Thr Ser Ile Cys Glu Lys
            355                 360                 365

Pro Gln Glu Val Cys Val Ala Val Trp Arg Lys Asn Asp Glu Asn Ile
            370                 375                 380

Thr Leu Glu Thr Val Cys His Asp Pro Lys Leu Pro Tyr His Asp Phe
385                 390                 395                 400

Ile Leu Glu Asp Ala Ala Ser Pro Lys Cys Ile Met Lys Glu Lys Lys
            405                 410                 415

Lys Pro Gly Glu Thr Phe Phe Met Cys Ser Cys Ser Ser Asp Glu Cys
            420                 425                 430

Asn Asp Asn Ile Ile Phe Ser Glu Gly Tyr Asn Thr Ser Asn Pro Asp
            435                 440                 445

<210> SEQ ID NO 49
<211> LENGTH: 448
<212> TYPE: PRT
<213> ORGANISM: Artificial Sequence
<220> FEATURE:
<223> OTHER INFORMATION: Synthetic Polypeptide

<400> SEQUENCE: 49

Ala Ala Leu Leu Pro Gly Ala Thr Ala Leu Gln Cys Phe Cys His Leu
1               5                   10                  15

Cys Thr Lys Asp Asn Phe Thr Cys Val Thr Asp Gly Leu Cys Phe Val
            20                  25                  30

Ser Val Thr Glu Thr Thr Asp Lys Val Ile His Asn Ser Met Cys Ile
            35                  40                  45

Ala Glu Ile Asp Leu Ile Pro Arg Asp Arg Pro Phe Val Cys Ala Pro
            50                  55                  60

Ser Ser Lys Thr Gly Ser Val Thr Thr Thr Tyr Cys Cys Asn Gln Asp
65                  70                  75                  80

His Cys Asn Lys Ile Glu Leu Gly Gly Gly Gly Gly Gly Gly Asn Gly
            85                  90                  95

Ala Val Lys Phe Pro Gln Leu Cys Lys Phe Cys Asp Val Arg Phe Ser
            100                 105                 110

Thr Cys Asp Asn Gln Lys Ser Cys Met Ser Asn Cys Ser Ile Thr Ser
            115                 120                 125

Ile Cys Glu Lys Pro Gln Glu Val Cys Val Ala Val Trp Arg Lys Asn
            130                 135                 140

Asp Glu Asn Ile Thr Leu Glu Thr Val Cys His Asp Pro Lys Leu Pro
145                 150                 155                 160

Tyr His Asp Phe Ile Leu Glu Asp Ala Ala Ser Pro Lys Cys Ile Met
            165                 170                 175

Lys Glu Lys Lys Lys Pro Gly Glu Thr Phe Phe Met Cys Ser Cys Ser
            180                 185                 190

Ser Asp Glu Cys Asn Asp Asn Ile Ile Phe Ser Glu Glu Tyr Asn Thr
            195                 200                 205

Ser Asn Pro Asp Gly Gly Gly Ser Gly Gly Gly Ser Gly Gly Gly Ser
            210                 215                 220

Gly Gly Gly Ser Gly Gly Gly Ser Gly Gly Gly Ser Gly Gly Gly Ser
225                 230                 235                 240

```
Gly Gly Gly Ser Ala Leu Gln Cys Phe Cys His Leu Cys Thr Lys Asp
                245                 250                 255

Asn Phe Thr Cys Val Thr Asp Gly Leu Cys Phe Val Ser Val Thr Glu
            260                 265                 270

Thr Thr Asp Lys Val Ile His Asn Ser Met Cys Ile Ala Glu Ile Asp
        275                 280                 285

Leu Ile Pro Arg Asp Arg Pro Phe Val Cys Ala Pro Ser Ser Lys Thr
    290                 295                 300

Gly Ser Val Thr Thr Thr Tyr Cys Cys Asn Gln Asp His Cys Asn Lys
305                 310                 315                 320

Ile Glu Leu Gly Gly Gly Gly Gly Gly Asn Gly Ala Val Lys Phe
                325                 330                 335

Pro Gln Leu Cys Lys Phe Cys Asp Val Arg Phe Ser Thr Cys Asp Asn
            340                 345                 350

Gln Lys Ser Cys Met Ser Asn Cys Ser Ile Thr Ser Ile Cys Glu Lys
        355                 360                 365

Pro Gln Glu Val Cys Val Ala Val Trp Arg Lys Asn Asp Glu Asn Ile
    370                 375                 380

Thr Leu Glu Thr Val Cys His Asp Pro Lys Leu Pro Tyr His Asp Phe
385                 390                 395                 400

Ile Leu Glu Asp Ala Ala Ser Pro Lys Cys Ile Met Lys Glu Lys Lys
                405                 410                 415

Lys Pro Gly Glu Thr Phe Phe Met Cys Ser Cys Ser Ser Asp Glu Cys
            420                 425                 430

Asn Asp Asn Ile Ile Phe Ser Glu Glu Tyr Asn Thr Ser Asn Pro Asp
        435                 440                 445

<210> SEQ ID NO 50
<211> LENGTH: 473
<212> TYPE: PRT
<213> ORGANISM: Artificial Sequence
<220> FEATURE:
<223> OTHER INFORMATION: Synthetic Polypeptide

<400> SEQUENCE: 50

Ala Ala Leu Leu Pro Gly Ala Thr Ala Leu Gln Cys Phe Cys His Leu
1               5                   10                  15

Cys Thr Lys Asp Asn Phe Thr Cys Val Thr Asp Gly Leu Cys Phe Val
            20                  25                  30

Ser Val Thr Glu Thr Thr Asp Lys Val Ile His Asn Ser Met Cys Ile
        35                  40                  45

Ala Glu Ile Asp Leu Ile Pro Arg Asp Arg Pro Phe Val Cys Ala Pro
    50                  55                  60

Ser Ser Lys Thr Gly Ser Val Thr Thr Thr Tyr Cys Cys Asn Gln Asp
65                  70                  75                  80

His Cys Asn Lys Ile Glu Leu Gly Gly Gly Gly Gly Gly Asn Gly
                85                  90                  95

Ala Val Lys Phe Pro Gln Leu Cys Lys Phe Cys Asp Val Arg Phe Ser
            100                 105                 110

Thr Cys Asp Asn Gln Lys Ser Cys Met Ser Asn Cys Ser Ile Thr Ser
        115                 120                 125

Ile Cys Glu Lys Pro Gln Glu Val Cys Val Ala Val Trp Arg Lys Asn
    130                 135                 140

Asp Glu Asn Ile Thr Leu Glu Thr Val Cys His Asp Pro Lys Leu Pro
145                 150                 155                 160

Tyr His Asp Phe Ile Leu Glu Asp Ala Ala Ser Pro Lys Cys Ile Met
```

165                 170                 175
Lys Glu Lys Lys Lys Pro Gly Glu Thr Phe Phe Met Cys Ser Cys Ser
            180                 185                 190

Ser Asp Glu Cys Asn Asp Asn Ile Ile Phe Ser Glu Glu Tyr Asn Thr
            195                 200                 205

Ser Asn Pro Asp Gly Gly Ser Gly Gly Ser Gly Gly Gly Ser
            210                 215                 220

Ile Pro Pro His Val Gln Lys Ser Val Asn Asn Asp Met Ile Val Thr
225                 230                 235                 240

Asp Asn Asn Gly Ala Val Lys Phe Pro Gln Leu Cys Lys Phe Cys Asp
                245                 250                 255

Val Arg Phe Ser Thr Cys Asp Asn Gln Lys Ser Cys Met Ser Asn Cys
            260                 265                 270

Ser Ile Thr Ser Ile Cys Glu Lys Pro Gln Glu Val Cys Val Ala Val
            275                 280                 285

Trp Arg Lys Asn Asp Glu Asn Ile Thr Leu Glu Thr Val Cys His Asp
            290                 295                 300

Pro Lys Leu Pro Tyr His Asp Phe Ile Leu Glu Asp Ala Ala Ser Pro
305                 310                 315                 320

Lys Cys Ile Met Lys Glu Lys Lys Pro Gly Glu Thr Phe Phe Met
                325                 330                 335

Cys Ser Cys Ser Ser Asp Glu Cys Asn Asp Asn Ile Ile Phe Ser Glu
            340                 345                 350

Glu Tyr Asn Thr Ser Asn Pro Asp Gly Gly Gly Ser Gly Gly Gly Ser
            355                 360                 365

Gly Gly Gly Ser Gly Gly Ser Gly Gly Gly Ser Ala Leu Gln Cys
        370                 375                 380

Phe Cys His Leu Cys Thr Lys Asp Asn Phe Thr Cys Val Thr Asp Gly
385                 390                 395                 400

Leu Cys Phe Val Ser Val Thr Glu Thr Thr Asp Lys Val Ile His Asn
                405                 410                 415

Ser Met Cys Ile Ala Glu Ile Asp Leu Ile Pro Arg Asp Arg Pro Phe
            420                 425                 430

Val Cys Ala Pro Ser Ser Lys Thr Gly Ser Val Thr Thr Thr Tyr Cys
            435                 440                 445

Cys Asn Gln Asp His Cys Asn Lys Ile Glu Leu Pro Thr Thr Val Lys
            450                 455                 460

Ser Ser Pro Gly Leu Gly Pro Val Glu
465                 470

<210> SEQ ID NO 51
<211> LENGTH: 473
<212> TYPE: PRT
<213> ORGANISM: Artificial Sequence
<220> FEATURE:
<223> OTHER INFORMATION: Synthetic Polypeptide

<400> SEQUENCE: 51

Ala Ala Leu Leu Pro Gly Ala Thr Ala Leu Gln Cys Phe Cys His Leu
1               5                   10                  15

Cys Thr Lys Asp Asn Phe Thr Cys Val Thr Asp Gly Leu Cys Phe Val
            20                  25                  30

Ser Val Thr Glu Thr Thr Asp Lys Val Ile His Asn Ser Met Cys Ile
        35                  40                  45

Ala Glu Ile Asp Leu Ile Pro Arg Asp Arg Pro Phe Val Cys Ala Pro
    50                  55                  60

```
Ser Ser Lys Thr Gly Ser Val Thr Thr Thr Tyr Cys Cys Asn Gln Asp
 65              70              75                  80

His Cys Asn Lys Ile Glu Leu Pro Thr Thr Val Lys Ser Ser Pro Gly
             85              90              95

Leu Gly Pro Val Glu Gly Gly Ser Gly Gly Gly Ser Gly Gly Gly
            100             105             110

Ser Gly Gly Gly Ser Gly Gly Gly Ser Ala Leu Gln Cys Phe Cys His
        115             120             125

Leu Cys Thr Lys Asp Asn Phe Thr Cys Val Thr Asp Gly Leu Cys Phe
    130             135             140

Val Ser Val Thr Glu Thr Thr Asp Lys Val Ile His Asn Ser Met Cys
145             150             155             160

Ile Ala Glu Ile Asp Leu Ile Pro Arg Asp Arg Pro Phe Val Cys Ala
                165             170             175

Pro Ser Ser Lys Thr Gly Ser Val Thr Thr Thr Tyr Cys Cys Asn Gln
            180             185             190

Asp His Cys Asn Lys Ile Glu Leu Gly Gly Gly Gly Gly Gly Asn
        195             200             205

Gly Ala Val Lys Phe Pro Gln Leu Cys Lys Phe Cys Asp Val Arg Phe
    210             215             220

Ser Thr Cys Asp Asn Gln Lys Ser Cys Met Ser Asn Cys Ser Ile Thr
225             230             235             240

Ser Ile Cys Glu Lys Pro Gln Glu Val Cys Val Ala Val Trp Arg Lys
            245             250             255

Asn Asp Glu Asn Ile Thr Leu Glu Thr Val Cys His Asp Pro Lys Leu
            260             265             270

Pro Tyr His Asp Phe Ile Leu Glu Asp Ala Ala Ser Pro Lys Cys Ile
        275             280             285

Met Lys Glu Lys Lys Lys Pro Gly Glu Thr Phe Phe Met Cys Ser Cys
    290             295             300

Ser Ser Asp Glu Cys Asn Asp Asn Ile Ile Phe Ser Glu Glu Tyr Asn
305             310             315             320

Thr Ser Asn Pro Asp Gly Gly Gly Ser Gly Gly Gly Ser Gly Gly Gly
            325             330             335

Ser Ile Pro Pro His Val Gln Lys Ser Val Asn Asn Asp Met Ile Val
        340             345             350

Thr Asp Asn Asn Gly Ala Val Lys Phe Pro Gln Leu Cys Lys Phe Cys
    355             360             365

Asp Val Arg Phe Ser Thr Cys Asp Asn Gln Lys Ser Cys Met Ser Asn
370             375             380

Cys Ser Ile Thr Ser Ile Cys Glu Lys Pro Gln Glu Val Cys Val Ala
385             390             395             400

Val Trp Arg Lys Asn Asp Glu Asn Ile Thr Leu Glu Thr Val Cys His
            405             410             415

Asp Pro Lys Leu Pro Tyr His Asp Phe Ile Leu Glu Asp Ala Ala Ser
        420             425             430

Pro Lys Cys Ile Met Lys Glu Lys Lys Lys Pro Gly Glu Thr Phe Phe
    435             440             445

Met Cys Ser Cys Ser Ser Asp Glu Cys Asn Asp Asn Ile Ile Phe Ser
    450             455             460

Glu Glu Tyr Asn Thr Ser Asn Pro Asp
465             470
```

<210> SEQ ID NO 52
<211> LENGTH: 213
<212> TYPE: PRT
<213> ORGANISM: Artificial Sequence
<220> FEATURE:
<223> OTHER INFORMATION: TbetaR-I/II-v1a

<400> SEQUENCE: 52

```
Ala Ala Leu Leu Pro Gly Ala Thr Ala Leu Gln Cys Phe Cys His Leu
1               5                   10                  15

Cys Thr Lys Asp Asn Phe Thr Cys Val Thr Asp Gly Leu Cys Phe Val
            20                  25                  30

Ser Val Thr Glu Thr Thr Asp Lys Val Ile His Asn Ser Met Cys Ile
        35                  40                  45

Ala Glu Ile Asp Leu Ile Pro Arg Asp Arg Pro Phe Val Cys Ala Pro
    50                  55                  60

Ser Ser Lys Thr Gly Ser Val Thr Thr Tyr Cys Cys Asn Gln Asp
65                  70                  75                  80

His Cys Asn Lys Ile Glu Leu Pro Thr Thr Val Val Thr Asp Asn Asn
                85                  90                  95

Gly Ala Val Lys Phe Pro Gln Leu Cys Lys Phe Cys Asp Val Arg Phe
            100                 105                 110

Ser Thr Cys Asp Asn Gln Lys Ser Cys Met Ser Asn Cys Ser Ile Thr
        115                 120                 125

Ser Ile Cys Glu Lys Pro Gln Glu Val Cys Val Ala Val Trp Arg Lys
    130                 135                 140

Asn Asp Glu Asn Ile Thr Leu Glu Thr Val Cys His Asp Pro Lys Leu
145                 150                 155                 160

Pro Tyr His Asp Phe Ile Leu Glu Asp Ala Ala Ser Pro Lys Cys Ile
                165                 170                 175

Met Lys Glu Lys Lys Lys Pro Gly Glu Thr Phe Phe Met Cys Ser Cys
            180                 185                 190

Ser Ser Asp Glu Cys Asn Asp Asn Ile Ile Phe Ser Glu Glu Tyr Asn
        195                 200                 205

Thr Ser Asn Pro Asp
    210
```

<210> SEQ ID NO 53
<211> LENGTH: 214
<212> TYPE: PRT
<213> ORGANISM: Artificial Sequence
<220> FEATURE:
<223> OTHER INFORMATION: TbetaR-I/II-v1b

<400> SEQUENCE: 53

```
Ala Ala Leu Leu Pro Gly Ala Thr Ala Leu Gln Cys Phe Cys His Leu
1               5                   10                  15

Cys Thr Lys Asp Asn Phe Thr Cys Val Thr Asp Gly Leu Cys Phe Val
            20                  25                  30

Ser Val Thr Glu Thr Thr Asp Lys Val Ile His Asn Ser Met Cys Ile
        35                  40                  45

Ala Glu Ile Asp Leu Ile Pro Arg Asp Arg Pro Phe Val Cys Ala Pro
    50                  55                  60

Ser Ser Lys Thr Gly Ser Val Thr Thr Tyr Cys Cys Asn Gln Asp
65                  70                  75                  80

His Cys Asn Lys Ile Glu Leu Pro Thr Thr Val Lys Ser Ser Pro Gly
                85                  90                  95

Asn Gly Ala Val Lys Phe Pro Gln Leu Cys Lys Phe Cys Asp Val Arg
```

```
                    100                 105                 110
Phe Ser Thr Cys Asp Asn Gln Lys Ser Met Ser Asn Cys Ser Ile
            115                 120                 125

Thr Ser Ile Cys Glu Lys Pro Gln Glu Val Cys Val Ala Val Trp Arg
130                 135                 140

Lys Asn Asp Glu Asn Ile Thr Leu Glu Thr Val Cys His Asp Pro Lys
145                 150                 155                 160

Leu Pro Tyr His Asp Phe Ile Leu Glu Asp Ala Ala Ser Pro Lys Cys
                165                 170                 175

Ile Met Lys Glu Lys Lys Lys Pro Gly Glu Thr Phe Phe Met Cys Ser
            180                 185                 190

Cys Ser Ser Asp Glu Cys Asn Asp Asn Ile Ile Phe Ser Glu Glu Tyr
            195                 200                 205

Asn Thr Ser Asn Pro Asp
    210

<210> SEQ ID NO 54
<211> LENGTH: 213
<212> TYPE: PRT
<213> ORGANISM: Artificial Sequence
<220> FEATURE:
<223> OTHER INFORMATION: TbetaR-I/II-v1c

<400> SEQUENCE: 54

Ala Ala Leu Leu Pro Gly Ala Thr Ala Leu Gln Cys Phe Cys His Leu
1               5                   10                  15

Cys Thr Lys Asp Asn Phe Thr Cys Val Thr Asp Gly Leu Cys Phe Val
            20                  25                  30

Ser Val Thr Glu Thr Thr Asp Lys Val Ile His Asn Ser Met Cys Ile
        35                  40                  45

Ala Glu Ile Asp Leu Ile Pro Arg Asp Arg Pro Phe Val Cys Ala Pro
    50                  55                  60

Ser Ser Lys Thr Gly Ser Val Thr Thr Thr Tyr Cys Cys Asn Gln Asp
65                  70                  75                  80

His Cys Asn Lys Ile Glu Leu Asn Asp Met Ile Val Thr Asp Asn Asn
                85                  90                  95

Gly Ala Val Lys Phe Pro Gln Leu Cys Lys Phe Cys Asp Val Arg Phe
            100                 105                 110

Ser Thr Cys Asp Asn Gln Lys Ser Cys Met Ser Asn Cys Ser Ile Thr
        115                 120                 125

Ser Ile Cys Glu Lys Pro Gln Glu Val Cys Val Ala Val Trp Arg Lys
    130                 135                 140

Asn Asp Glu Asn Ile Thr Leu Glu Thr Val Cys His Asp Pro Lys Leu
145                 150                 155                 160

Pro Tyr His Asp Phe Ile Leu Glu Asp Ala Ala Ser Pro Lys Cys Ile
                165                 170                 175

Met Lys Glu Lys Lys Lys Pro Gly Glu Thr Phe Phe Met Cys Ser Cys
            180                 185                 190

Ser Ser Asp Glu Cys Asn Asp Asn Ile Ile Phe Ser Glu Glu Tyr Asn
        195                 200                 205

Thr Ser Asn Pro Asp
    210

<210> SEQ ID NO 55
<211> LENGTH: 221
<212> TYPE: PRT
<213> ORGANISM: Artificial Sequence
```

```
<220> FEATURE:
<223> OTHER INFORMATION: ActR-IIa/BMPR-Ia-v1

<400> SEQUENCE: 55

Ala Ile Leu Gly Arg Ser Glu Thr Gln Glu Cys Leu Phe Phe Asn Ala
1               5                   10                  15

Asn Trp Glu Lys Asp Arg Thr Asn Gln Thr Gly Val Glu Pro Cys Tyr
            20                  25                  30

Gly Asp Lys Asp Lys Arg Arg His Cys Phe Ala Thr Trp Lys Asn Ile
        35                  40                  45

Ser Gly Ser Ile Glu Ile Val Lys Gln Gly Cys Trp Leu Asp Asp Ile
    50                  55                  60

Asn Cys Tyr Asp Arg Thr Asp Cys Val Glu Lys Lys Asp Ser Pro Glu
65                  70                  75                  80

Val Tyr Phe Cys Cys Cys Glu Gly Asn Met Cys Asn Glu Lys Phe Ser
                85                  90                  95

Tyr Phe Pro Glu Met Glu Val Thr Gln Pro Thr Ser Asp Gln Lys Lys
            100                 105                 110

Ser Glu Asn Gly Val Thr Leu Ala Pro Glu Asp Thr Leu Pro Phe Leu
        115                 120                 125

Lys Cys Tyr Cys Ser Gly His Cys Pro Asp Asp Ala Ile Asn Asn Thr
    130                 135                 140

Cys Ile Thr Asn Gly His Cys Phe Ala Ile Ile Glu Glu Asp Asp Gln
145                 150                 155                 160

Gly Glu Thr Thr Leu Ala Ser Gly Cys Met Lys Tyr Glu Gly Ser Asp
                165                 170                 175

Phe Gln Cys Lys Asp Ser Pro Lys Ala Gln Leu Arg Arg Thr Ile Glu
            180                 185                 190

Cys Cys Arg Thr Asn Leu Cys Asn Gln Tyr Leu Gln Pro Thr Leu Pro
        195                 200                 205

Pro Val Val Ile Gly Pro Phe Phe Asp Gly Ser Ile Arg
    210                 215                 220

<210> SEQ ID NO 56
<211> LENGTH: 223
<212> TYPE: PRT
<213> ORGANISM: Artificial Sequence
<220> FEATURE:
<223> OTHER INFORMATION: ActR-IIa/BMPR-Ia-v1a

<400> SEQUENCE: 56

Ala Ile Leu Gly Arg Ser Glu Thr Gln Glu Cys Leu Phe Phe Asn Ala
1               5                   10                  15

Asn Trp Glu Lys Asp Arg Thr Asn Gln Thr Gly Val Glu Pro Cys Tyr
            20                  25                  30

Gly Asp Lys Asp Lys Arg Arg His Cys Phe Ala Thr Trp Lys Asn Ile
        35                  40                  45

Ser Gly Ser Ile Glu Ile Val Lys Gln Gly Cys Trp Leu Asp Asp Ile
    50                  55                  60

Asn Cys Tyr Asp Arg Thr Asp Cys Val Glu Lys Lys Asp Ser Pro Glu
65                  70                  75                  80

Val Tyr Phe Cys Cys Cys Glu Gly Asn Met Cys Asn Glu Lys Phe Ser
                85                  90                  95

Tyr Phe Pro Glu Met Glu Val Thr Gln Pro Thr Ser Asp Ser Asp Gln
            100                 105                 110

Lys Lys Ser Glu Asn Gly Val Thr Leu Ala Pro Glu Asp Thr Leu Pro
        115                 120                 125
```

```
Phe Leu Lys Cys Tyr Cys Ser Gly His Cys Pro Asp Ala Ile Asn
    130                 135                 140

Asn Thr Cys Ile Thr Asn Gly His Cys Phe Ala Ile Ile Glu Glu Asp
145                 150                 155                 160

Asp Gln Gly Glu Thr Thr Leu Ala Ser Gly Cys Met Lys Tyr Glu Gly
                165                 170                 175

Ser Asp Phe Gln Cys Lys Asp Ser Pro Lys Ala Gln Leu Arg Arg Thr
            180                 185                 190

Ile Glu Cys Cys Arg Thr Asn Leu Cys Asn Gln Tyr Leu Gln Pro Thr
        195                 200                 205

Leu Pro Pro Val Val Ile Gly Pro Phe Phe Asp Gly Ser Ile Arg
    210                 215                 220

<210> SEQ ID NO 57
<211> LENGTH: 230
<212> TYPE: PRT
<213> ORGANISM: Artificial Sequence
<220> FEATURE:
<223> OTHER INFORMATION: ActR-IIa/BMPR-Ia-v1b

<400> SEQUENCE: 57

Ala Ile Leu Gly Arg Ser Glu Thr Gln Glu Cys Leu Phe Phe Asn Ala
1               5                   10                  15

Asn Trp Glu Lys Asp Arg Thr Asn Gln Thr Gly Val Glu Pro Cys Tyr
            20                  25                  30

Gly Asp Lys Asp Lys Arg Arg His Cys Phe Ala Thr Trp Lys Asn Ile
        35                  40                  45

Ser Gly Ser Ile Glu Ile Val Lys Gln Gly Cys Trp Leu Asp Asp Ile
50                  55                  60

Asn Cys Tyr Asp Arg Thr Asp Cys Val Glu Lys Lys Asp Ser Pro Glu
65                  70                  75                  80

Val Tyr Phe Cys Cys Cys Glu Gly Asn Met Cys Asn Glu Lys Phe Ser
                85                  90                  95

Tyr Phe Pro Glu Met Glu Val Thr Gln Pro Thr Ser Asn Pro Val Thr
            100                 105                 110

Pro Lys Ser Asp Ser Asp Gln Lys Lys Ser Glu Asn Gly Val Thr Leu
        115                 120                 125

Ala Pro Glu Asp Thr Leu Pro Phe Leu Lys Cys Tyr Cys Ser Gly His
    130                 135                 140

Cys Pro Asp Asp Ala Ile Asn Asn Thr Cys Ile Thr Asn Gly His Cys
145                 150                 155                 160

Phe Ala Ile Ile Glu Glu Asp Asp Gln Gly Glu Thr Thr Leu Ala Ser
                165                 170                 175

Gly Cys Met Lys Tyr Glu Gly Ser Asp Phe Gln Cys Lys Asp Ser Pro
            180                 185                 190

Lys Ala Gln Leu Arg Arg Thr Ile Glu Cys Cys Arg Thr Asn Leu Cys
        195                 200                 205

Asn Gln Tyr Leu Gln Pro Thr Leu Pro Pro Val Val Ile Gly Pro Phe
    210                 215                 220

Phe Asp Gly Ser Ile Arg
225                 230

<210> SEQ ID NO 58
<211> LENGTH: 231
<212> TYPE: PRT
<213> ORGANISM: Artificial Sequence
<220> FEATURE:
```

<223> OTHER INFORMATION: ActR-IIa/BMPR-Ia-v1c

<400> SEQUENCE: 58

```
Ala Ile Leu Gly Arg Ser Glu Thr Gln Glu Cys Leu Phe Phe Asn Ala
1               5                   10                  15

Asn Trp Glu Lys Asp Arg Thr Asn Gln Thr Gly Val Glu Pro Cys Tyr
            20                  25                  30

Gly Asp Lys Asp Lys Arg Arg His Cys Phe Ala Thr Trp Lys Asn Ile
        35                  40                  45

Ser Gly Ser Ile Glu Ile Val Lys Gln Gly Cys Trp Leu Asp Asp Ile
    50                  55                  60

Asn Cys Tyr Asp Arg Thr Asp Cys Val Glu Lys Lys Asp Ser Pro Glu
65                  70                  75                  80

Val Tyr Phe Cys Cys Cys Glu Gly Asn Met Cys Asn Glu Lys Phe Ser
                85                  90                  95

Tyr Phe Pro Glu Met Glu Val Thr Gln Pro Thr Ser Asn Pro Val Thr
            100                 105                 110

Gly Met Lys Ser Asp Ser Asp Gln Lys Lys Ser Glu Asn Gly Val Thr
        115                 120                 125

Leu Ala Pro Glu Asp Thr Leu Pro Phe Leu Lys Cys Tyr Cys Ser Gly
    130                 135                 140

His Cys Pro Asp Asp Ala Ile Asn Asn Thr Cys Ile Thr Asn Gly His
145                 150                 155                 160

Cys Phe Ala Ile Ile Glu Glu Asp Asp Gln Gly Glu Thr Thr Leu Ala
                165                 170                 175

Ser Gly Cys Met Lys Tyr Glu Gly Ser Asp Phe Gln Cys Lys Asp Ser
            180                 185                 190

Pro Lys Ala Gln Leu Arg Arg Thr Ile Glu Cys Cys Arg Thr Asn Leu
        195                 200                 205

Cys Asn Gln Tyr Leu Gln Pro Thr Leu Pro Pro Val Val Ile Gly Pro
    210                 215                 220

Phe Phe Asp Gly Ser Ile Arg
225                 230
```

<210> SEQ ID NO 59
<211> LENGTH: 213
<212> TYPE: PRT
<213> ORGANISM: Artificial Sequence
<220> FEATURE:
<223> OTHER INFORMATION: TbetaR-I/II-v2a

<400> SEQUENCE: 59

```
Ala Ala Leu Leu Pro Gly Ala Thr Ala Leu Gln Cys Phe Cys His Leu
1               5                   10                  15

Cys Thr Lys Asp Asn Phe Thr Cys Val Thr Asp Gly Leu Cys Phe Val
            20                  25                  30

Ser Val Thr Glu Thr Thr Asp Lys Val Ile His Asn Ser Met Cys Ile
        35                  40                  45

Ala Glu Ile Asp Leu Ile Pro Arg Asp Arg Pro Phe Val Cys Ala Pro
    50                  55                  60

Ser Ser Lys Thr Gly Ser Val Thr Thr Thr Tyr Cys Cys Asn Gln Asp
65                  70                  75                  80

His Cys Asn Lys Ile Glu Leu Gly Gly Gly Gly Gly Gly Gly Gly Asn
                85                  90                  95

Gly Ala Val Lys Phe Pro Gln Leu Cys Lys Phe Cys Asp Val Arg Phe
            100                 105                 110
```

```
Ser Thr Cys Asp Asn Gln Lys Ser Cys Met Ser Asn Cys Ser Ile Thr
        115                 120                 125

Ser Ile Cys Glu Lys Pro Gln Glu Val Cys Val Ala Val Trp Arg Lys
        130                 135                 140

Asn Asp Glu Asn Ile Thr Leu Glu Thr Val Cys His Asp Pro Lys Leu
145                 150                 155                 160

Pro Tyr His Asp Phe Ile Leu Glu Asp Ala Ala Ser Pro Lys Cys Ile
                165                 170                 175

Met Lys Glu Lys Lys Pro Gly Glu Thr Phe Phe Met Cys Ser Cys
                180                 185                 190

Ser Ser Asp Glu Cys Asn Asp Asn Ile Ile Phe Ser Glu Glu Tyr Asn
        195                 200                 205

Thr Ser Asn Pro Asp
        210

<210> SEQ ID NO 60
<211> LENGTH: 212
<212> TYPE: PRT
<213> ORGANISM: Artificial Sequence
<220> FEATURE:
<223> OTHER INFORMATION: TbetaR-I/II-v2b

<400> SEQUENCE: 60

Ala Ala Leu Leu Pro Gly Ala Thr Ala Leu Gln Cys Phe Cys His Leu
1               5                   10                  15

Cys Thr Lys Asp Asn Phe Thr Cys Val Thr Asp Gly Leu Cys Phe Val
                20                  25                  30

Ser Val Thr Glu Thr Thr Asp Lys Val Ile His Asn Ser Met Cys Ile
            35                  40                  45

Ala Glu Ile Asp Leu Ile Pro Arg Asp Arg Pro Phe Val Cys Ala Pro
    50                  55                  60

Ser Ser Lys Thr Gly Ser Val Thr Thr Thr Tyr Cys Cys Asn Gln Asp
65              70                  75                  80

His Cys Asn Lys Ile Glu Leu Gly Ser Gly Gly Ser Gly Asn Gly
                85                  90                  95

Ala Val Lys Phe Pro Gln Leu Cys Lys Phe Cys Asp Val Arg Phe Ser
                100                 105                 110

Thr Cys Asp Asn Gln Lys Ser Cys Met Ser Asn Cys Ser Ile Thr Ser
            115                 120                 125

Ile Cys Glu Lys Pro Gln Glu Val Cys Val Ala Val Trp Arg Lys Asn
    130                 135                 140

Asp Glu Asn Ile Thr Leu Glu Thr Val Cys His Asp Pro Lys Leu Pro
145                 150                 155                 160

Tyr His Asp Phe Ile Leu Glu Asp Ala Ala Ser Pro Lys Cys Ile Met
                165                 170                 175

Lys Glu Lys Lys Lys Pro Gly Glu Thr Phe Phe Met Cys Ser Cys Ser
                180                 185                 190

Ser Asp Glu Cys Asn Asp Asn Ile Ile Phe Ser Glu Glu Tyr Asn Thr
            195                 200                 205

Ser Asn Pro Asp
    210

<210> SEQ ID NO 61
<211> LENGTH: 213
<212> TYPE: PRT
<213> ORGANISM: Artificial Sequence
<220> FEATURE:
<223> OTHER INFORMATION: TbetaR-I/II-v2c
```

<400> SEQUENCE: 61

```
Ala Ala Leu Leu Pro Gly Ala Thr Ala Leu Gln Cys Phe Cys His Leu
1               5                   10                  15
Cys Thr Lys Asp Asn Phe Thr Cys Val Thr Asp Gly Leu Cys Phe Val
            20                  25                  30
Ser Val Thr Glu Thr Thr Asp Lys Val Ile His Asn Ser Met Cys Ile
        35                  40                  45
Ala Glu Ile Asp Leu Ile Pro Arg Asp Arg Pro Phe Val Cys Ala Pro
50                  55                  60
Ser Ser Lys Thr Gly Ser Val Thr Thr Thr Tyr Cys Cys Asn Gln Asp
65                  70                  75                  80
His Cys Asn Lys Ile Glu Leu Gly Gly Ser Gly Gly Ser Gly Gly Asn
                85                  90                  95
Gly Ala Val Lys Phe Pro Gln Leu Cys Lys Phe Cys Asp Val Arg Phe
            100                 105                 110
Ser Thr Cys Asp Asn Gln Lys Ser Cys Met Ser Asn Cys Ser Ile Thr
        115                 120                 125
Ser Ile Cys Glu Lys Pro Gln Glu Val Cys Val Ala Val Trp Arg Lys
130                 135                 140
Asn Asp Glu Asn Ile Thr Leu Glu Thr Val Cys His Asp Pro Lys Leu
145                 150                 155                 160
Pro Tyr His Asp Phe Ile Leu Glu Asp Ala Ala Ser Pro Lys Cys Ile
                165                 170                 175
Met Lys Glu Lys Lys Pro Gly Glu Thr Phe Phe Met Cys Ser Cys
            180                 185                 190
Ser Ser Asp Glu Cys Asn Asp Asn Ile Ile Phe Ser Glu Glu Tyr Asn
        195                 200                 205
Thr Ser Asn Pro Asp
        210

<210> SEQ ID NO 62
<211> LENGTH: 221
<212> TYPE: PRT
<213> ORGANISM: Artificial Sequence
<220> FEATURE:
<223> OTHER INFORMATION: ActR-IIa/BMPR-Ia-v2

<400> SEQUENCE: 62

Ala Ile Leu Gly Arg Ser Glu Thr Gln Glu Cys Leu Phe Phe Asn Ala
1               5                   10                  15
Asn Trp Glu Lys Asp Arg Thr Asn Gln Thr Gly Val Glu Pro Cys Tyr
            20                  25                  30
Gly Asp Lys Asp Lys Arg Arg His Cys Phe Ala Thr Trp Lys Asn Ile
        35                  40                  45
Ser Gly Ser Ile Glu Ile Val Lys Gln Gly Cys Trp Leu Asp Asp Ile
50                  55                  60
Asn Cys Tyr Asp Arg Thr Asp Cys Val Glu Lys Lys Asp Ser Pro Glu
65                  70                  75                  80
Val Tyr Phe Cys Cys Cys Glu Gly Asn Met Cys Asn Glu Lys Phe Ser
                85                  90                  95
Tyr Phe Pro Gly Gly Gly Gly Gly Gly Gly Gly Gly Gly Gly
            100                 105                 110
Gly Gly Gly Gly Gly Gly Gly Gly Gly Gly Thr Leu Pro Phe Leu
        115                 120                 125
Lys Cys Tyr Cys Ser Gly His Cys Pro Asp Asp Ala Ile Asn Asn Thr
```

```
                130                 135                 140
Cys Ile Thr Asn Gly His Cys Phe Ala Ile Ile Glu Glu Asp Asp Gln
145                 150                 155                 160

Gly Glu Thr Thr Leu Ala Ser Gly Cys Met Lys Tyr Glu Gly Ser Asp
                165                 170                 175

Phe Gln Cys Lys Asp Ser Pro Lys Ala Gln Leu Arg Arg Thr Ile Glu
            180                 185                 190

Cys Cys Arg Thr Asn Leu Cys Asn Gln Tyr Leu Gln Pro Thr Leu Pro
        195                 200                 205

Pro Val Val Ile Gly Pro Phe Phe Asp Gly Ser Ile Arg
210                 215                 220

<210> SEQ ID NO 63
<211> LENGTH: 223
<212> TYPE: PRT
<213> ORGANISM: Artificial Sequence
<220> FEATURE:
<223> OTHER INFORMATION: ActR-IIa/BMPR-Ia-v2a

<400> SEQUENCE: 63

Ala Ile Leu Gly Arg Ser Glu Thr Gln Glu Cys Leu Phe Phe Asn Ala
1               5                   10                  15

Asn Trp Glu Lys Asp Arg Thr Asn Gln Thr Gly Val Glu Pro Cys Tyr
            20                  25                  30

Gly Asp Lys Asp Lys Arg Arg His Cys Phe Ala Thr Trp Lys Asn Ile
        35                  40                  45

Ser Gly Ser Ile Glu Ile Val Lys Gln Gly Cys Trp Leu Asp Asp Ile
    50                  55                  60

Asn Cys Tyr Asp Arg Thr Asp Cys Val Glu Lys Lys Asp Ser Pro Glu
65                  70                  75                  80

Val Tyr Phe Cys Cys Cys Glu Gly Asn Met Cys Asn Glu Lys Phe Ser
                85                  90                  95

Tyr Phe Pro Gly Gly Ser Gly Gly Ser Gly Gly Ser Gly Gly Ser Gly
            100                 105                 110

Gly Ser Gly Gly Ser Gly Gly Ser Gly Gly Ser Gly Gly Thr Leu Pro
        115                 120                 125

Phe Leu Lys Cys Tyr Cys Ser Gly His Cys Pro Asp Asp Ala Ile Asn
    130                 135                 140

Asn Thr Cys Ile Thr Asn Gly His Cys Phe Ala Ile Ile Glu Glu Asp
145                 150                 155                 160

Asp Gln Gly Glu Thr Thr Leu Ala Ser Gly Cys Met Lys Tyr Glu Gly
                165                 170                 175

Ser Asp Phe Gln Cys Lys Asp Ser Pro Lys Ala Gln Leu Arg Arg Thr
            180                 185                 190

Ile Glu Cys Cys Arg Thr Asn Leu Cys Asn Gln Tyr Leu Gln Pro Thr
        195                 200                 205

Leu Pro Pro Val Val Ile Gly Pro Phe Phe Asp Gly Ser Ile Arg
    210                 215                 220

<210> SEQ ID NO 64
<211> LENGTH: 230
<212> TYPE: PRT
<213> ORGANISM: Artificial Sequence
<220> FEATURE:
<223> OTHER INFORMATION: ActR-IIa/BMPR-Ia-v2b

<400> SEQUENCE: 64

Ala Ile Leu Gly Arg Ser Glu Thr Gln Glu Cys Leu Phe Phe Asn Ala
```

```
                  1               5                  10                 15
Asn Trp Glu Lys Asp Arg Thr Asn Gln Thr Gly Val Glu Pro Cys Tyr
                 20                 25                 30
Gly Asp Lys Asp Lys Arg Arg His Cys Phe Ala Thr Trp Lys Asn Ile
             35                 40                 45
Ser Gly Ser Ile Glu Ile Val Lys Gln Gly Cys Trp Leu Asp Asp Ile
 50                 55                 60
Asn Cys Tyr Asp Arg Thr Asp Cys Val Glu Lys Lys Asp Ser Pro Glu
 65                 70                 75                 80
Val Tyr Phe Cys Cys Cys Glu Gly Asn Met Cys Asn Glu Lys Phe Ser
                 85                 90                 95
Tyr Phe Pro Gly Gly Ser Gly Gly Ser Gly Gly Ser Gly Gly
                100                105                110
Gly Ser Gly Gly Ser Gly Gly Ser Gly Gly Ser Gly Gly
            115                120                125
Gly Ser Gly Gly Thr Leu Pro Phe Leu Lys Cys Tyr Cys Ser Gly His
            130                135                140
Cys Pro Asp Asp Ala Ile Asn Asn Thr Cys Ile Thr Asn Gly His Cys
145                150                155                160
Phe Ala Ile Ile Glu Glu Asp Asp Gln Gly Glu Thr Thr Leu Ala Ser
                165                170                175
Gly Cys Met Lys Tyr Glu Gly Ser Asp Phe Gln Cys Lys Asp Ser Pro
                180                185                190
Lys Ala Gln Leu Arg Arg Thr Ile Glu Cys Cys Arg Thr Asn Leu Cys
                195                200                205
Asn Gln Tyr Leu Gln Pro Thr Leu Pro Pro Val Val Ile Gly Pro Phe
                210                215                220
Phe Asp Gly Ser Ile Arg
225                230

<210> SEQ ID NO 65
<211> LENGTH: 25
<212> TYPE: PRT
<213> ORGANISM: Artificial sequence
<220> FEATURE:
<223> OTHER INFORMATION: Synthetic linker
<220> FEATURE:
<221> NAME/KEY: 223
<222> LOCATION: (1)..(25)
<223> OTHER INFORMATION: synthetic linker 1; corresponds to SEQ ID NO 82
      as referred to in document WO 2008/113185 on page 46 line 8

<400> SEQUENCE: 65

Pro Phe Lys Val Ala Gly Asn Asn Asp Thr Val Ile Met Asp Asn Asn
1               5                  10                 15

Val Ser Lys Gln Val His Pro Pro Ile
            20                 25

<210> SEQ ID NO 66
<211> LENGTH: 10
<212> TYPE: PRT
<213> ORGANISM: Artificial sequence
<220> FEATURE:
<223> OTHER INFORMATION: synthetic linker

<400> SEQUENCE: 66

Asp Pro Asn Ser Thr Asn Tyr Glu Glu Ser
1               5                  10

<210> SEQ ID NO 67
```

```
<211> LENGTH: 50
<212> TYPE: PRT
<213> ORGANISM: Artificial sequence
<220> FEATURE:
<223> OTHER INFORMATION: Synthetic linker

<400> SEQUENCE: 67

Pro Phe Lys Val Ala Gly Asn Asn Asp Thr Val Ile Met Asp Asn Asn
1               5                   10                  15

Ile His Arg Leu Pro His Ala Thr Arg Asn Cys Ser Pro Cys Ile Ile
            20                  25                  30

Glu Asp Lys Gln Ala Glu Met Glu Val Asp Ser Lys Gln Val His Pro
        35                  40                  45

Pro Ile
    50

<210> SEQ ID NO 68
<211> LENGTH: 8
<212> TYPE: PRT
<213> ORGANISM: Artificial sequence
<220> FEATURE:
<223> OTHER INFORMATION: synthetic linker

<400> SEQUENCE: 68

Thr Ala Gly Pro Leu Leu Ala Ala
1               5

<210> SEQ ID NO 69
<211> LENGTH: 14
<212> TYPE: PRT
<213> ORGANISM: Artificial sequence
<220> FEATURE:
<223> OTHER INFORMATION: synthetic linker

<400> SEQUENCE: 69

Glu Val Pro Gly Leu Gly Pro Ser Ser Lys Val Thr Thr Pro
1               5                   10

<210> SEQ ID NO 70
<211> LENGTH: 7
<212> TYPE: PRT
<213> ORGANISM: Artificial sequence
<220> FEATURE:
<223> OTHER INFORMATION: synthetic linker

<400> SEQUENCE: 70

Glu Ser Arg Gly Leu Ile Ala
1               5

<210> SEQ ID NO 71
<211> LENGTH: 21
<212> TYPE: PRT
<213> ORGANISM: Artificial sequence
<220> FEATURE:
<223> OTHER INFORMATION: synthetic linker

<400> SEQUENCE: 71

Ile Asn Tyr Tyr Pro Pro Lys Pro Thr Val Pro Asn Ser Thr Pro Gln
1               5                   10                  15

Thr Val Glu Met Glu
            20

<210> SEQ ID NO 72
<211> LENGTH: 8
<212> TYPE: PRT
<213> ORGANISM: Artificial sequence
```

-continued

```
<220> FEATURE:
<223> OTHER INFORMATION: synthetic linker

<400> SEQUENCE: 72

Thr Glu Ala Glu Gly Arg Gly Ser
1               5

<210> SEQ ID NO 73
<211> LENGTH: 17
<212> TYPE: PRT
<213> ORGANISM: Artificial sequence
<220> FEATURE:
<223> OTHER INFORMATION: synthetic linker

<400> SEQUENCE: 73

Thr Pro Ala Thr Pro Pro Glu Tyr Thr Val Glu Pro Gly Gly Ala
1               5                   10                  15

Glu

<210> SEQ ID NO 74
<211> LENGTH: 31
<212> TYPE: PRT
<213> ORGANISM: Artificial sequence
<220> FEATURE:
<223> OTHER INFORMATION: synthetic linker

<400> SEQUENCE: 74

Asp Glu Pro Ala Leu Thr Val Gly Asn Glu Ser Lys Lys Gln Asp Ser
1               5                   10                  15

Asp Ser Lys Met Gly Thr Gly His Leu Met Ser Asp Leu Asn Gln
            20                  25                  30

<210> SEQ ID NO 75
<211> LENGTH: 13
<212> TYPE: PRT
<213> ORGANISM: Artificial sequence
<220> FEATURE:
<223> OTHER INFORMATION: synthetic linker
<220> FEATURE:
<221> NAME/KEY: 223
<222> LOCATION: (1)..(13)
<223> OTHER INFORMATION: synthetic linker 38; corresponds to SEQ ID NO
      92 as referred to in document WO 2008/113185 in Table II on page
      46 line 20

<400> SEQUENCE: 75

Arg Ile Ser Gly Asp Phe Phe Pro Gly Ile Val Val Pro
1               5                   10

<210> SEQ ID NO 76
<211> LENGTH: 101
<212> TYPE: PRT
<213> ORGANISM: Artificial Sequence
<220> FEATURE:
<223> OTHER INFORMATION: Synthetic Linker

<400> SEQUENCE: 76

Phe Ile Ile Asn Asp Asn Cys Glu Asp Ser Ser Cys Ser Cys Met Phe
1               5                   10                  15

Phe Thr Glu Gly Pro Lys Lys Lys Glu Lys Met Ile Cys Lys Pro Ser
            20                  25                  30

Ala Ala Asp Glu Leu Ile Phe Asp His Tyr Pro Leu Lys Pro Asp His
            35                  40                  45

Cys Val Thr Glu Leu Thr Ile Asn Glu Asp Asn Lys Arg Trp Val Ala
        50                  55                  60
```

Val Cys Val Glu Gln Pro Lys Glu Cys Ile Ser Thr Ile Ser Cys Asn
65                  70                  75                  80

Ser Met Cys Ser Lys Gln Asn Asp Cys Thr Ser Phe Arg Val Asp Cys
                85                  90                  95

Phe Lys Cys Leu Gln
            100

<210> SEQ ID NO 77
<211> LENGTH: 101
<212> TYPE: PRT
<213> ORGANISM: Artificial Sequence
<220> FEATURE:
<223> OTHER INFORMATION: Synthetic Linker

<400> SEQUENCE: 77

Phe Ile Ile Asn Asp Asn Cys Glu Asp Ser Ser Cys Ser Cys Met Phe
1               5                   10                  15

Phe Thr Glu Gly Pro Lys Lys Lys Glu Lys Met Ile Cys Lys Pro Ser
            20                  25                  30

Ala Ala Asp Glu Leu Ile Phe Asp His Tyr Pro Leu Lys Pro Asp His
        35                  40                  45

Cys Val Thr Glu Leu Thr Ile Asn Glu Asp Asn Lys Arg Trp Val Ala
    50                  55                  60

Val Cys Val Glu Gln Pro Lys Glu Cys Ile Ser Thr Ile Ser Cys Asn
65                  70                  75                  80

Ser Met Cys Ser Lys Gln Asn Asp Cys Thr Ser Phe Arg Val Asp Cys
                85                  90                  95

Phe Lys Cys Leu Gln
            100

<210> SEQ ID NO 78
<211> LENGTH: 79
<212> TYPE: PRT
<213> ORGANISM: Artificial Sequence
<220> FEATURE:
<223> OTHER INFORMATION: Synthetic Linker

<400> SEQUENCE: 78

Leu Glu Ile Lys Asn Cys His Asp Gln Asn Cys Cys Tyr Thr Thr Thr
1               5                   10                  15

Val Ser Gly Thr Lys Ser Ser Pro Ala Cys Val Phe Pro Arg Asp Arg
            20                  25                  30

Pro Ile Leu Asp Ile Glu Ala Ile Cys Met Ser Asn His Ile Val Lys
        35                  40                  45

Asp Thr Thr Glu Thr Val Ser Val Phe Cys Leu Gly Asp Thr Val Cys
    50                  55                  60

Thr Phe Asn Asp Lys Thr Cys Leu His Cys Phe Cys Gln Leu Ala
65                  70                  75

<210> SEQ ID NO 79
<211> LENGTH: 92
<212> TYPE: PRT
<213> ORGANISM: Artificial Sequence
<220> FEATURE:
<223> OTHER INFORMATION: Synthetic Linker

<400> SEQUENCE: 79

Pro Phe Tyr Ser Phe Lys Glu Asn Cys Met Asn Gly Glu Cys Cys Cys
1               5                   10                  15

Phe Tyr Val Glu Pro Ser Asp Lys Lys Glu Val Cys Asp Thr Arg Asp
            20                  25                  30

Tyr Cys Asn Ile Asp Asp Leu Trp Cys Gly Gln Lys Val Ile Glu Ile
                35                  40                  45

Ser Gly Ser Ile Asn Lys Trp Thr Ala Phe Cys His Arg Arg Lys Asp
    50                  55                  60

Lys Asp Gly Tyr Cys Pro Glu Val Gly Thr Gln Asn Thr Arg Asp Lys
65                  70                  75                  80

Glu Trp Asn Ala Asn Phe Phe Leu Cys Glu Gln Thr
                85                  90

<210> SEQ ID NO 80
<211> LENGTH: 108
<212> TYPE: PRT
<213> ORGANISM: Artificial Sequence
<220> FEATURE:
<223> OTHER INFORMATION: Synthetic Linker

<400> SEQUENCE: 80

Thr Pro Ala Thr Pro Pro Glu Tyr Thr Val Glu Pro Gly Gly Ala
1               5                   10                  15

Glu Pro Leu His Thr Phe Arg Glu Asn Cys Phe Asn Gly Glu Cys Cys
                20                  25                  30

Cys Phe Tyr Val Gln Pro Asn Glu Glu Thr Ala Val Cys Glu Gln Arg
            35                  40                  45

Asp Tyr Cys Asn Phe Asp Asp Leu Trp Cys Gly Lys Lys Val Leu Glu
    50                  55                  60

Ile Thr Gly Ser Ser Asn Arg Trp Ser Ala Tyr Cys His Leu Arg Lys
65                  70                  75                  80

Asp Gln Glu Gly Glu Cys Arg Glu Leu Gly Ser Gln Asn Thr Arg Glu
                85                  90                  95

Leu Glu Trp Asn Ala Asn Tyr Tyr Ile Cys Glu Arg
                100                 105

<210> SEQ ID NO 81
<211> LENGTH: 98
<212> TYPE: PRT
<213> ORGANISM: Artificial Sequence
<220> FEATURE:
<223> OTHER INFORMATION: Synthetic Linker

<400> SEQUENCE: 81

Arg Ile Ser Gly Asp Phe Phe Pro Gly Ile Val Val Pro Pro Leu Thr
1               5                   10                  15

Pro Gln Leu Tyr Gln Asn Cys Leu Asn Thr Arg Cys Cys Glu Ile Thr
                20                  25                  30

Arg Arg Leu Gln Ala Lys Pro Ser Asp Lys Cys Gln Phe Asp Ser Gly
            35                  40                  45

Glu Tyr Lys Met Cys Gly Ser Ala Leu Thr Thr Glu Gly Gln Asp Asp
    50                  55                  60

Glu Glu Ile Ile Ala Phe Cys His Gly Asn Thr Ile Cys Thr Asn Asn
65                  70                  75                  80

Ile Ala Asp Asp Pro Cys His Gly Ser Cys Tyr Cys Lys Leu Phe Pro
                85                  90                  95

Leu Thr

<210> SEQ ID NO 82
<211> LENGTH: 35
<212> TYPE: PRT
<213> ORGANISM: Artificial sequence
<220> FEATURE:

<223> OTHER INFORMATION: synthetic linker

<400> SEQUENCE: 82

Pro Phe Lys Val Ala Gly Asn Asn Asp Thr Val Ile Met Asp Asn Asn
1               5                   10                  15

Val Ser Lys Gln Val His Pro Pro Ile Asp Pro Asn Ser Thr Asn Tyr
            20                  25                  30

Glu Glu Ser
        35

<210> SEQ ID NO 83
<211> LENGTH: 60
<212> TYPE: PRT
<213> ORGANISM: Artificial sequence
<220> FEATURE:
<223> OTHER INFORMATION: synthetic linker

<400> SEQUENCE: 83

Pro Phe Lys Val Ala Gly Asn Asn Asp Thr Val Ile Met Asp Asn Asn
1               5                   10                  15

Ile His Arg Leu Pro His Ala Thr Arg Asn Cys Ser Pro Cys Ile Ile
            20                  25                  30

Glu Asp Lys Gln Ala Glu Met Glu Val Asp Ser Lys Gln Val His Pro
        35                  40                  45

Pro Ile Asp Pro Asn Ser Thr Asn Tyr Glu Glu Ser
    50                  55                  60

<210> SEQ ID NO 84
<211> LENGTH: 25
<212> TYPE: PRT
<213> ORGANISM: Artificial sequence
<220> FEATURE:
<223> OTHER INFORMATION: synthetic linker

<400> SEQUENCE: 84

Thr Glu Ala Glu Gly Arg Gly Ser Thr Pro Ala Thr Pro Pro Pro Glu
1               5                   10                  15

Tyr Thr Val Glu Pro Gly Gly Ala Glu
            20                  25

<210> SEQ ID NO 85
<211> LENGTH: 44
<212> TYPE: PRT
<213> ORGANISM: Artificial sequence
<220> FEATURE:
<223> OTHER INFORMATION: synthetic linker

<400> SEQUENCE: 85

Asp Glu Pro Ala Leu Thr Val Gly Asn Glu Ser Lys Lys Gln Asp Ser
1               5                   10                  15

Asp Ser Lys Met Gly Thr Gly His Leu Met Ser Asp Leu Asn Gln Arg
            20                  25                  30

Ile Ser Gly Asp Phe Phe Pro Gly Ile Val Val Pro
        35                  40

<210> SEQ ID NO 86
<211> LENGTH: 44
<212> TYPE: PRT
<213> ORGANISM: Artificial sequence
<220> FEATURE:
<223> OTHER INFORMATION: synthetic linker

<400> SEQUENCE: 86

Asp Glu Pro Ala Leu Thr Val Gly Asn Glu Ser Lys Lys Gln Asp Ser
1               5                   10                  15

Asp Ser Lys Met Gly Thr Gly His Leu Met Ser Asp Leu Asn Gly Arg
                20                  25                  30

Ile Ser Gly Asp Phe Phe Pro Gly Ile Val Pro
            35                  40

<210> SEQ ID NO 87
<211> LENGTH: 35
<212> TYPE: PRT
<213> ORGANISM: Artificial sequence
<220> FEATURE:
<223> OTHER INFORMATION: synthetic linker

<400> SEQUENCE: 87

Pro Phe Lys Val Ala Gly Asn Asn Asp Thr Val Ile Met Asp Asn Asn
1               5                   10                  15

Val Ser Lys Gln Val His Pro Pro Gly Asp Pro Asn Ser Thr Asn Tyr
                20                  25                  30

Glu Glu Ser
        35

<210> SEQ ID NO 88
<211> LENGTH: 25
<212> TYPE: PRT
<213> ORGANISM: Artificial sequence
<220> FEATURE:
<223> OTHER INFORMATION: synthetic linker

<400> SEQUENCE: 88

Thr Glu Ala Glu Gly Arg Gly Ser Thr Pro Ala Thr Pro Pro Pro Glu
1               5                   10                  15

Gly Thr Val Glu Pro Gly Gly Ala Glu
                20                  25

<210> SEQ ID NO 89
<211> LENGTH: 60
<212> TYPE: PRT
<213> ORGANISM: Artificial sequence
<220> FEATURE:
<223> OTHER INFORMATION: synthetic linker

<400> SEQUENCE: 89

Pro Phe Lys Val Ala Gly Asn Asn Asp Thr Val Ile Met Asp Asn Asn
1               5                   10                  15

Ile His Arg Leu Pro His Ala Thr Arg Asn Cys Ser Pro Cys Ile Ile
                20                  25                  30

Glu Asp Lys Gln Ala Glu Met Glu Val Asp Ser Lys Gln Val His Arg
                35                  40                  45

Gly Gly Asp Pro Asn Ser Thr Asn Tyr Glu Glu Ser
            50                  55                  60

<210> SEQ ID NO 90
<211> LENGTH: 35
<212> TYPE: PRT
<213> ORGANISM: Artificial sequence
<220> FEATURE:
<223> OTHER INFORMATION: synthetic linker

<400> SEQUENCE: 90

Pro Phe Lys Val Ala Gly Asn Asn Asp Thr Val Ile Met Asp Asn Asn
1               5                   10                  15

Val Ser Lys Gln Val His Pro Gly Gly Asp Pro Asn Ser Thr Asn Tyr

```
                    20                  25                  30

Glu Glu Ser
        35

<210> SEQ ID NO 91
<211> LENGTH: 35
<212> TYPE: PRT
<213> ORGANISM: Artificial sequence
<220> FEATURE:
<223> OTHER INFORMATION: synthetic linker

<400> SEQUENCE: 91

Pro Phe Lys Val Ala Gly Asn Asn Asp Thr Val Ile Met Asp Asn Asn
1               5                   10                  15

Val Ser Lys Gln Val His Arg Gly Gly Asp Pro Asn Ser Thr Asn Tyr
            20                  25                  30

Glu Glu Ser
        35

<210> SEQ ID NO 92
<211> LENGTH: 60
<212> TYPE: PRT
<213> ORGANISM: Artificial sequence
<220> FEATURE:
<223> OTHER INFORMATION: synthetic linker

<400> SEQUENCE: 92

Pro Phe Lys Val Ala Gly Asn Asn Asp Thr Val Ile Met Asp Asn Asn
1               5                   10                  15

Ile His Arg Leu Pro His Ala Thr Arg Asn Cys Ser Pro Cys Ile Ile
            20                  25                  30

Glu Asp Lys Gln Ala Glu Met Gly Gly Gly Ser Gly Gly Gly Ser Gly
        35                  40                  45

Gly Gly Ser Pro Asn Ser Thr Asn Tyr Glu Glu Ser
    50                  55                  60

<210> SEQ ID NO 93
<211> LENGTH: 35
<212> TYPE: PRT
<213> ORGANISM: Artificial sequence
<220> FEATURE:
<223> OTHER INFORMATION: synthetic linker

<400> SEQUENCE: 93

Pro Phe Lys Val Ala Gly Asn Asn Asp Thr Val Ile Met Asp Asn Asn
1               5                   10                  15

Val Ser Lys Gly Gly Ser Gly Gly Gly Ser Pro Asn Ser Thr Asn Tyr
            20                  25                  30

Glu Glu Ser
        35

<210> SEQ ID NO 94
<211> LENGTH: 35
<212> TYPE: PRT
<213> ORGANISM: Artificial sequence
<220> FEATURE:
<223> OTHER INFORMATION: synthetic linker

<400> SEQUENCE: 94

Pro Phe Lys Val Ala Gly Asn Asn Asp Thr Val Ile Met Asp Gly Gly
1               5                   10                  15

Gly Ser Gly Gly Gly Ser Gly Gly Gly Ser Pro Asn Ser Thr Asn Tyr
            20                  25                  30
```

```
Glu Glu Ser
        35

<210> SEQ ID NO 95
<211> LENGTH: 60
<212> TYPE: PRT
<213> ORGANISM: Artificial sequence
<220> FEATURE:
<223> OTHER INFORMATION: synthetic linker

<400> SEQUENCE: 95

Pro Phe Lys Val Ala Gly Asn Asn Asp Thr Val Ile Met Asp Asn Asn
1               5                  10                  15

Gly Gly Ser Gly Gly Gly Ser Gly Gly Gly Ser Gly Gly Gly Ser Gly
            20                  25                  30

Gly Gly Ser Gly Gly Gly Ser Gly Gly Gly Ser Lys Gln Val His Pro
        35                  40                  45

Pro Ile Asp Pro Asn Ser Thr Asn Tyr Glu Glu Ser
    50                  55                  60

<210> SEQ ID NO 96
<211> LENGTH: 60
<212> TYPE: PRT
<213> ORGANISM: Artificial sequence
<220> FEATURE:
<223> OTHER INFORMATION: synthetic linker

<400> SEQUENCE: 96

Pro Phe Lys Val Ala Gly Asn Asn Asp Thr Val Ile Met Asp Asn Asn
1               5                  10                  15

Gly Gly Ser Gly Gly Gly Ser Gly Gly Gly Ser Gly Gly Gly Ser Gly
            20                  25                  30

Gly Gly Ser Gly Gly Gly Ser Gly Gly Gly Ser Gly Gly Gly Ser Gly
        35                  40                  45

Gly Gly Asp Pro Asn Ser Thr Asn Tyr Glu Glu Ser
    50                  55                  60

<210> SEQ ID NO 97
<211> LENGTH: 35
<212> TYPE: PRT
<213> ORGANISM: Artificial sequence
<220> FEATURE:
<223> OTHER INFORMATION: synthetic linker

<400> SEQUENCE: 97

Pro Phe Lys Val Ala Gly Asn Asn Asp Thr Val Ile Met Asp Asn Asn
1               5                  10                  15

Val Ser Lys Gln Val His Pro Pro Ile Asp Pro Asn Ser Thr Asn Tyr
            20                  25                  30

Glu Glu Ser
        35

<210> SEQ ID NO 98
<211> LENGTH: 48
<212> TYPE: PRT
<213> ORGANISM: Artificial sequence
<220> FEATURE:
<223> OTHER INFORMATION: synthetic linker

<400> SEQUENCE: 98

Pro Phe Lys Val Ala Gly Asn Asn Asp Thr Val Ile Met Asp Asn Asn
1               5                  10                  15
```

```
Val Ser Lys Gln Val His Pro Pro Ile Met Asp Asn Asn Val Ser Lys
            20                  25                  30

Gln Val His Pro Pro Ile Asp Pro Asn Ser Thr Asn Tyr Glu Glu Ser
            35                  40                  45
```

<210> SEQ ID NO 99
<211> LENGTH: 32
<212> TYPE: PRT
<213> ORGANISM: Artificial sequence
<220> FEATURE:
<223> OTHER INFORMATION: synthetic linker

<400> SEQUENCE: 99

```
Pro Phe Lys Val Ala Gly Asn Asn Asp Thr Val Ile Met Asp Asn Asn
1               5                   10                  15

Val Ser Lys Gln Val His Pro Pro Asn Ser Thr Asn Tyr Glu Glu Ser
            20                  25                  30
```

<210> SEQ ID NO 100
<211> LENGTH: 43
<212> TYPE: PRT
<213> ORGANISM: Artificial sequence
<220> FEATURE:
<223> OTHER INFORMATION: synthetic linker

<400> SEQUENCE: 100

```
Pro Phe Lys Val Ala Gly Asn Asn Asp Thr Val Ile Met Asp Asn Asn
1               5                   10                  15

Val Ser Lys Gln Val His Pro Pro Ile Gly Gly Gly Gly Gly Gly Gly
            20                  25                  30

Gly Asp Pro Asn Ser Thr Asn Tyr Glu Glu Ser
        35                  40
```

<210> SEQ ID NO 101
<211> LENGTH: 47
<212> TYPE: PRT
<213> ORGANISM: Artificial sequence
<220> FEATURE:
<223> OTHER INFORMATION: synthetic linker

<400> SEQUENCE: 101

```
Pro Phe Lys Val Ala Gly Asn Asn Asp Thr Val Ile Met Asp Asn Asn
1               5                   10                  15

Val Ser Lys Gln Val His Pro Pro Ile Ser Gly Gly Gly Ser Gly Gly
            20                  25                  30

Gly Ser Gly Gly Gly Asp Pro Asn Ser Thr Asn Tyr Glu Glu Ser
        35                  40                  45
```

<210> SEQ ID NO 102
<211> LENGTH: 60
<212> TYPE: PRT
<213> ORGANISM: Artificial sequence
<220> FEATURE:
<223> OTHER INFORMATION: synthetic linker

<400> SEQUENCE: 102

```
Pro Phe Lys Val Ala Gly Asn Asn Asp Thr Val Ile Met Asp Asn Asn
1               5                   10                  15

Ile His Arg Leu Pro His Ala Thr Arg Asn Cys Ser Pro Cys Ile Ile
            20                  25                  30

Glu Asp Lys Gln Ala Glu Met Glu Val Asp Ser Lys Gln Val His Pro
            35                  40                  45

Pro Ile Asp Pro Asn Ser Thr Asn Tyr Glu Glu Ser
```

<210> SEQ ID NO 103
<211> LENGTH: 53
<212> TYPE: PRT
<213> ORGANISM: Artificial sequence
<220> FEATURE:
<223> OTHER INFORMATION: synthetic linker

<400> SEQUENCE: 103

Pro Phe Lys Val Ala Gly Asn Asn Asp Thr Val Ile Met Asp Asn Asn
1               5                   10                  15

Ile His Arg Leu Pro His Ala Thr Arg Glu Asp Lys Gln Ala Glu Met
            20                  25                  30

Glu Val Asp Ser Lys Gln Val His Pro Pro Ile Asp Pro Asn Ser Thr
        35                  40                  45

Asn Tyr Glu Glu Ser
    50

<210> SEQ ID NO 104
<211> LENGTH: 25
<212> TYPE: PRT
<213> ORGANISM: Artificial sequence
<220> FEATURE:
<223> OTHER INFORMATION: synthetic linker

<400> SEQUENCE: 104

Thr Glu Ala Glu Gly Arg Gly Ser Thr Pro Ala Thr Pro Pro Glu
1               5                   10                  15

Tyr Thr Val Glu Pro Gly Gly Ala Glu
            20                  25

<210> SEQ ID NO 105
<211> LENGTH: 35
<212> TYPE: PRT
<213> ORGANISM: Artificial sequence
<220> FEATURE:
<223> OTHER INFORMATION: synthetic linker

<400> SEQUENCE: 105

Thr Glu Ala Glu Gly Arg Gly Ser Gly Gly Gly Gly Gly Gly Gly
1               5                   10                  15

Gly Gly Thr Pro Ala Thr Pro Pro Glu Tyr Thr Val Glu Pro Gly
            20                  25                  30

Gly Ala Glu
        35

<210> SEQ ID NO 106
<211> LENGTH: 44
<212> TYPE: PRT
<213> ORGANISM: Artificial sequence
<220> FEATURE:
<223> OTHER INFORMATION: synthetic linker

<400> SEQUENCE: 106

Asp Glu Pro Ala Leu Thr Val Gly Asn Glu Ser Lys Lys Gln Asp Ser
1               5                   10                  15

Asp Ser Lys Met Gly Thr Gly His Leu Met Ser Asp Leu Asn Gln Arg
            20                  25                  30

Ile Ser Gly Asp Phe Phe Pro Gly Ile Val Val Pro
        35                  40

<210> SEQ ID NO 107

```
<211> LENGTH: 40
<212> TYPE: PRT
<213> ORGANISM: Artificial sequence
<220> FEATURE:
<223> OTHER INFORMATION: synthetic linker

<400> SEQUENCE: 107

Asp Glu Pro Ala Leu Thr Val Gly Asn Glu Ser Lys Lys Gln Asp Ser
1               5                   10                  15

Asp Ser Lys Met Gly Thr Gly His Ser Asp Leu Asn Gln Arg Ile Ser
            20                  25                  30

Gly Asp Pro Gly Ile Val Val Pro
        35                  40

<210> SEQ ID NO 108
<211> LENGTH: 51
<212> TYPE: PRT
<213> ORGANISM: Artificial Sequence
<220> FEATURE:
<223> OTHER INFORMATION: Synthetic Linker

<400> SEQUENCE: 108

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His His His His His His His Gly Gly Ser Phe
        35                  40                  45

Asn Pro Arg
        50
```